(12) United States Patent
Liu et al.

(10) Patent No.: US 11,124,515 B2
(45) Date of Patent: Sep. 21, 2021

(54) ADENOSINE RECEPTOR ANTAGONISTS AND USES THEREOF

(71) Applicant: Teon Therapeutics, Inc., Redwood City, CA (US)

(72) Inventors: Jiwen Liu, Foster City, CA (US); Elfatih Elzein, Mountain House, CA (US)

(73) Assignee: Teon Therapeutics, Inc., Redwood City, CA (US)

( * ) Notice: Subject to any disclaimer, the term of this patent is extended or adjusted under 35 U.S.C. 154(b) by 0 days.

(21) Appl. No.: 17/165,736

(22) Filed: Feb. 2, 2021

(65) Prior Publication Data

US 2021/0163483 A1 Jun. 3, 2021

Related U.S. Application Data

(63) Continuation of application No. 16/978,040, filed as application No. PCT/US2019/020810 on Mar. 5, 2019.

(60) Provisional application No. 62/638,737, filed on Mar. 5, 2018, provisional application No. 62/688,088, filed on Jun. 21, 2018.

(51) Int. Cl.
  *C07D 473/06* (2006.01)
  *A61K 9/08* (2006.01)
  *A61K 9/20* (2006.01)
  *A61K 9/48* (2006.01)

(52) U.S. Cl.
  CPC .............. *C07D 473/06* (2013.01); *A61K 9/08* (2013.01); *A61K 9/2054* (2013.01); *A61K 9/4825* (2013.01)

(58) Field of Classification Search
  CPC .. C07D 405/10; C07D 403/10; C07D 473/06; A61K 31/522
  USPC ........................ 544/224; 514/263.2, 263.23
  See application file for complete search history.

(56) References Cited

U.S. PATENT DOCUMENTS

| | | | |
|---|---|---|---|
| 6,825,349 B2 | 11/2004 | Kalla et al. | |
| 6,977,300 B2 | 12/2005 | Kalla et al. | |
| 7,105,665 B2 | 9/2006 | Kalla et al. | |
| 7,125,993 B2 | 10/2006 | Elzein et al. | |
| 7,304,070 B2 | 12/2007 | Kalla et al. | |
| 7,317,017 B2 | 1/2008 | Kalla et al. | |
| 7,625,881 B2 | 12/2009 | Kalla et al. | |
| 7,741,331 B2 | 6/2010 | Kalla et al. | |
| 7,795,268 B2 | 9/2010 | Zeng et al. | |
| 7,795,269 B2 | 9/2010 | Kalla et al. | |
| 8,143,249 B2 | 3/2012 | Kalla et al. | |
| 8,188,099 B2 | 5/2012 | Belardinelli et al. | |
| 8,324,224 B2 | 12/2012 | Kalla et al. | |
| 8,466,129 B2 | 6/2013 | Zeng et al. | |
| 8,609,671 B2 | 12/2013 | Belardinelli et al. | |
| 10,117,868 B2 | 11/2018 | Palczewski et al. | |
| 10,426,773 B2 | 10/2019 | Palczewski et al. | |
| 2003/0139428 A1 | 7/2003 | Kalla et al. | |
| 2008/0318983 A1 | 12/2008 | Kalla et al. | |
| 2011/0160162 A1 | 6/2011 | Kalla et al. | |
| 2012/0003329 A1 | 1/2012 | Belardinelli et al. | |
| 2019/0046448 A1 | 2/2019 | Wu | |
| 2019/0183976 A1 | 6/2019 | Seen et al. | |

FOREIGN PATENT DOCUMENTS

| | | |
|---|---|---|
| EP | 1789053 | 3/2006 |
| EP | 2595630 | 1/2012 |
| EP | 2694074 | 11/2012 |
| WO | WO 2008/066627 | 6/2008 |
| WO | WO 2009/088518 | 7/2009 |
| WO | WO 2009/118759 | 10/2009 |
| WO | WO 2009/157938 | 12/2009 |
| WO | WO 2019/036438 | 2/2019 |
| WO | WO 2019/124951 | 6/2019 |
| WO | WO 2019/173380 | 9/2019 |

OTHER PUBLICATIONS

Basu et al., "Design and synthesis of novel xanthine derivatives as potent and selective A2B adenosine receptor antagonists for the treatment of chronic inflammatory airway disease", European Journal of Medicinal Chemistry, 2017, vol. 134, pp. 218-229.
International Preliminary Report on Patentability, PCT/US2019/020810, dated Jun. 20, 2019, 9 pages.

*Primary Examiner* — Jeffrey H Murray
(74) *Attorney, Agent, or Firm* — Sheppard Mullin Richter & Hampton LLP

(57) ABSTRACT

Disclosed herein are compounds of Formula (III), compositions and formulations thereof, Formula (III)

and methods for modulating the $A_{2B}$ adenosine receptor for treatment of $A_{2B}$ adenosine receptor mediated diseases or conditions.

22 Claims, No Drawings

ADENOSINE RECEPTOR ANTAGONISTS AND USES THEREOF

CROSS-REFERENCE

This application is a continuation of U.S. application Ser. No. 16/978,040, filed Sep. 3, 2020, which is a national stage application of PCT International Application PCT/US2019/020810, filed Mar. 5, 2019, which claims the benefit of U.S. Provisional Application No. 62/638,737, filed Mar. 5, 2018 and U.S. Provisional Application No. 62/688,088 filed Jun. 21, 2018, which are all incorporated herein by reference in their entireties.

FIELD OF THE INVENTION

Described herein are compounds, methods of making such compounds, pharmaceutical compositions and medicaments comprising such compounds, and methods of using such compounds in the treatment of conditions, diseases, or disorders that would benefit from modulation of $A_{2B}$ adenosine receptor activity.

BACKGROUND OF THE INVENTION

Adenosine, an endogenous nucleoside, ubiquitously exists inside and outside of living cells. It plays multiple physiological roles to maintain the homeostasis of cells, tissues, and organs. Adenosine can exert its biological effects by interacting with a family of adenosine receptors known as $A_1$, $A_{2A}$, $A_{2B}$, and $A_3$ adenosine receptors. $A_1$ adenosine receptors mediate mechanisms of tissue protection, especially for cardioprotection. $A_{2A}$ adenosine receptors modulate coronary vasodilation and cancer immunity. $A_{2B}$ adenosine receptors play a role in signaling pathways.

Some $A_{2B}$ adenosine receptor antagonists are relatively insoluble in aqueous media and/or difficult to formulate using conventional pharmaceutical excipients, and thus can be difficult to formulate in a manner that provides reproducible plasma levels of the compound in mammals, in particular humans A need exists for improving the bioavailability $A_{2B}$ adenosine receptor antagonists.

SUMMARY OF THE INVENTION

In one aspect, described herein is a compound represented by Formula (A):

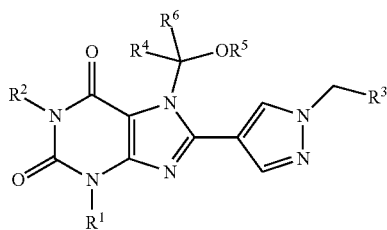

Formula (A)

or a pharmaceutically acceptable salt or solvate thereof, wherein:
$R^1$ and $R^2$ are each independently selected from hydrogen, and substituted or unsubstituted alkyl;
$R^3$ is selected from substituted or unsubstituted phenyl, and substituted or unsubstituted heteroaryl, wherein if $R^3$ is substituted then $R^3$ is substituted with one or more groups selected from halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, and substituted or unsubstituted $C_1$-$C_4$heteroalkyl;
$R^4$ is substituted or unsubstituted alkyl;
$R^6$ is hydrogen or substituted or unsubstituted alkyl;
or $R^4$ and $R^6$ are taken together with the carbon atom to which they are attached to form a carbonyl (C=O);
or $R^4$ and $R^6$ are taken together with the carbon atom to which they are attached to form a ring that is a substituted or unsubstituted $C_3$-$C_{10}$cycloalkyl, or substituted or unsubstituted $C_2$-$C_{10}$heterocycloalkyl, wherein if the ring is substituted then it is substituted with one or more $R^{15}$;
$R^{15}$ is hydrogen, substituted or unsubstituted alkyl, substituted or unsubstituted heteroalkyl, substituted or unsubstituted phenyl, substituted or unsubstituted heteroaryl, -alkyl-(substituted or unsubstituted phenyl), -alkyl-(substituted or unsubstituted heteroaryl), —C(=O)R$^{16}$, —C(=O)—OR$^{16}$, —C(=O)N(R$^{16}$)$_2$;
each $R^{16}$ is independently selected from hydrogen and substituted or unsubstituted alkyl;
$R^5$ is hydrogen, $R^7$, —C(=O)R$^7$, —C(=O)—OR$^7$, —C(=O)N(R$^7$)(R$^8$), —C(=O)—SR$^7$, or —P(=O)(OR$^9$)$_2$;
or $R^4$ and $R^5$ are taken together with the atoms to which they are attached to form a substituted or unsubstituted $C_2$-$C_{10}$heterocycloalkyl;
$R^7$ is substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C(R$^{10}$)$_2$O)$_m$—R$^{11}$, —(CH$_2$CH$_2$O)$_n$—R$^{11}$, or —(C(R$^{10}$)$_2$)$_p$—OR$^{11}$;
$R^8$ is hydrogen or alkyl;
or $R^7$ and $R^8$ are taken together with the nitrogen atom to which they are attached to form a substituted or unsubstituted $C_2$-$C_{10}$heterocycloalkyl;
each $R^9$ is independently selected from hydrogen and alkyl;
each $R^{10}$ is independently selected from hydrogen and alkyl;
$R^{11}$ is hydrogen, substituted or unsubstituted alkyl, substituted or unsubstituted heteroalkyl, substituted or unsubstituted $C_2$-$C_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OR$^9$)$_2$;
$R^{12}$ is hydrogen, substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), or -alkyl-(substituted or unsubstituted heteroaryl);
m is 1, 2, 3, 4, 5, or 6;
n is 1, 2, 3, 4, 5, or 6;
p is 1, 2, 3, 4, 5, or 6;
wherein substituted means that the referenced group is substituted with one or more additional groups individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH (alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone.

In some embodiments, R$^4$ is C$_1$-C$_6$alkyl; R$^6$ is selected from hydrogen, and C$_1$-C$_6$alkyl; or R$^4$ and R$^6$ are taken together with the carbon atom to which they are attached to form a carbonyl (C=O).

In some embodiments, R$^4$ is methyl, ethyl, or n-propyl; R$^6$ is selected from hydrogen, methyl, ethyl, and n-propyl; or R$^4$ and R$^6$ are taken together with the carbon atom to which they are attached to form a carbonyl (C=O).

In some embodiments, the compound has the following structure of Formula (III):

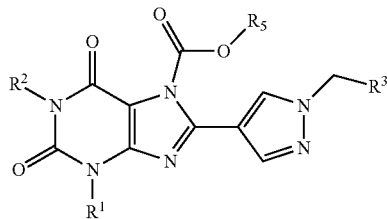

Formula (III)

or a pharmaceutically acceptable salt or solvate thereof.

In some embodiments, R$^1$ and R$^2$ are each independently selected from substituted or unsubstituted C$_1$-C$_6$alkyl; R$^3$ is selected from substituted or unsubstituted phenyl.

In some embodiments, R$^1$ and R$^2$ are each independently selected from methyl, ethyl, n-propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, and neohexyl.

In some embodiments, R$^1$ is ethyl; R$^2$ is n-propyl; and R$^3$ is 3-(trifluoromethyl)phenyl.

In some embodiments, the compound has the following structure:

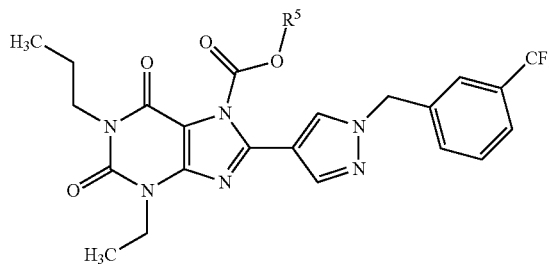

or a pharmaceutically acceptable salt or solvate thereof.

In some embodiments, R$^5$ is R$^7$; R$^7$ is C$_1$-C$_6$alkyl, substituted or unsubstituted C$_1$-C$_6$heteroalkyl, substituted or unsubstituted monocyclic C$_3$-C$_8$cycloalkyl, substituted or unsubstituted bicyclic C$_5$-C$_{10}$cycloalkyl, substituted or unsubstituted monocyclic C$_2$-C$_8$heterocycloalkyl, substituted or unsubstituted bicyclic C$_5$-C$_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH(R$^{10}$)O—R$^{11}$, —(CH$_2$CH$_2$O)$_n$—R$^{11}$, or —(C(R$^{10}$)$_2$)$_p$—OR$^{11}$; each R$^{10}$ is independently selected from hydrogen and methyl; R$^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OR$^9$)$_2$.

In some embodiments, R$^7$ is C$_1$-C$_6$alkyl, substituted or unsubstituted C$_1$-C$_6$heteroalkyl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH(R$^{10}$)O—R$^{11}$, or —(CH$_2$CH$_2$O)$_n$—R$^{11}$; R$_{10}$ is hydrogen and methyl; R$^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OH)$_2$.

In some embodiments, the compound has one of the following structures:

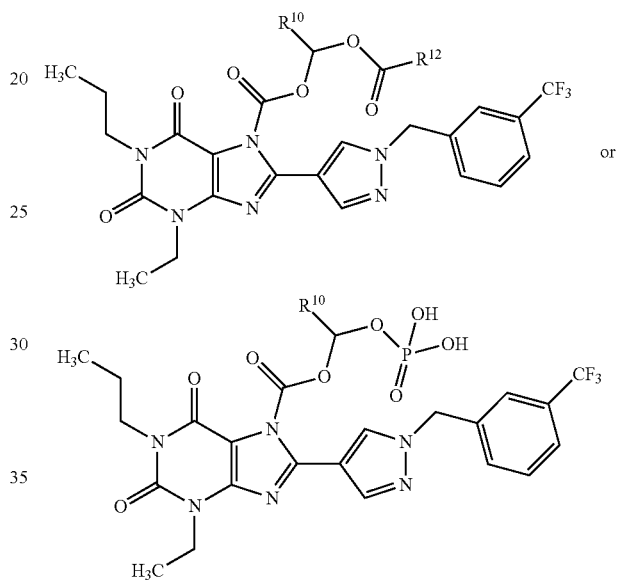

or or a pharmaceutically acceptable salt or solvate thereof.

In some embodiments, the compound has one of the following structures:

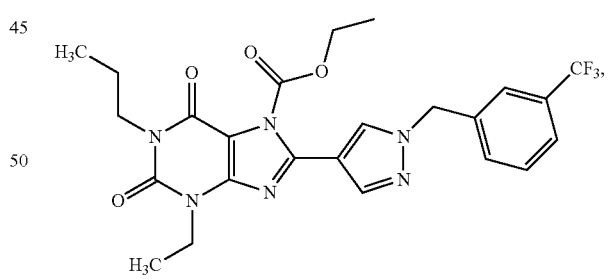

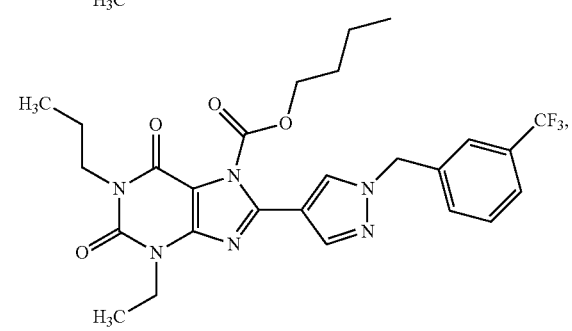

-continued

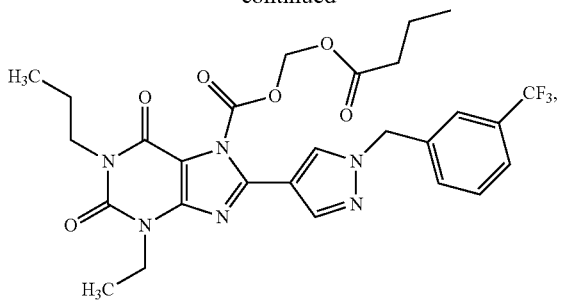

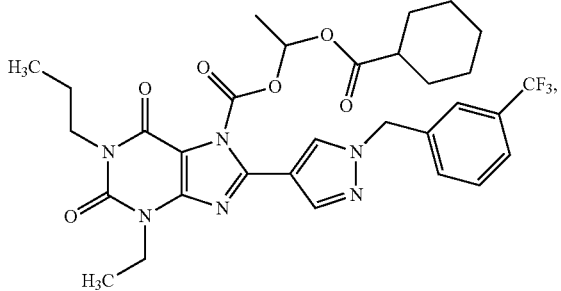

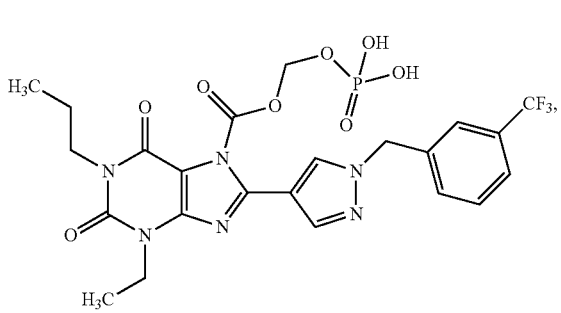

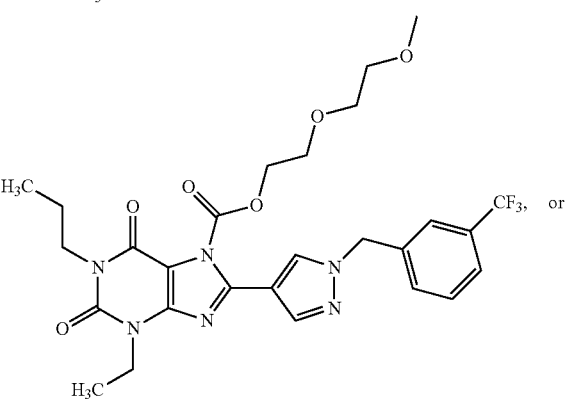

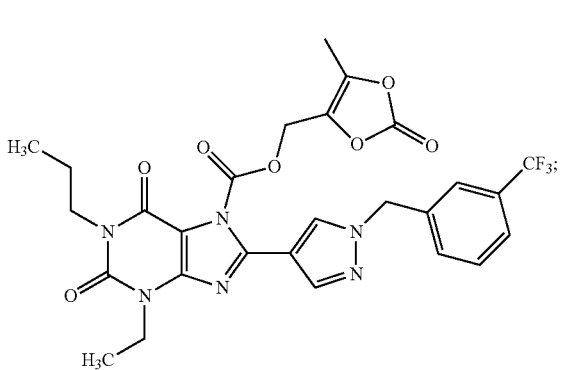

or a pharmaceutically acceptable salt or solvate thereof.

In some embodiments, the compound has the following structure of Formula (I):

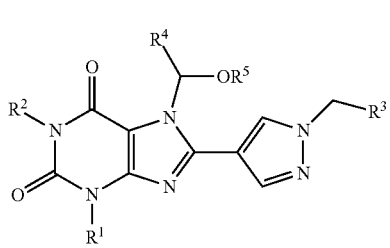

Formula (I)

or a pharmaceutically acceptable salt or solvate thereof.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ is ethyl; $R^2$ is n-propyl; and $R^3$ is 3-(trifluoromethyl)phenyl.

In some embodiments, the compound has the following structure:

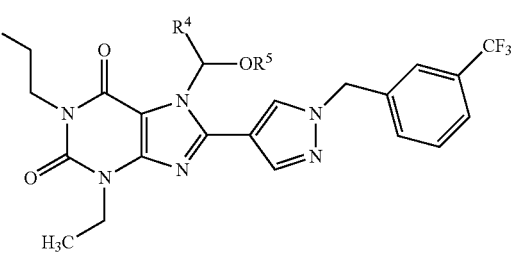

or a pharmaceutically acceptable salt or solvate thereof.

In some embodiments, $R^4$ is methyl or ethyl; $R^5$ is hydrogen, $R^7$, —C(=O)$R^7$, —C(=O)—OR$^7$, —C(=O)N($R^7$)($R^8$), —C(=O)—SR$^7$, or —P(=O)(OR$^9$)$_2$; $R^7$ is $C_1$-$C_6$alkyl, substituted or unsubstituted $C_1$-$C_6$heteroalkyl, substituted or unsubstituted monocyclic $C_3$-$C_8$cycloalkyl, substituted or unsubstituted bicyclic $C_5$-$C_{10}$cycloalkyl, substituted or unsubstituted monocyclic $C_2$-$C_8$heterocycloalkyl, substituted or unsubstituted bicyclic $C_5$-$C_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—OR$^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—OR$^{12}$, —C(=O)N($R^{12}$)($R^8$), —C(=O)—SR$^{12}$, or —P(=O)(OR$^9$)$_2$.

In some embodiments, $R^5$ is $R^7$, —C(=O)$R^7$, —C(=O)—OR$^7$, —C(=O)N($R^7$)($R^8$), —C(=O)—SR$^7$, or —P(=O)(OH)$_2$; $R^7$ is $C_1$-$C_6$alkyl, substituted or unsubstituted $C_1$-$C_6$heteroalkyl, substituted or unsubstituted cyclohexyl, substituted or unsubstituted cyclopentyl, substituted or unsubstituted bicyclo[1.1.1]pentanyl, substituted or unsubstituted bicyclo[2.2.1]heptanyl, substituted or unsubstituted bicyclo[2.2.2]octanyl, substituted or unsubstituted bicyclo[3.2.1]octanyl, substituted or unsubstituted bicyclo[3.3.0]octanyl, substituted or unsubstituted bicyclo[4.3.0]nonanyl, or substituted or unsubstituted decalinyl, substituted or unsubstituted oxetanyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH(R$^{10}$)O—R$^{11}$, —(CH$_2$CH$_2$O)$_n$—R$^{11}$, or —(C(R$^{10}$)$_2$)$_p$—OR$^{11}$; each R$^{10}$ is independently selected from hydrogen and methyl; R$^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OR$^9$)$_2$.

In some embodiments, the compound has one of the following structures:

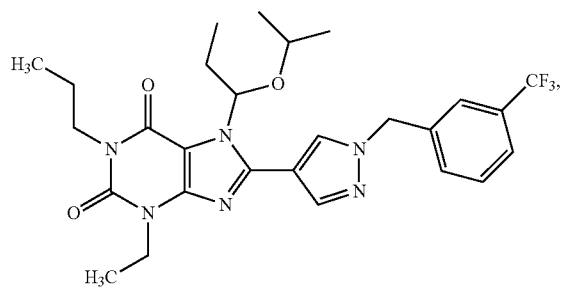

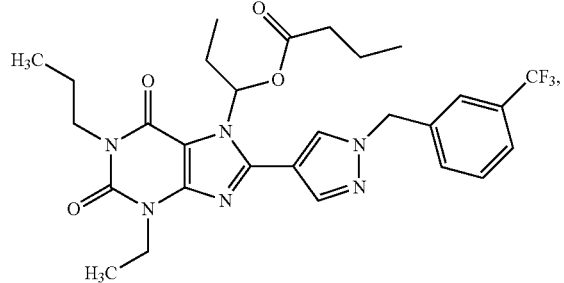

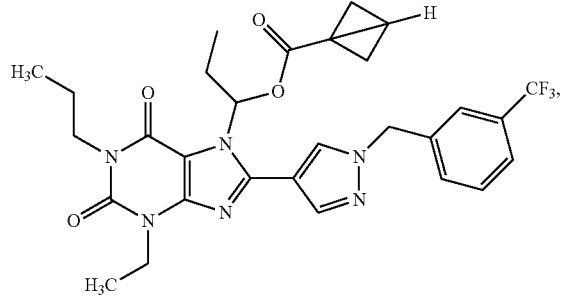

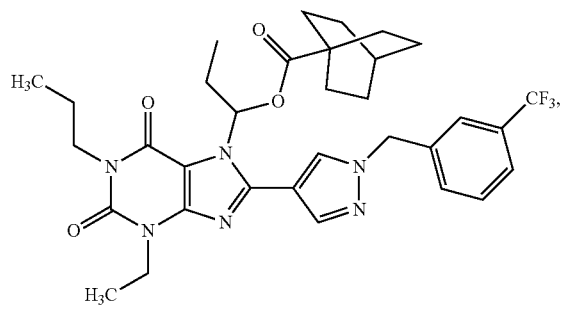

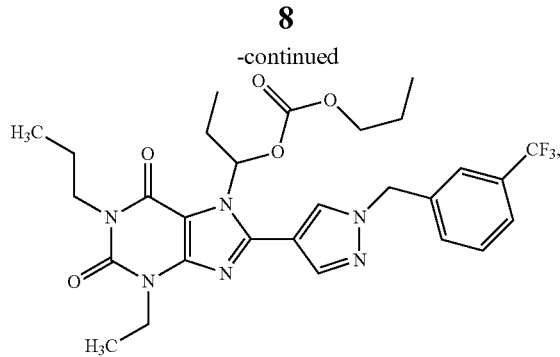

-continued

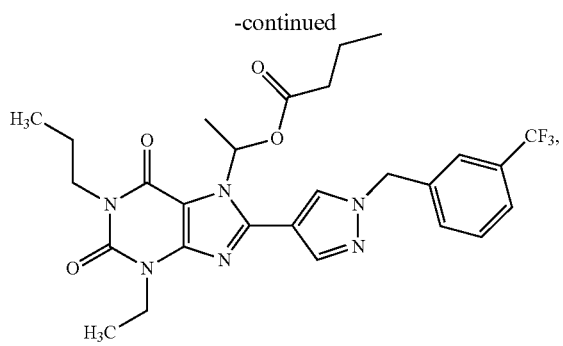

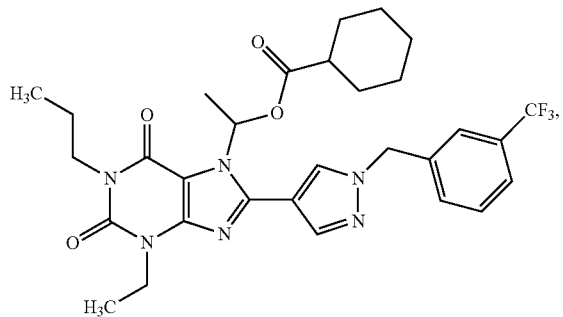

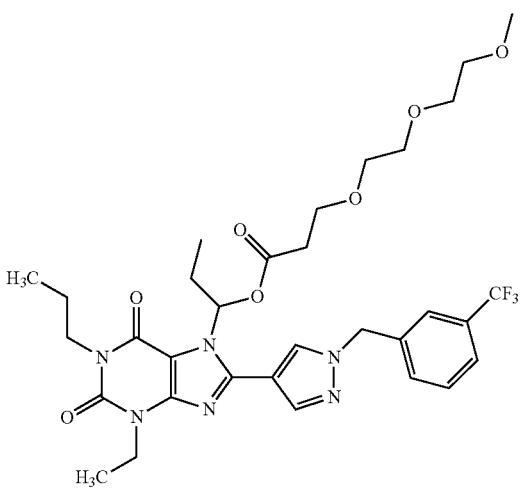

, or

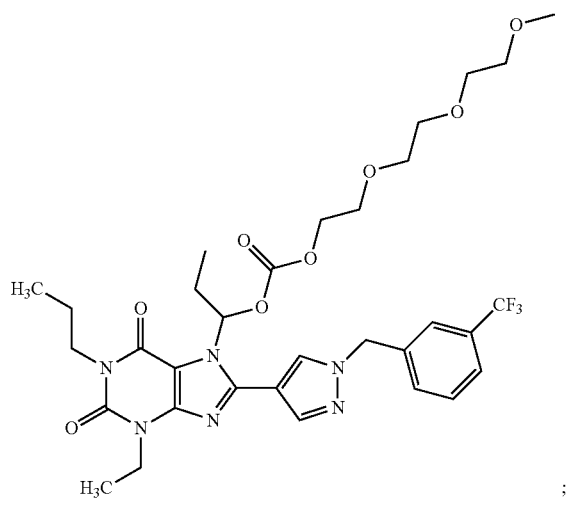

;

or a pharmaceutically acceptable salt or solvate thereof.

In some embodiments, the compound has the following structure of Formula (II):

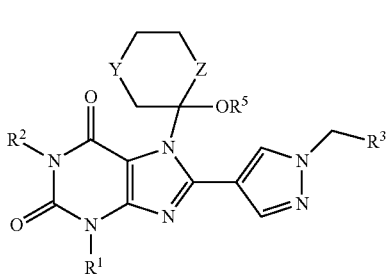

Formula (II)

wherein:

Y is selected from —CH$_2$—, O, S, —NR$^{15}$—, and —S(O)$_2$—;

Z is O or S;

or a pharmaceutically acceptable salt or solvate thereof.

In some embodiments, R$^1$ and R$^2$ are each independently selected from substituted or unsubstituted C$_1$-C$_6$alkyl; R$^3$ is selected from substituted or unsubstituted phenyl.

In some embodiments, R$^1$ is ethyl; R$^2$ is n-propyl; and R$^3$ is 3-(trifluoromethyl)phenyl.

In some embodiments, the compound has the following structure:

or a pharmaceutically acceptable salt or solvate thereof.

In some embodiments, the compound has the following structure:

or a pharmaceutically acceptable salt or solvate thereof.

In some embodiments, the compound has the following structure of Formula (IIa):

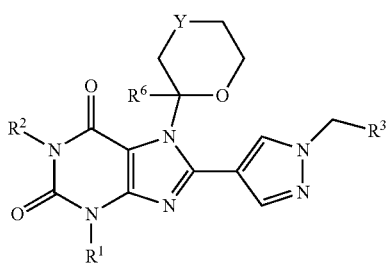

Formula (IIa)

wherein:
Y is selected from —$CH_2$—, O, S, —$NR^{15}$—, and —$S(O)_2$—;
or a pharmaceutically acceptable salt or solvate thereof.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ is ethyl; $R^2$ is n-propyl; and $R^3$ is 3-(trifluoromethyl)phenyl.

In some embodiments, the compound has the following structure:

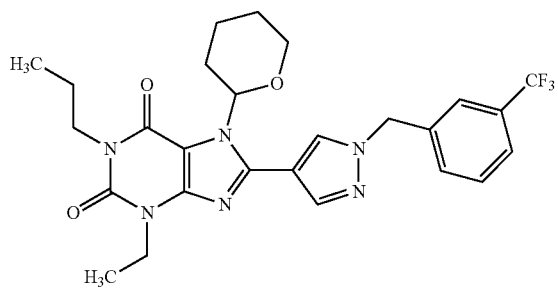 [SMILES: CCCn1c(=O)c2c(nc(-c3cnn(Cc4cccc(C(F)(F)F)c4)c3)n2C2CCCCO2)n(CC)c1=O]

or a pharmaceutically acceptable salt or solvate thereof.

In another aspect, described herein is a compound represented by Formula (B):

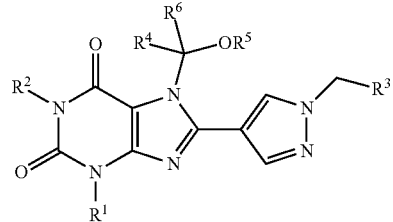

Formula (B)

or a pharmaceutically acceptable salt or solvate thereof, wherein:
$R^1$ and $R^2$ are each independently selected from hydrogen, and substituted or unsubstituted alkyl;
$R^3$ is selected from substituted or unsubstituted phenyl, and substituted or unsubstituted heteroaryl, wherein if $R^3$ is substituted then $R^3$ is substituted with one or more groups selected from halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, and substituted or unsubstituted $C_1$-$C_4$heteroalkyl;
$R^4$ is hydrogen or substituted or unsubstituted alkyl;
$R^6$ is hydrogen or substituted or unsubstituted alkyl;
or $R^4$ and $R^6$ are taken together with the carbon atom to which they are attached to form a carbonyl (C=O);
or $R^4$ and $R^6$ are taken together with the carbon atom to which they are attached to form a ring that is a substituted or unsubstituted $C_3$-$C_{10}$cycloalkyl, or substituted or unsubstituted $C_2$-$C_{10}$heterocycloalkyl, wherein if the ring is substituted then it is substituted with one or more $R^{15}$;
$R^{15}$ is hydrogen, substituted or unsubstituted alkyl, substituted or unsubstituted heteroalkyl, substituted or unsubstituted phenyl, substituted or unsubstituted heteroaryl, -alkyl-(substituted or unsubstituted phenyl), -alkyl-(substituted or unsubstituted heteroaryl), —C(=O)$R^{16}$, —C(=O)—O$R^{16}$, —C(=O)N($R^{16}$)$_2$;
each $R^{16}$ is independently selected from hydrogen and substituted or unsubstituted alkyl;
$R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C($R^{10}$)$_2$O)$_m$—$R^{11}$, —C(=O)—(C($R^{10}$)$_2$O)$_m$—$R^{11}$, —C(=O)—($CH_2CH_2O$)$_n$—$R^{11}$, —C(=O)—$R^a$ or —C(=O)—$OR^7$;
$R^a$ is substituted or unsubstituted bicyclic cycloalkyl, substituted or unsubstituted bicyclic heterocycloalkyl, substituted or unsubstituted bicyclic heteroaryl, (substituted or unsubstituted heterocycloalkyl containing at least one O atom in the ring), substituted or unsubstituted azetidinyl, substituted or unsubstituted piperidinyl, substituted or unsubstituted azapenyl, substituted or unsubstituted 5-membered heteroaryl, substituted or unsubstituted pyridin-2-yl, substituted or unsubstituted pyridin-4-yl, substituted or unsubstituted pyrimidinyl, substituted or unsubstituted pyrazinyl, substituted or unsubstituted pyridazinyl, substituted or unsubstituted triazinyl;
or $R^4$ and $R^5$ are taken together with the atoms to which they are attached to form a substituted or unsubstituted $C_2$-$C_{10}$heterocycloalkyl;
$R^7$ is substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C($R^{10}$)$_2$O)$_m$—$R^{11}$, —($CH_2CH_2O$)$_n$—$R^{11}$, or —(C($R^{10}$)$_2$)$_p$—$OR^{11}$;
each $R^9$ is independently selected from hydrogen and alkyl;
each $R^{10}$ is independently selected from hydrogen and alkyl;
$R^{11}$ is hydrogen, substituted or unsubstituted alkyl, substituted or unsubstituted heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$;
$R^{12}$ is hydrogen, substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), or -alkyl-(substituted or unsubstituted heteroaryl);
m is 1, 2, 3, 4, 5, or 6;
n is 1, 2, 3, 4, 5, or 6.
p is 1, 2, 3, 4, 5, or 6;

wherein substituted means that the referenced group is substituted with one or more additional groups individually and independently selected from halogen, —CN, —NH₂, —NH(alkyl), —N(alkyl)₂, —OH, —CO₂H, —CO₂alkyl, —C(=O)NH₂, —C(=O)NH(alkyl), —C(=O)N(alkyl)₂, —S(=O)₂NH₂, —S(=O)₂NH(alkyl), —S(=O)₂N(alkyl)₂, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone.

In some embodiments, $R^4$ is hydrogen; $R^6$ is hydrogen; $R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C(R^{10})₂O)_m—R^{11}, —C(=O)—(C(R^{10})₂O)_m—R^{11}, —C(=O)—(CH₂CH₂O)_n—R^{11}, —C(=O)—R^a or —C(=O)—OR^7.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ and $R^2$ are each independently selected from methyl, ethyl, n-propyl, iso-propyl, n-butyl, iso-butyl, tert-butyl, n-pentyl, tert-pentyl, neopentyl, isopentyl, sec-pentyl, n-hexyl, isohexyl, 3-methylpentyl, 2,3-dimethylbutyl, and neohexyl.

In some embodiments, $R^1$ is ethyl; $R^2$ is n-propyl; and $R^3$ is 3-(trifluoromethyl)phenyl.

In some embodiments, the compound has the following structure:

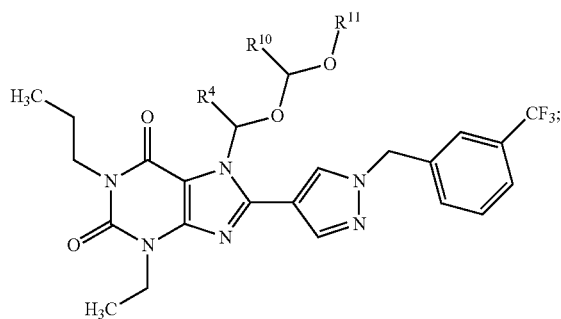

or a pharmaceutically acceptable salt or solvate thereof.

In some embodiments, $R^{11}$ is hydrogen, substituted or unsubstituted alkyl, —C(=O)R^{12}, —C(=O)—OR^{12}, —C(=O)N(R^{12})(R^8), or —P(=O)(OR^9)₂.

In some embodiments, the compound has one of the following structures:

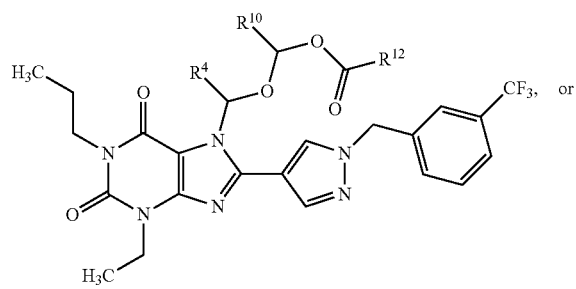

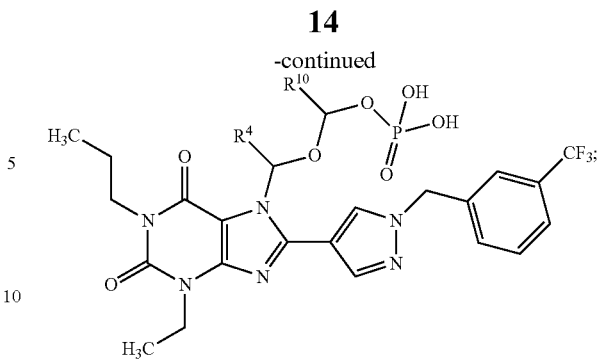

or a pharmaceutically acceptable salt or solvate thereof.

In some embodiments, the compound has one of the following structures:

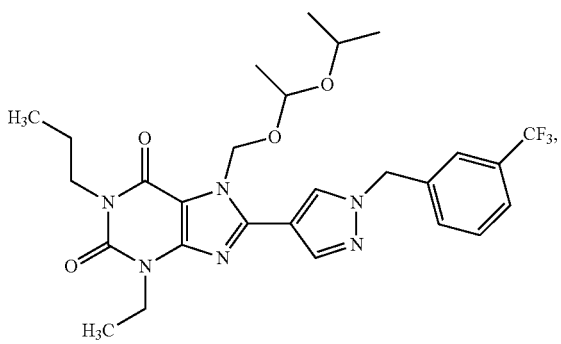

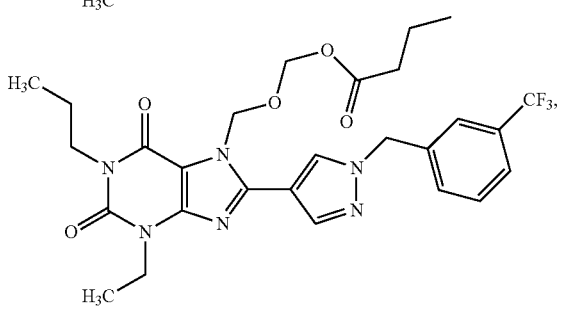

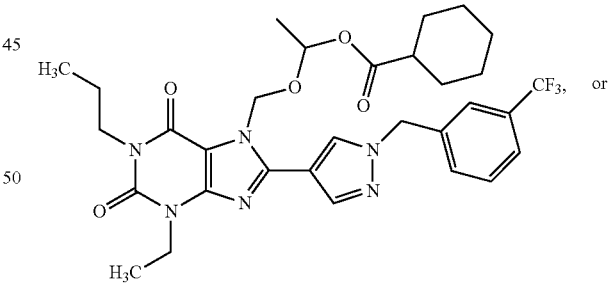

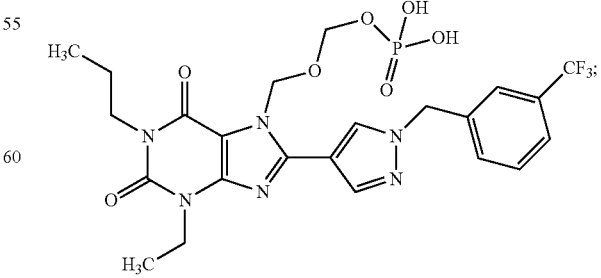

or a pharmaceutically acceptable salt or solvate thereof.

In some embodiments, $R^5$ is —C(=O)—(C($R^{10}$)$_2$O)$_m$—$R^{11}$, —C(=O)—(CH$_2$CH$_2$O)$_n$—$R^{11}$, —C(=O)—$R^a$ or —C(=O)—O$R^7$.

In some embodiments, the compound has the following structure:

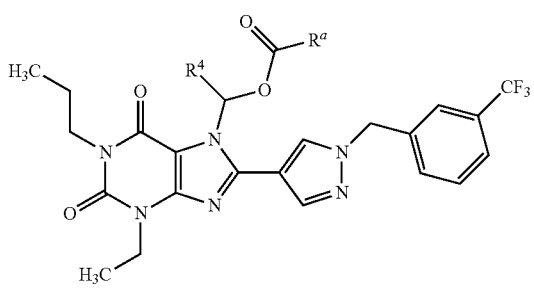

or a pharmaceutically acceptable salt or solvate thereof.

In some embodiments, $R^a$ is substituted or unsubstituted bicyclic cycloalkyl that is a fused bicyclic cycloalkyl, bridged bicyclic cycloalkyl, or spiro bicyclic cycloalkyl; or $R^a$ is substituted or unsubstituted bicyclic heterocycloalkyl that is a fused bicyclic heterocycloalkyl, bridged bicyclic heterocycloalkyl, or spiro bicyclic heterocycloalkyl; or $R^a$ is substituted or unsubstituted bicyclic heteroaryl.

In some embodiments, $R^a$ is substituted or unsubstituted bicyclo[1.1.1]pentanyl, substituted or unsubstituted bicyclo[2.2.1]heptanyl, substituted or unsubstituted bicyclo[2.2.2]octanyl, substituted or unsubstituted bicyclo[3.2.1]octanyl, substituted or unsubstituted bicyclo[3.3.0]octanyl, substituted or unsubstituted bicyclo[4.3.0]nonanyl, or substituted or unsubstituted decalinyl.

In some embodiments, the compound has one of the following structures:

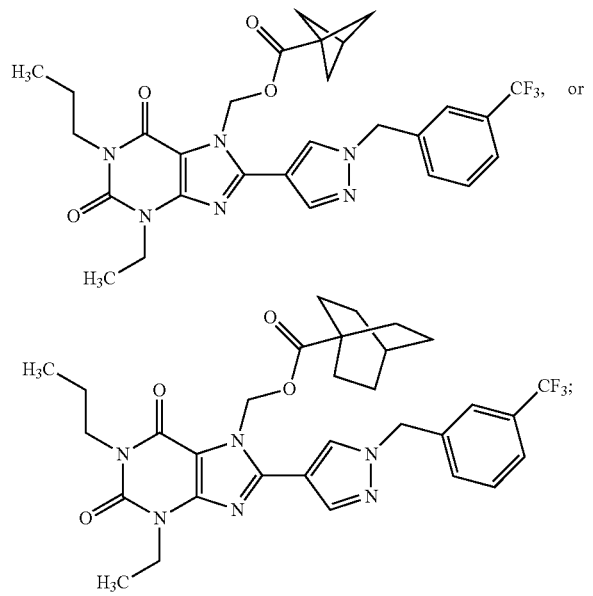

or a pharmaceutically acceptable salt or solvate thereof.

In some embodiments, $R^a$ is substituted or unsubstituted heterocycloalkyl containing at least one O atom in the ring, substituted or unsubstituted azetidinyl, substituted or unsubstituted piperidinyl, substituted or unsubstituted azapenyl, substituted or unsubstituted 5-membered heteroaryl, substituted or unsubstituted pyridin-2-yl, substituted or unsubstituted pyridin-4-yl, substituted or unsubstituted pyrimidinyl, substituted or unsubstituted pyrazinyl, substituted or unsubstituted pyridazinyl, substituted or unsubstituted triazinyl.

In some embodiments, $R^a$ is a substituted or unsubstituted heterocycloalkyl containing at least one O atom in the ring that is substituted or unsubstituted tetrahydrofuranyl, substituted or unsubstituted dihydrofuranyl, substituted or unsubstituted oxazolidinonyl, substituted or unsubstituted tetrahydropyranyl, substituted or unsubstituted dihydropyranyl, substituted or unsubstituted tetrahydrothiopyranyl, substituted or unsubstituted morpholinyl, substituted or unsubstituted oxetanyl, substituted or unsubstituted oxepanyl, substituted or unsubstituted oxazepinyl, or substituted or unsubstituted dioxanyl.

In some embodiments, $R^a$ is a substituted or unsubstituted 5-membered heteroaryl that is substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, or substituted or unsubstituted thiadiazolyl, In some embodiments, the compound has one of the following structures:

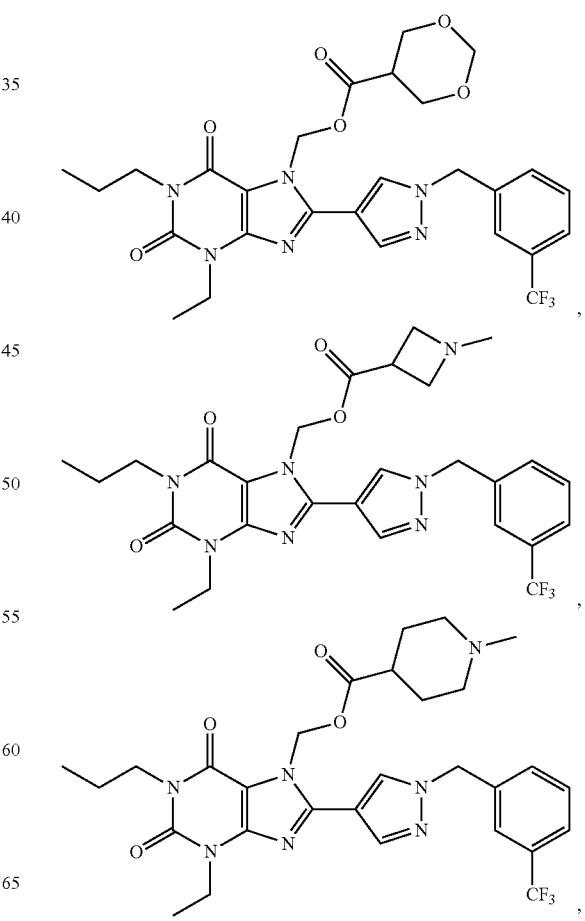

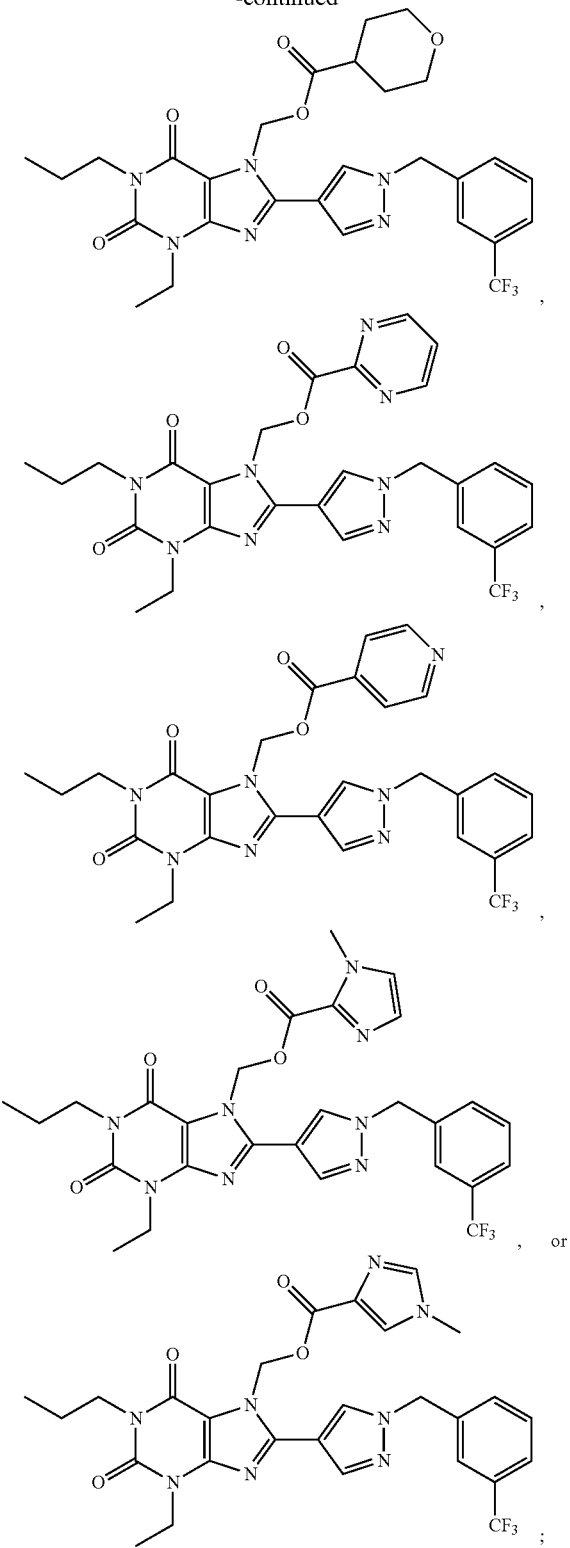

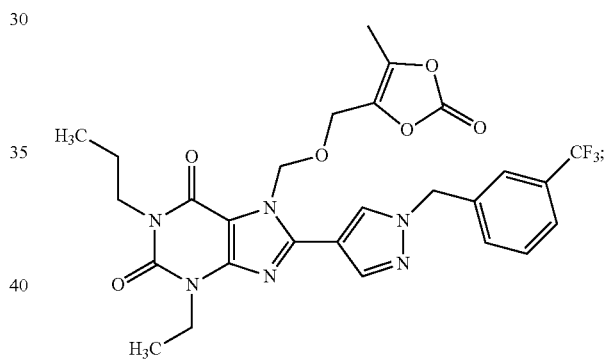

or a pharmaceutically acceptable salt or solvate thereof.

In some embodiments, $R^1$ is ethyl; $R^2$ is n-propyl; $R^3$ is 3-(trifluoromethyl)phenyl; $R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl).

In some embodiments, the compound has the following structure:

or a pharmaceutically acceptable salt or solvate thereof.

Also described herein is a pharmaceutical formulation, comprising a compound of any one of the compounds disclosed herein, or a pharmaceutically acceptable salt or solvate thereof; and at least one pharmaceutically acceptable excipient.

In some embodiments, the pharmaceutical composition is formulated for administration to a mammal by oral administration, intravenous administration, or subcutaneous administration.

In some embodiments, the pharmaceutical composition is in the form of a tablet, a pill, a capsule, a liquid, a suspension, a dispersion, a solution, or an emulsion.

In one aspect, described herein is a method of modulating the $A_{2B}$ adenosine receptor in a mammal comprising administering to the mammal a compound described herein, or any pharmaceutically acceptable salt or solvate thereof.

In another aspect, described herein is a method of treating a disease or disorder in a mammal comprising administering to the mammal in need thereof a therapeutically effective amount of a compound described herein, or a pharmaceutically acceptable salt or solvate thereof, wherein the condition is selected from the group consisting of cardiovascuor a pharmaceutically acceptable salt or solvate thereof.

In some embodiments, $R^1$ is ethyl; $R^2$ is n-propyl; $R^3$ is 3-(trifluoromethyl)phenyl; $R^5$ is —C(=O)—(C($R^{10}$)$_2$O)$_m$—$R^{11}$, —C(=O)—(CH$_2$CH$_2$O)$_n$—$R^{11}$, or —C(=O)—O$R^7$.

In some embodiments, the compound has one of the following structures:

lar diseases, fibrosis, neurological disorders, type I hypersensitivity disorders, chronic and acute liver diseases, lung diseases, renal diseases, diabetes, obesity, and cancer. In some embodiments, the disease or disorder is cancer.

In some embodiments, the subject is human.

In any of the aforementioned aspects are further embodiments in which an effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal.

In any of the aforementioned aspects are further embodiments comprising single administrations of an effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

Any combination of the groups described above for the various variables is contemplated herein. Throughout the specification, groups and substituents thereof are chosen by one skilled in the field to provide stable moieties and compounds.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Disclosed herein are compounds, compositions, formulations, and methods related to $A_{2B}$ adenosine receptor antagonists. For example, the compounds, compositions, and/or formulations disclosed herein can be used in a method of treating a condition in a subject in need thereof. The condition can be cardiovascular diseases, chronic and acute liver disease, lung disease, renal disease, diabetes, obesity, and/or cancer.

8-(1-(3-(Trifluoromethyl)benzyl)-1H-pyrazol-4-yl)-3-ethyl-1-propyl-1H-purine-2,6(3H,7H)-dione (Compound 1) is an $A_{2B}$ adenosine receptor antagonist, which is a xanthine unsubstituted at 7-position. It can be relatively insoluble in aqueous media and difficult to formulate using conventional pharmaceutical excipients, and thus can be difficult to formulate in a manner that provides reproducible plasma levels of the compound undergoing evaluation in mammals, in particular humans. Accordingly, new prodrugs of the $A_{2B}$ adenosine receptor antagonist can be developed to improve the formulation, pharmacokinetic profile, and/or bioavailability the $A_{2B}$ adenosine receptor antagonist.

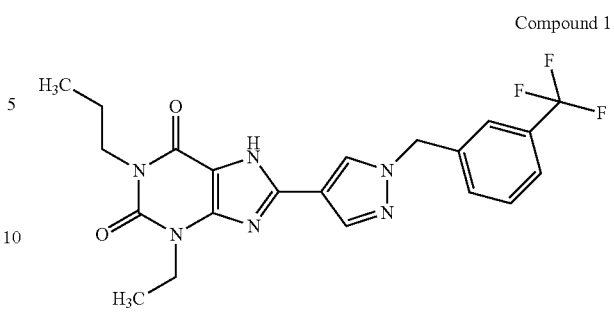

Compound 1

In some cases, prodrugs can be hydrolyzed by esterase (e.g., in gastrointestinal tract and/or in blood) and converted into Compound 1 in an aqueous solution. In some cases, acid labile prodrugs can be converted into Compound 1 in an acidic environment (e.g., in the stomach). In some cases, prodrugs, which are stable in the acidic environment and/or stable against hydrolysis by esterase, may not be a good prodrug candidate for Compound 1.

In one aspect, the compounds, compositions, and/or formulations disclosed herein can be used to treat cancer. On endothelial cells, for example, adenosine can bind to the $A_{2B}$ adenosine receptors, thereby stimulating angiogenesis. On T cells, $A_{2B}$ adenosine receptor stimulation can lead to type I protein kinase A (PKA) isoform activation that can hamper T cell activation through inhibition of T-cell antigen receptor (TCR) proximal kinases Lck and Fyn. The pro-metastatic Fra-1 transcription factor can also induce $A_{2B}$ adenosine receptor expression on cancer cells, and thus $A_{2B}$ adenosine receptor antagonist can inhibit metastasis of Fra-1-expressing cells. $A_{2B}$ adenosine receptor signaling activation can impair antigen presentation and can also inhibit signal transducer and activator of transcription 1 (STAT1) activation. The diversity of signaling and biological activities of $A_{2B}$ adenosine receptor can render it an attractive cancer target to promote anti-tumor immunity and suppress tumor cell metastasis.

In another aspect, the compounds, compositions, and/or formulations disclosed herein can be used to treat fibrosis. A commonly ingested adenosine receptor antagonist, caffeine, can block the development of hepatic fibrosis, an effect that may explain the epidemiologic finding that coffee drinking, in a dose-dependent fashion, can reduce the likelihood of death from liver disease. $A_{2B}$ adenosine receptors can also play a role in the pathogenesis of interstitial fibrosis. Adenosine, acting at $A_{2B}$ adenosine receptors, can stimulate hepatic stellate cell-mediated fibrosis of the liver by increasing production of collagen I and III via two distinct mitogen-activated protein kinase (MAPK)-dependent pathways, extracellular signal-regulated kinase 1/2 (ERK1/2) and p38MAPK, respectively. Over-activation of $A_{2B}$ adenosine receptors can be involved in liver, lung and heart fibrosis. Accordingly, $A_{2B}$ adenosine receptors may be a good therapeutic target for fibrosis of the liver, lungs, heart, and/or skin.

In another aspect, the compounds, compositions, and/or formulations disclosed herein can be used to treat diabetes and/or obesity. Insensitivity to insulin can exacerbate diabetes and/or obesity. Insulin sensitivity can be decreased by the interaction of adenosine with $A_{2B}$ adenosine receptors. Thus, blocking the $A_{2B}$ adenosine receptors of individuals with diabetes and/or obesity can benefit patients with these disorders.

In another aspect, the compounds, compositions, and/or formulations disclosed herein can be used to treat neurological disorders, such as dementias and Alzheimer's disease. Adenosine acting at $A_{2B}$ adenosine receptors can overstimulate cerebral interleukin 6 (IL-6), a cytokine associated with dementias and Alzheimer's disease. Inhibiting the binding of adenosine to $A_{2B}$ adenosine receptors can therefore mitigate those neurological disorders that are produced by IL-6.

In another aspect, the compounds, compositions, and/or formulations disclosed herein can be used to treat type I hypersensitivity disorders, such as chronic obstructive pulmonary disease (COPD), asthma, hay fever, and atopic eczema. These type I hypersensitivity disorders can be stimulated by mast cells binding to $A_{2B}$ adenosine receptors. Therefore, blocking $A_{2B}$ adenosine receptors can provide a therapeutic benefit against such disorders.

Definitions

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

The section headings used herein are for organizational purposes only and are not to be construed as limiting the subject matter described.

The details of one or more inventive embodiments are set forth in the accompanying drawings, the claims, and the description herein. Other features, objects, and advantages of the inventive embodiments disclosed and contemplated herein can be combined with any other embodiment unless explicitly excluded.

The open terms for example "contain," "containing," "include," "including," and the like mean comprising, and are not limiting.

The singular forms "a", "an", and "the" are used herein to include plural references unless the context clearly dictates otherwise.

Unless otherwise indicated, some embodiments herein contemplate numerical ranges. When a numerical range is provided, unless otherwise indicated, the range can include the range endpoints. Unless otherwise indicated, numerical ranges can include all values and subranges therein as if explicitly written out.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

The term "prodrug" refers to any compound that becomes an active form of a drug (e.g., Compound I) when administered to a subject, e.g., upon metabolic processing of the prodrug.

Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of compound 1 described herein include, but are not limited to, compounds where the nitrogen atom is incorporated into an alkyl carbamate, (acyloxy)alkyl carbamate, acyloxyalkyl ester, alkoxycarbonyloxyalkyl ester, alkyl ester, aryl ester, phosphate ester, sugar ester, ether, N-acyloxyalkoxycarbonyl, N-acyloxyakyl. dihydropyridinepyridinium salt system (redox systems), (phosphoryloxy)methyl carbamate, (acyloxy)alkyl carbamate, and the like.

In some embodiments, prodrugs of Compound 1 are formed by N-acyloxyalkylation, N-hydroxyalkylation, N-(phosphoryloxy)alkylation, N-acyloxyalkylation, N-hydroxyalkylation, N-(phosphoryloxy)alkylation, N-acylation (amides and carbamates), N-(oxodioxolenyl)methylation, and the like.

The term "pharmaceutically acceptable" component is one that is suitable for use with humans and/or animals without undue adverse side effects (such as toxicity, irritation, and allergic response) commensurate with a reasonable benefit/risk ratio.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation and/or amelioration of the signs, symptoms, or causes of a disease, slowing of disease progression, or any other desired alteration of a biological system. For example, an "effective amount" for therapeutic uses is the amount of compound as disclosed herein required to provide a clinically significant decrease in disease symptoms. An appropriate "effective" amount in any individual case is optionally determined using techniques, such as a dose escalation study.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of additional symptoms of the disease, such as cancer.

The term "subject" refers to a mammal that has been or will be the object of treatment, observation or experiment.

The term "mammal" is intended to have its standard meaning, and encompasses for example humans, dogs, cats, sheep, and cows. The methods described herein can be useful in both human therapy and veterinary applications. In some embodiments, the mammal is a human.

The term "derivative" can be used interchangeably with the term "analog." Compound 1 can be a derivative or analog if 1, 2, 3, 4, or 5 atoms of compound 1 is replaced by another atom or a functional group (e.g., amino, halo, substituted or unsubstituted alkyl, substituted or unsubstituted aryl, substituted or unsubstituted arylalkyl, or substituted or unsubstituted cycloalkyl) to form the compounds of the disclosure.

The term "solvate" can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Thrich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

The term "salt" can include, but are not limited to, salts that retain one or more of the activities and properties of the free acids and bases and that are not undesirable. Illustrative examples of salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Unless otherwise indicated, whenever there is a stereocenter in a structure disclosed or illustrated herein, the stereocenter can be R or S in each case.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In another embodiment, the compounds described herein are labeled isotopically (e.g. with a radioisotope) or by another other means.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}$H, $^{3}$H, $^{13}$C, $^{14}$C, $^{15}$N, $^{18}$O, $^{17}$O, $^{35}$S, $^{18}$F, $^{36}$Cl. An one aspect, isotopically-labeled compounds described herein, for example those into which radioactive isotopes such as $^{3}$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

The term "amino" refers to functional groups that contain a basic nitrogen atom with a lone pair. For example, amino can include the radical

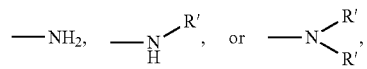

wherein each R' is independently H, halo, alkyl, aryl, arylalkyl, cycloalkyl, or acyl.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Alternatively, an alkyl includes, but is not limited to, methyl, ethyl, propan-1-yl, propan-2-yl, butan-1-yl, butan-2-yl, 2-methyl-propan-1-yl, 2-methyl-propan-2-yl, and the like. Typical alkyl groups include, but are in no way limited to, methyl, ethyl, propyl, isopropyl, butyl, isobutyl, sec-butyl, tertiary butyl, pentyl, neopentyl, or hexyl.

The term "lower alkyl" can refer to a monoradical branched or unbranched saturated hydrocarbon chains having 1, 2, 3, 4, 5, or 6 carbon atoms, such as methyl, ethyl, n-propyl, iso-propyl, n-butyl, iso-butyl, t-butyl, n-hexyl, and the like.

In some embodiments, when an alkyl is unsaturated, then the alkyl is an alkenyl or alkynyl.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$. Alternatively, an alkenyl includes, but is not limited to, ethenyl, prop-1-en-1-yl, prop-1-en-2-yl, prop-2-en-1-yl (allyl), but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, and the like.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH. Alternatively, an alkynyl includes, but is not limited to, ethynyl, prop-1-yn-1-yl, prop-2-yn-1-yl, but-1-yn-1-yl, but-1-yn-3-yl, but-3-yn-1-yl; and the like.

An "alkoxy" group refers to a (alkyl)O— group, where alkyl is as defined herein.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

An "fluoroalkoxy" group refers to a (fluoroalkyl)O— group, where fluoroalkyl is as defined herein.

The term "halo" or "halogen" refers to fluorine, chlorine, bromine or iodine.

The term "heteroalkyl" refers to an alkyl group in which one or more skeletal atoms of the alkyl are selected from an atom other than carbon, e.g., oxygen, nitrogen (e.g. —NH—, —N(alkyl)-), sulfur (—S—, —S(O)—, —S(O)$_2$—), phosporus (—PH—, —P(O)$_2$—), or combinations thereof (e.g. —O—P(O)$_2$—). A heteroalkyl is attached to the rest of the molecule at a carbon atom of the heteroalkyl. In one aspect, a heteroalkyl is a $C_1$-$C_6$heteroalkyl. In some embodiments, As used herein, the term "aryl" refers to an aromatic ring wherein each of the atoms forming the ring is a carbon atom. Typical aryl groups include, but are not limited to, phenyl, naphthyl, fluorenyl, indanyl, indenyl, and the like. In one some embodiments, aryl is phenyl or a naphthyl. In some embodiments, an aryl is a phenyl. In some embodiments, an aryl is a $C_6$-$C_{10}$aryl.

The terms "heteroaryl" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

The term "arylalkyl" refers to an alkyl that is substituted with an aryl group. Typical arylalkyl groups include, but are not limited to, benzyl, 2-phenylethan-1-yl, naphthylmethyl, 2-naphthylethan-1-yl, and the like.

The term "heteroarylalkyl" refers to an alkyl that is substituted with a heteroaryl group.

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are monocyclic, bicyclic (spirocyclic, fused or bridged), or polycyclic. Cycloalkyl groups include groups having from 3 to 10 ring atoms (i.e. ($C_3$-$C_{10}$) cycloalkyl). In some embodiments, a cycloalkyl is a ($C_3$-$C_6$) cycloalkyl. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1]pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

In some embodiments, a cycloalkyl is partially unsaturated ("cycloalkenyl", including but not limited to, cyclobut-1-en-1-yl, cyclobut-1-en-3-yl, cyclobuta-1,3-dien-1-yl, and the like).

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "acyl" can refer to —C(O)R', in which R' is hydrogen, alkyl, substituted alkyl, arylalkyl, substituted arylalkyl, cycloalkyl, substituted cycloalkyl, aryl, or substituted aryl.

The term "substituted" can refer to a group in which one or more hydrogen atoms are each independently replaced with the same or different substituent(s). Typical substituents include, but are The term "substituted" or "optionally substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halo, alkyl, heteroalkyl, aryl, heteroaryl, arylalkyl, heteroarylalkyl, cycloalkyl, heterocycloalkyl, or acyl. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

Prodrugs

In one aspect, described herein is a compound represented by Formula (A):

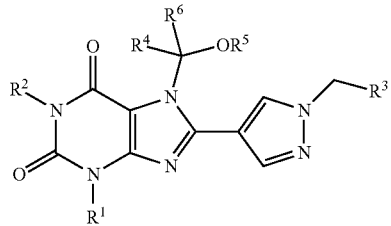

Formula (A)

or a pharmaceutically acceptable salt or solvate thereof, wherein:
$R^1$ and $R^2$ are each independently selected from hydrogen, and substituted or unsubstituted alkyl;
$R^3$ is selected from substituted or unsubstituted phenyl, and substituted or unsubstituted heteroaryl, wherein if $R^3$ is substituted then $R^3$ is substituted with one or more groups selected from halogen, —CN, —OH, C$_1$-C$_4$alkyl, C$_2$-C$_4$alkenyl, C$_2$-C$_4$alkynyl, C$_1$-C$_4$alkoxy, C$_1$-C$_4$fluoroalkyl, C$_1$-C$_4$fluoroalkoxy, and substituted or unsubstituted C$_1$-C$_4$heteroalkyl;
$R^4$ is substituted or unsubstituted alkyl;
$R^6$ is hydrogen or substituted or unsubstituted alkyl;
or $R^4$ and $R^6$ are taken together with the carbon atom to which they are attached to form a carbonyl (C=O);
or $R^4$ and $R^6$ are taken together with the carbon atom to which they are attached to form a ring that is a substituted or unsubstituted C$_3$-C$_{10}$cycloalkyl, or substituted or unsubstituted C$_2$-C$_{10}$heterocycloalkyl, wherein if the ring is substituted then it is substituted with one or more $R^{15}$;
$R^{15}$ is hydrogen, substituted or unsubstituted alkyl, substituted or unsubstituted heteroalkyl, substituted or unsubstituted phenyl, substituted or unsubstituted heteroaryl, -alkyl-(substituted or unsubstituted phenyl), -alkyl-(substituted or unsubstituted heteroaryl), —C(=O)R$^{16}$, —C(=O)—OR$^{16}$, —C(=O)N(R$^{16}$)$_2$;
each $R^{16}$ is independently selected from hydrogen and substituted or unsubstituted alkyl;
$R^5$ is hydrogen, $R^7$, —C(=O)R$^7$, —C(=O)—OR$^7$, —C(=O)N(R$^7$)(R$^8$), —C(=O)—SR$^7$, or —P(=O)(OR$^9$)$_2$;
or $R^4$ and $R^5$ are taken together with the atoms to which they are attached to form a substituted or unsubstituted C$_2$-C$_{10}$heterocycloalkyl;
$R^7$ is substituted or unsubstituted alkyl, substituted or unsubstituted heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C(R$^{10}$)$_2$O)$_m$—R$^{11}$, —(CH$_2$CH$_2$O)$_n$—R$^{11}$, or —(C(R$^{10}$)$_2$)$_p$—OR$^{11}$;
$R^8$ is hydrogen or alkyl;
or $R^7$ and $R^8$ are taken together with the nitrogen atom to which they are attached to form a substituted or unsubstituted C$_2$-C$_{10}$heterocycloalkyl;
each $R^9$ is independently selected from hydrogen and alkyl;
each $R^{10}$ is independently selected from hydrogen and alkyl;
$R^{11}$ is hydrogen, substituted or unsubstituted alkyl, substituted or unsubstituted heteroalkyl, substituted or unsubstituted C$_2$-C$_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OR$^9$)$_2$;
$R^{12}$ is hydrogen, substituted or unsubstituted alkyl, substituted or unsubstituted heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted heteroaryl, -alkyl-(substituted or unsubstituted phenyl), or -alkyl-(substituted or unsubstituted heteroaryl);
m is 1, 2, 3, 4, 5, or 6;
n is 1, 2, 3, 4, 5, or 6;
p is 1, 2, 3, 4, 5, or 6;
wherein substituted means that the referenced group is substituted with one or more additional groups individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone.

In some embodiments, m is 1, 2, 3, 4, 5, or 6. In some embodiments, m is 1, 2, 3, 4, or 5. In some embodiments, m is 1, 2, 3, or 4. In some embodiments, m is 1, 2, or 3. In some embodiments, m is 1 or 2. In some embodiments, m is 1. In some embodiments, m is 2, 3, 4, 5, or 6.

In some embodiments, n is 1, 2, 3, 4, 5, or 6. In some embodiments, n is 1, 2, 3, 4, or 5. In some embodiments, n is 1, 2, 3, or 4. In some embodiments, n is 1, 2, or 3. In some embodiments, n is 1 or 2. In some embodiments, n is 2 or 3. In some embodiments, n is 1. In some embodiments, n is 2. In some embodiments, n is 3. In some embodiments, n is 2, 3, 4, 5, or 6.

In some embodiments, p is 1, 2, 3, 4, 5, or 6. In some embodiments, p is 1, 2, 3, 4, or 5. In some embodiments, p is 1, 2, 3, or 4. In some embodiments, p is 1, 2, or 3. In some embodiments, p is 1 or 2. In some embodiments, p is 1. In some embodiments, p is 2, 3, 4, 5, or 6.

In some embodiments, $R^1$ and $R^2$ are each independently selected from substituted or unsubstituted C$_1$-C$_6$alkyl. In some embodiments, $R^1$ and $R^2$ are each independently selected from unsubstituted C$_1$-C$_3$alkyl. In some embodiments, $R^1$ is ethyl. In some embodiments, $R^2$ is n-propyl. In some embodiments, $R^1$ is ethyl and $R^2$ is n-propyl.

In some embodiments, $R^3$ is selected from substituted or unsubstituted phenyl. In some embodiments, $R^3$ is substituted phenyl. In some embodiments, $R^3$ is phenyl substituted by one or more groups independently selected from halogen, C$_1$-C$_4$ alkyl, or C$_1$-C$_4$ fluoroalkyl. In some embodiments, $R^3$ is phenyl substituted by one or more groups independently selected from C$_1$-C$_4$ fluoroalkyl. In some embodiments, $R^3$ is selected from phenyl substituted with one, two, or three —CF$_3$ substituents. In some embodiments, $R^3$ is selected from phenyl substituted with one —CF$_3$ substituent. In some embodiments, $R^3$ is

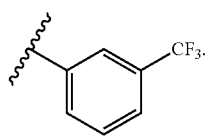 [SMILES: *c1cccc(C(F)(F)F)c1]

In some embodiments, $R^1$ and $R^2$ are each independently selected from substituted or unsubstituted C$_1$-C$_6$alkyl; $R^3$ is selected from substituted or unsubstituted phenyl.

In some embodiments, $R^1$ and $R^2$ are each independently selected from methyl, ethyl, n-propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, and neohexyl.

In some embodiments, $R^1$ is ethyl; $R^2$ is n-propyl; and $R^3$ is 3-(trifluoromethyl)phenyl.

In some embodiments, $R^4$ is C$_1$-C$_6$alkyl and $R^6$ is selected from hydrogen, and C$_1$-C$_6$alkyl. In some embodiments, $R^4$ and $R^6$ are taken together with the carbon atom to which they are attached to form a carbonyl (C=O).

In some embodiments, $R^4$ is methyl, ethyl, or n-propyl and $R^6$ is selected from hydrogen, methyl, ethyl, and n-propyl. In some embodiments, $R^4$ is methyl or ethyl. In some embodiments, $R^6$ is hydrogen. In some embodiments, $R^4$ is methyl or ethyl; and $R^6$ is hydrogen.

In some embodiments, $R^5$ is $R^7$. In some embodiments, $R^5$ is —(C=O)$R^7$. In some embodiments, $R^5$ is —(C=O)—O$R^7$.

In some embodiments, $R^5$ is $R^7$; $R^7$ is C$_1$-C$_6$alkyl, substituted or unsubstituted C$_1$-C$_6$heteroalkyl, substituted or unsubstituted monocyclic C$_3$-C$_8$cycloalkyl, substituted or unsubstituted bicyclic C$_5$-C$_{10}$cycloalkyl, substituted or unsubstituted monocyclic C$_2$-C$_8$heterocycloalkyl, substituted or unsubstituted bicyclic C$_5$-C$_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH($R^{10}$)O—$R^{11}$, —(CH$_2$CH$_2$O)$_n$$R^{11}$, or —(C($R^{10}$)$_2$)$_p$—O$R^{11}$; each $R^{10}$ is independently selected from hydrogen and methyl; $R^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, $R^7$ is C$_1$-C$_6$alkyl, substituted or unsubstituted C$_1$-C$_6$heteroalkyl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH($R^{10}$)O—$R^{11}$, or —(CH$_2$CH$_2$O)$_n$$R^{11}$; $R^{10}$ is hydrogen and methyl; $R^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(OH)$_2$.

In some embodiments, $R^7$ is C$_1$-C$_6$alkyl. In some embodiments, $R^7$ is methyl, ethyl, n-propyl, isopropyl, n-butyl, or n-pentyl.

In some embodiments, $R^7$ is —CH($R^{10}$)O—$R^{11}$ wherein $R^{11}$ is —C(=O)$R^{12}$, and wherein $R^{12}$ is unsubstituted alkyl, unsubstituted C$_3$-C$_{10}$cycloalkyl. In some embodiments, $R^{12}$ is methyl, ethyl, n-propyl, n-butyl, or n-pentyl. In some embodiments, $R^{12}$ is cyclopropyl, cyclobutyl, cyclopentyl, or cyclohexyl.

In some embodiments, $R^7$ is —CH($R^{10}$)O—$R^{11}$, wherein $R^{11}$ is —P(=O)(O$R^9$)$_2$. In some embodiments, $R^9$ is hydrogen.

In some embodiments, $R^7$ is —(CH$_2$CH$_2$O)$_n$$R^{11}$, wherein $R^{11}$ is unsubstituted alkyl. In some embodiments, $R^{11}$ is methyl, ethyl, n-propyl, n-butyl, or n-pentyl.

In some embodiments, $R^7$ is —CH$_2$-(substituted or unsubstituted C$_2$-C$_8$heterocycloalkyl). In some embodiments, $R^7$ is —CH$_2$-(substituted C$_5$-C$_6$heterocycloalkyl). In some embodiments, $R^7$ is

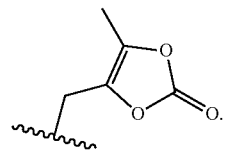 [SMILES: *Cc1oc(=O)oc1C]

In some embodiments, $R^7$ is substituted or unsubstituted C$_3$-C$_{10}$ cycloalkyl. In some embodiments, $R^7$ is unsubstituted C$_3$-C$_{10}$ cycloalkyl. In some embodiments, $R^7$ is monocyclic C$_3$—Cm cycloalkyl. In some embodiments, $R^7$ is cyclopropyl, cyclobutyl, cyclopentyl, or cyclohexyl. In some embodiments, $R^7$ is cyclohexyl. In some embodiments, $R^7$ is spirocyclic $C_3$-$C_{10}$ cycloalkyl. In some embodiments, $R^7$ is adamantyl.

In some embodiments, $R^4$ is methyl or ethyl; $R^5$ is hydrogen, $R^7$, —C(=O)$R^7$, —C(=O)—O$R^7$, —C(=O)N($R^7$)($R^8$), —C(=O)—S$R^7$, or —P(=O)(O$R^9$)$_2$; $R^7$ is $C_1$-$C_6$alkyl, substituted or unsubstituted $C_1$-$C_6$heteroalkyl, substituted or unsubstituted monocyclic $C_3$-$C_8$cycloalkyl, substituted or unsubstituted bicyclic $C_5$-$C_{10}$cycloalkyl, substituted or unsubstituted monocyclic $C_2$-$C_8$heterocycloalkyl, substituted or unsubstituted bicyclic $C_5$-$C_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—O$R^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, $R^5$ is $R^7$, —C(=O)$R^7$, —C(=O)—O$R^7$, —C(=O)N($R^7$)($R^8$), —C(=O)—S$R^7$, or —P(=O)(OH)$_2$; $R^7$ is $C_1$-$C_6$alkyl, substituted or unsubstituted $C_1$-$C_6$heteroalkyl, substituted or unsubstituted cyclohexyl, substituted or unsubstituted cyclopentyl, substituted or unsubstituted bicyclo[1.1.1]pentanyl, substituted or unsubstituted bicyclo[2.2.1]heptanyl, substituted or unsubstituted bicyclo[2.2.2]octanyl, substituted or unsubstituted bicyclo[3.2.1]octanyl, substituted or unsubstituted bicyclo[3.3.0]octanyl, substituted or unsubstituted bicyclo[4.3.0]nonanyl, or substituted or unsubstituted decalinyl, substituted or unsubstituted oxetanyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—O$R^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, $R^5$ is $R^7$, wherein $R^7$ is $C_1$-$C_6$alkyl. In some embodiments, $R^7$ is methyl, ethyl, n-propyl, isopropyl, n-butyl, or n-pentyl.

In some embodiments, $R^5$ is —C(=O)$R^7$, wherein $R^7$ is $C_1$-$C_6$alkyl or unsubstituted $C_3$-$C_{10}$cycloalkyl. In some embodiments, $R^7$ is methyl, ethyl, n-propyl, isopropyl, n-butyl, or n-pentyl. In some embodiments, $R^7$ is cyclopropyl, cyclobutyl, cyclopentyl, cyclohexyl, bicyclo[1.1.1]pentanyl, s bicyclo[2.2.1]heptanyl, bicyclo[2.2.2]octanyl, bicyclo[3.2.1]octanyl, bicyclo[3.3.0]octanyl, or bicyclo[4.3.0]nonanyl.

In some embodiments, $R^5$ is —C(=O)—O$R^7$, wherein $R^7$ is $C_1$-$C_6$alkyl or unsubstituted $C_3$-$C_{10}$cycloalkyl. In some embodiments, $R^7$ is methyl, ethyl, n-propyl, isopropyl, n-butyl, or n-pentyl. In some embodiments, $R^7$ is cyclopropyl, cyclobutyl, cyclopentyl, cyclohexyl, bicyclo[1.1.1]pentanyl, s bicyclo[2.2.1]heptanyl, bicyclo[2.2.2]octanyl, bicyclo[3.2.1]octanyl, bicyclo[3.3.0]octanyl, or bicyclo[4.3.0]nonanyl.

In some embodiments, the compound has the following structure of Formula (III):

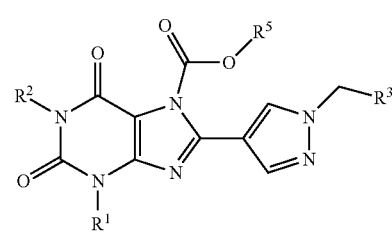

Formula (III)

or a pharmaceutically acceptable salt or solvate thereof.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ and $R^2$ are each independently selected from methyl, ethyl, n-propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, and neohexyl.

In some embodiments, $R^1$ is ethyl; $R^2$ is n-propyl; and $R^3$ is 3-(trifluoromethyl)phenyl.

In some embodiments, the compound has the following structure:

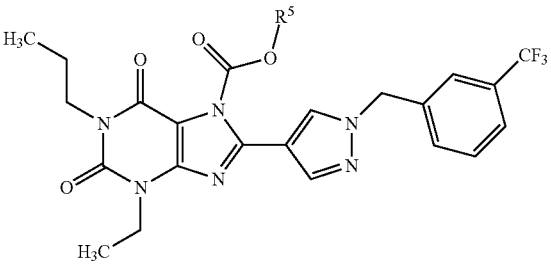

or a pharmaceutically acceptable salt or solvate thereof.

In some embodiments, $R^5$ is $R^7$; $R^7$ is $C_1$-$C_6$alkyl, substituted or unsubstituted $C_1$-$C_6$heteroalkyl, substituted or unsubstituted monocyclic $C_3$-$C_8$cycloalkyl, substituted or unsubstituted bicyclic $C_5$-$C_{10}$cycloalkyl, substituted or unsubstituted monocyclic $C_2$-$C_8$heterocycloalkyl, substituted or unsubstituted bicyclic $C_5$-$C_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—O$R^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, $R^7$ is $C_1$-$C_6$alkyl, substituted or unsubstituted $C_1$-$C_6$heteroalkyl, —CH$_2$-(substituted or unsubstituted phenyl), —CH$_2$-(substituted or unsubstituted heteroaryl), —CH$_2$-(substituted or unsubstituted C$_2$-C$_8$heterocycloalkyl), —CH(R$^{10}$)O—R$^{11}$, or —(CH$_2$CH$_2$O)$_n$—R$^{11}$; R$^{10}$ is hydrogen and methyl; R$^{11}$ is hydrogen, C$_1$-C$_6$alkyl, substituted or unsubstituted C$_1$-C$_6$heteroalkyl, substituted or unsubstituted C$_2$-C$_{10}$heterocycloalkyl, —C(=O)R$^{12}$, —C(=O)—OR$^{12}$, —C(=O)N(R$^{12}$)(R$^8$), —C(=O)—SR$^{12}$, or —P(=O)(OH)$_2$.

In some embodiments, the compound has one of the following structures:

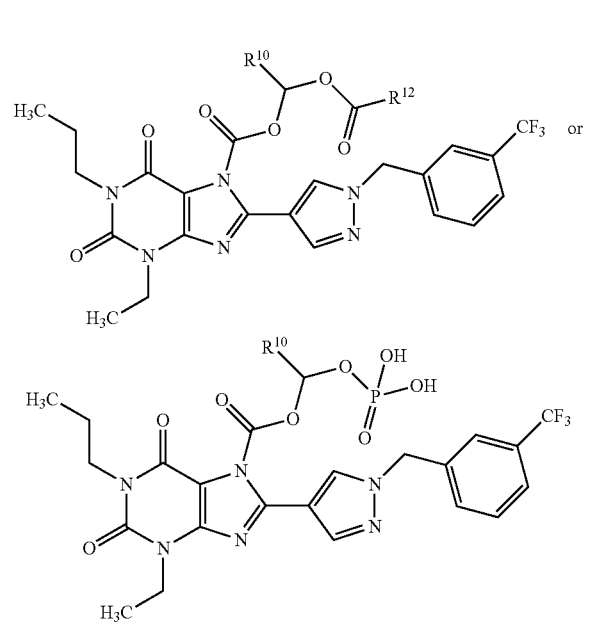

or a pharmaceutically acceptable salt or solvate thereof.

In some embodiments, the compound has one of the following structures:

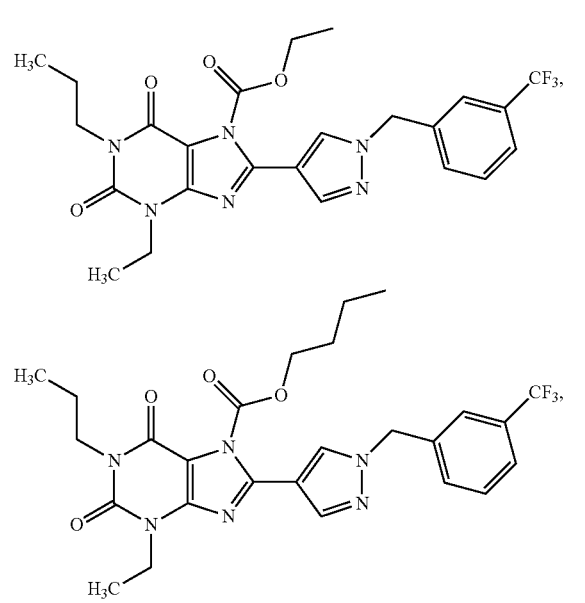

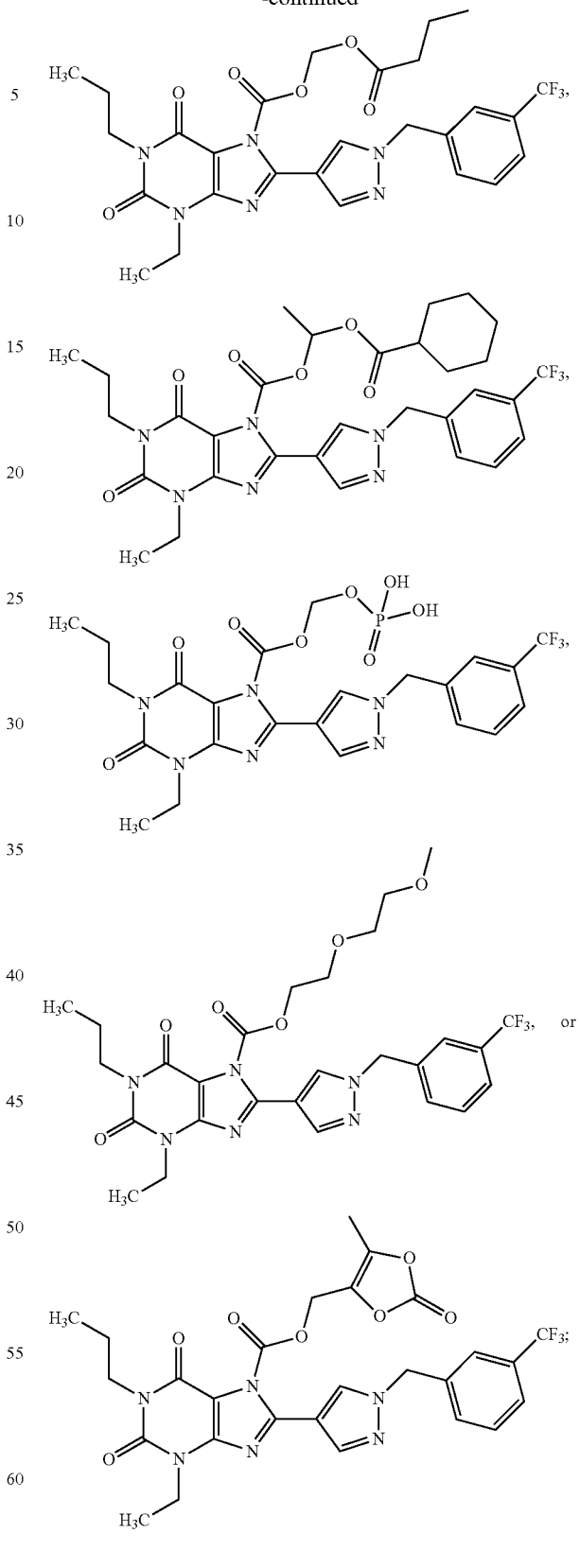

or a pharmaceutically acceptable salt or solvate thereof.

In some embodiments, the compound has the following structure of Formula (I):

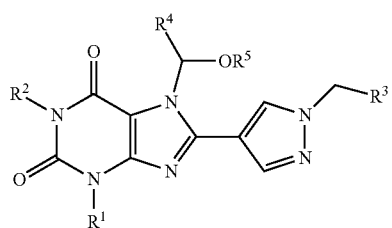

Formula (I)

or a pharmaceutically acceptable salt or solvate thereof.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ is ethyl; $R^2$ is n-propyl; and $R^3$ is 3-(trifluoromethyl)phenyl.

In some embodiments, the compound has the following structure:

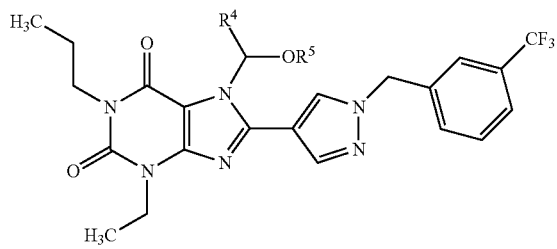

or a pharmaceutically acceptable salt or solvate thereof.

In some embodiments, $R^4$ is methyl or ethyl; $R^5$ is hydrogen, $R^7$, —C(=O)$R^7$, —C(=O)—O$R^7$, —C(=O)N($R^7$)($R^8$), —C(=O)—S$R^7$, or —P(=O)(O$R^9$)$_2$; $R^7$ is $C_1$-$C_6$alkyl, substituted or unsubstituted $C_1$-$C_6$heteroalkyl, substituted or unsubstituted monocyclic $C_3$-$C_8$cycloalkyl, substituted or unsubstituted bicyclic $C_5$-$C_{10}$cycloalkyl, substituted or unsubstituted monocyclic $C_2$-$C_8$heterocycloalkyl, substituted or unsubstituted bicyclic $C_5$-$C_{10}$heterocycloalkyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—O$R^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, $R^5$ is $R^7$, —C(=O)$R^7$, —C(=O)—O$R^7$, —C(=O)N($R^7$)($R^8$), —C(=O)—S$R^7$, or —P(=O)(OH)$_2$; $R^7$ is $C_1$-$C_6$alkyl, substituted or unsubstituted $C_1$-$C_6$heteroalkyl, substituted or unsubstituted cyclohexyl, substituted or unsubstituted cyclopentyl, substituted or unsubstituted bicyclo[1.1.1]pentanyl, substituted or unsubstituted bicyclo[2.2.1]heptanyl, substituted or unsubstituted bicyclo[2.2.2]octanyl, substituted or unsubstituted bicyclo[3.2.1]octanyl, substituted or unsubstituted bicyclo[3.3.0]octanyl, substituted or unsubstituted bicyclo[4.3.0]nonanyl, or substituted or unsubstituted decalinyl, substituted or unsubstituted oxetanyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, substituted or unsubstituted thiomorpholinyl, substituted or unsubstituted phenyl, substituted or unsubstituted monocyclic heteroaryl, —CH$_2$-(substituted or unsubstituted phenyl), —CH$_2$-(substituted or unsubstituted heteroaryl), —CH$_2$-(substituted or unsubstituted $C_2$-$C_8$heterocycloalkyl), —CH($R^{10}$)O—$R^{11}$, —(CH$_2$CH$_2$O)$_n$—$R^{11}$, or —(C($R^{10}$)$_2$)$_p$—O$R^{11}$; each $R^{10}$ is independently selected from hydrogen and methyl; $R^{11}$ is hydrogen, $C_1$-$C_6$alkyl, substituted or unsubstituted $C_1$-$C_6$heteroalkyl, substituted or unsubstituted $C_2$-$C_{10}$heterocycloalkyl, —C(=O)$R^{12}$, —C(=O)—O$R^{12}$, —C(=O)N($R^{12}$)($R^8$), —C(=O)—S$R^{12}$, or —P(=O)(O$R^9$)$_2$.

In some embodiments, the compound has one of the following structures:

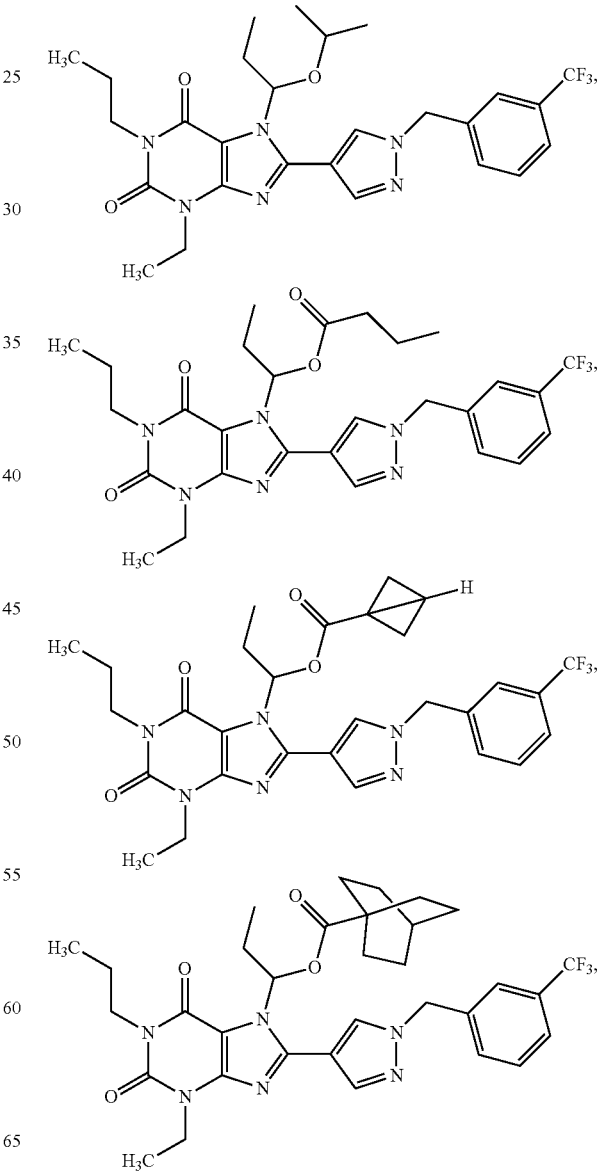

37
-continued
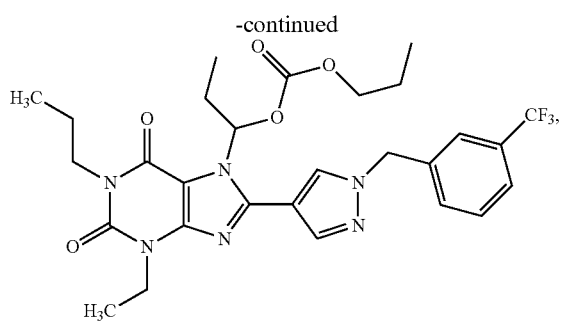
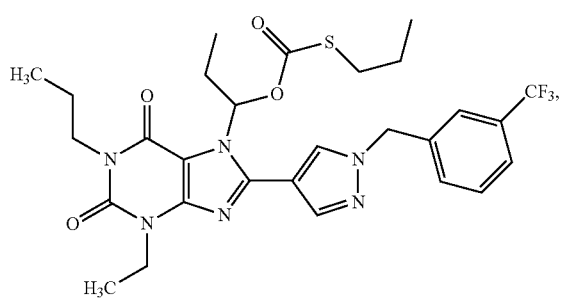
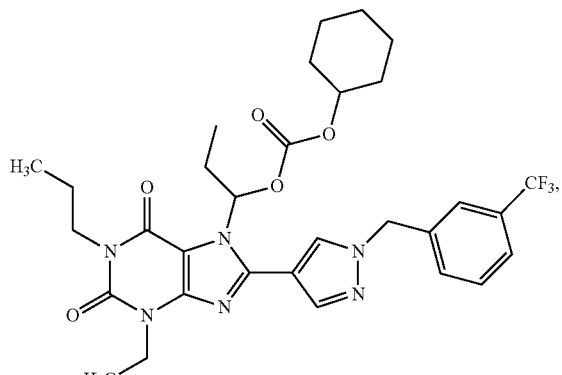
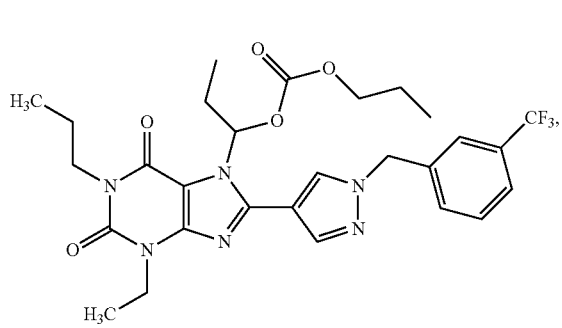
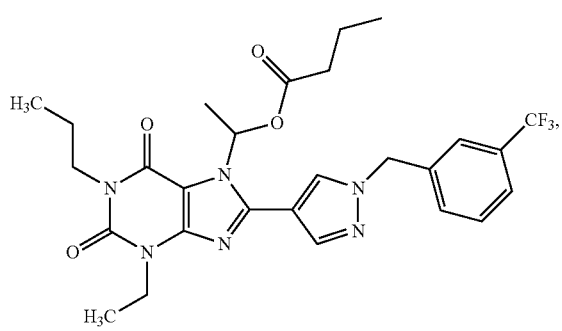
38
-continued
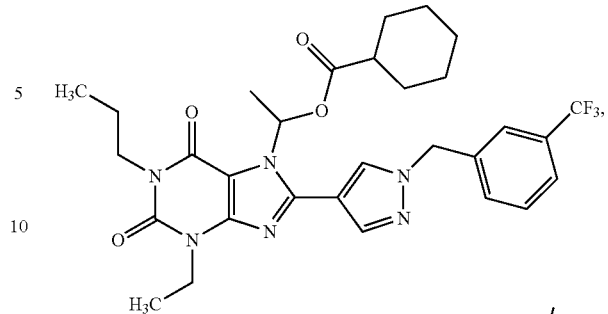
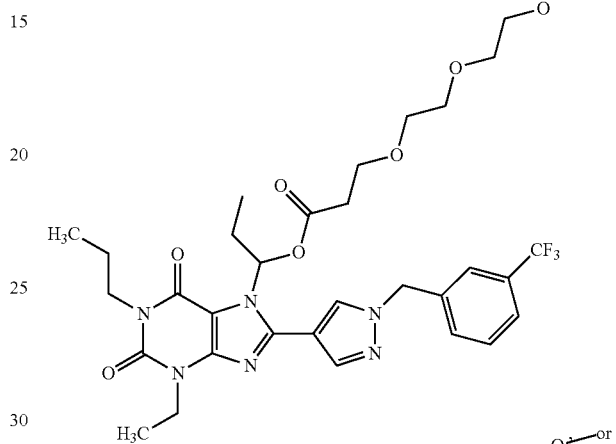
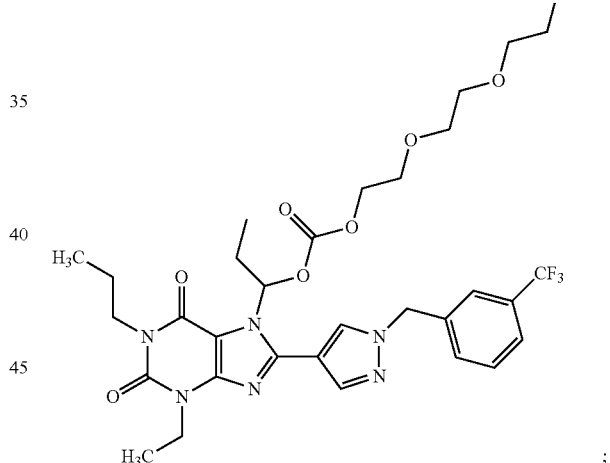
or a pharmaceutically acceptable salt or solvate thereof.
In some embodiments, the compound has the following structure of Formula (II):
Formula (II)
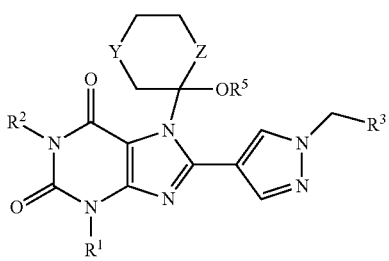
wherein:
Y is selected from —CH$_2$—, O, S, —NR$^{15}$—, and —S(O)$_2$—;
Z is O or S;
or a pharmaceutically acceptable salt or solvate thereof.

In some embodiments, R¹ and R² are each independently selected from substituted or unsubstituted $C_1$-$C_6$alkyl; R³ is selected from substituted or unsubstituted phenyl.

In some embodiments, R¹ is ethyl; R² is n-propyl; and R³ is 3-(trifluoromethyl)phenyl.

In some embodiments, the compound has the following structure:

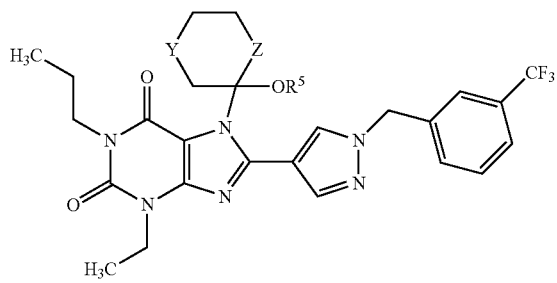

or a pharmaceutically acceptable salt or solvate thereof.

In some embodiments, the compound has the following structure:

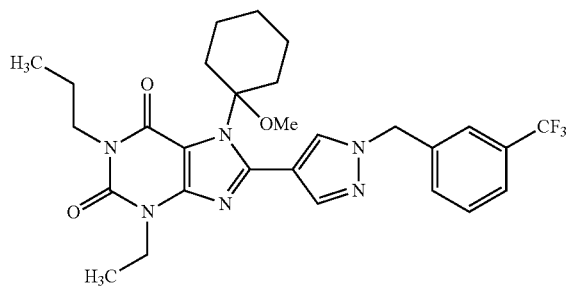 [SMILES: CCCn1c(=O)c2c(nc(-c3cnn(Cc4cccc(C(F)(F)F)c4)c3)n2C2(OC)CCCCC2)n(CC)c1=O]

or a pharmaceutically acceptable salt or solvate thereof.

In some embodiments, the compound has the following structure of Formula (IIa):

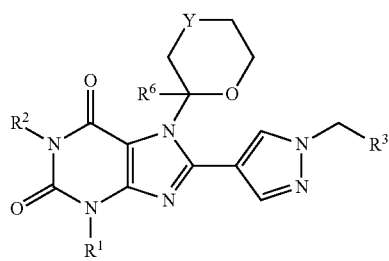

Formula (IIa)

wherein:

Y is selected from —$CH_2$—, O, S, —$NR^{15}$—, and —$S(O)_2$—;

or a pharmaceutically acceptable salt or solvate thereof.

In some embodiments, R¹ and R² are each independently selected from substituted or unsubstituted $C_1$-$C_6$alkyl; R³ is selected from substituted or unsubstituted phenyl.

In some embodiments, substituted means that the referenced group is substituted with one or more additional groups individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2$$NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, substituted means that the referenced group is substituted with one or more additional groups individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2$$NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, and heterocycloalkyl. In yet other embodiments, substituted means that the referenced group is substituted with one or more additional groups individually and independently selected from halogen, —CN, —$NH_2$, —NH(alkyl), —N(alkyl)$_2$, —OH, —$CO_2$H, —$CO_2$alkyl, —C(=O)$NH_2$, —C(=O)NH(alkyl), —C(=O)N(alkyl)$_2$, —S(=O)$_2$$NH_2$, —S(=O)$_2$NH(alkyl), —S(=O)$_2$N(alkyl)$_2$, alkyl, fluoroalkyl, alkoxy, and fluoroalkoxy.

In some embodiments, R¹ is ethyl; R² is n-propyl; and R³ is 3-(trifluoromethyl)phenyl.

In some embodiments, the compound has the following structure:

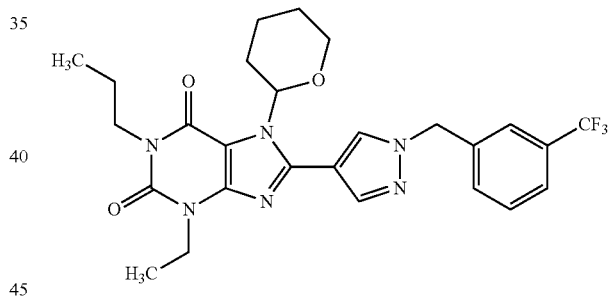

or a pharmaceutically acceptable salt or solvate thereof.

In some embodiments, compounds of Formula (A) include those described in Table 1.

TABLE 1

| Compound | Structure | Name |
| --- | --- | --- |
| A | (structure shown) | (butyryloxy)methyl 3-ethyl-2,6-dioxo-1-propyl-8-(1-(3-(trifluoromethyl)benzyl)-1H-pyrazol-4-yl)-1,2,3,6-tetrahydro-7H-purine-7-carboxylate |

TABLE 1-continued

| Compound | Structure | Name |
|---|---|---|
| B | 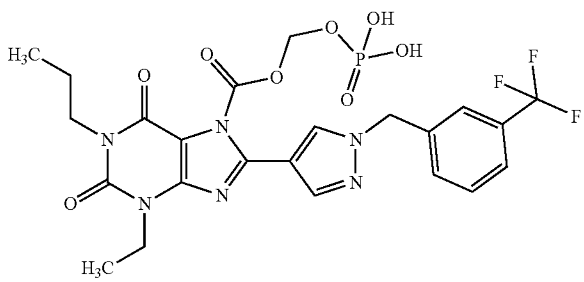 [SMILES: CCCn1c(=O)c2c(nc(-c3cnn(Cc4cccc(C(F)(F)F)c4)c3)n2C(=O)OCOP(=O)(O)O)n(CC)c1=O] | (phosphonooxy)methyl 3-ethyl-2,6-dioxo-1-propyl-8-(1-(3-(trifluoromethyl)benzyl)-1H-pyrazol-4-yl)-1,2,3,6-tetrahydro-7H-purine-7-carboxylate |
| F | 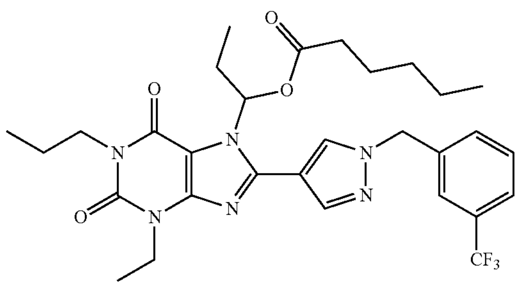 [SMILES: CCCCCC(=O)OC(CC)n1c(-c2cnn(Cc3cccc(C(F)(F)F)c3)c2)nc2c1c(=O)n(CCC)c(=O)n2CC] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl hexanoate |
| G | 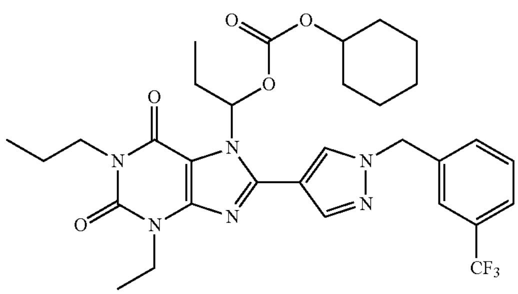 [SMILES: CCCn1c(=O)c2c(nc(-c3cnn(Cc4cccc(C(F)(F)F)c4)c3)n2C(CC)OC(=O)OC2CCCCC2)n(CC)c1=O] | cyclohexyl (1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl)carbonate |
| H | 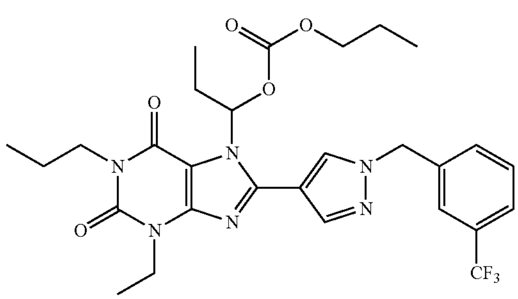 [SMILES: CCCOC(=O)OC(CC)n1c(-c2cnn(Cc3cccc(C(F)(F)F)c3)c2)nc2c1c(=O)n(CCC)c(=O)n2CC] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl propyl carbonate |
| I | 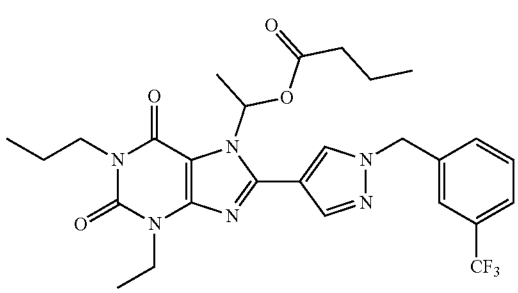 [SMILES: CCCC(=O)OC(C)n1c(-c2cnn(Cc3cccc(C(F)(F)F)c3)c2)nc2c1c(=O)n(CCC)c(=O)n2CC] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)ethyl butyrate |

TABLE 1-continued

| Compound | Structure | Name |
| --- | --- | --- |
| K | 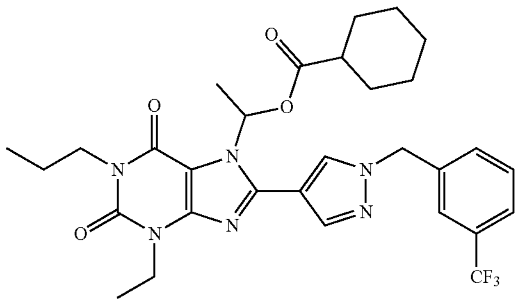 [SMILES: CCCn1c(=O)c2c(nc(-c3cnn(Cc4cccc(C(F)(F)F)c4)c3)n2C(C)OC(=O)C2CCCCC2)n(CC)c1=O] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)ethyl cyclohexanecarboxylate |
| M | 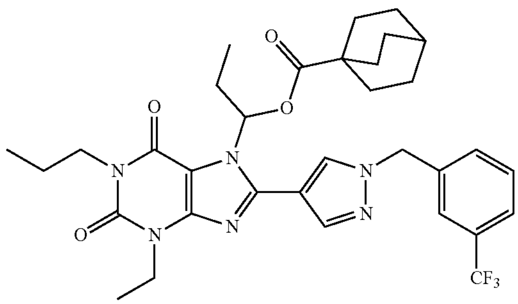 [SMILES: CCCn1c(=O)c2c(nc(-c3cnn(Cc4cccc(C(F)(F)F)c4)c3)n2C(CC)OC(=O)C23CCC(CC2)CC3)n(CC)c1=O] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl bicyclo[2.2.2]octane-1-carboxylate |
| O | 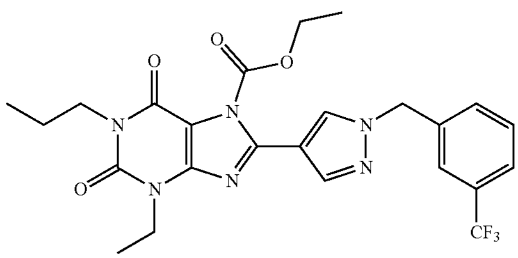 [SMILES: CCCn1c(=O)c2c(nc(-c3cnn(Cc4cccc(C(F)(F)F)c4)c3)n2C(=O)OCC)n(CC)c1=O] | ethyl 3-ethyl-2,6-dioxo-1-propyl-8-(1-(3-(trifluoromethyl)benzyl)-1H-pyrazol-4-yl)-1,2,3,6-tetrahydro-7H-purine-7-carboxylate |
| P | 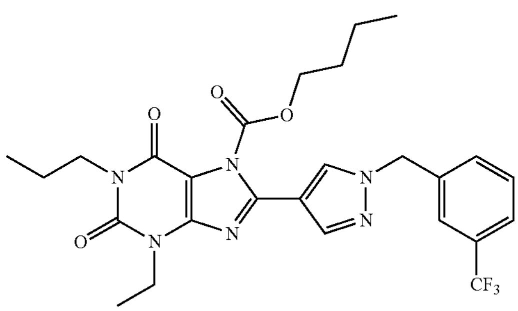 [SMILES: CCCCOC(=O)n1c(-c2cnn(Cc3cccc(C(F)(F)F)c3)c2)nc2c1c(=O)n(CCC)c(=O)n2CC] | butyl 3-ethyl-2,6-dioxo-1-propyl-8-(1-(3-(trifluoromethyl)benzyl)-1H-pyrazol-4-yl)-1,2,3,6-tetrahydro-7H-purine-7-carboxylate |
| Q | 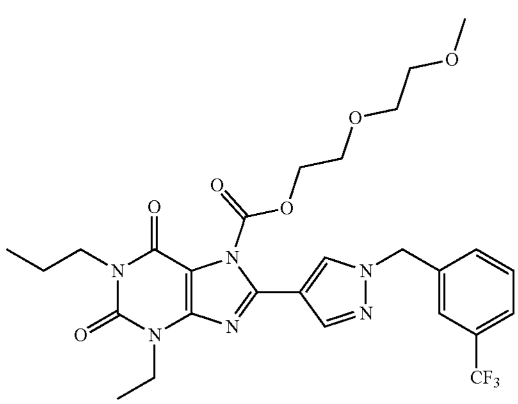 [SMILES: CCCn1c(=O)c2c(nc(-c3cnn(Cc4cccc(C(F)(F)F)c4)c3)n2C(=O)OCCOCCOC)n(CC)c1=O] | 2-(2-methoxyethoxy)ethyl 3-ethyl-2,6-dioxo-1-propyl-8-(1-(3-(trifluoromethyl)benzyl)-1H-pyrazol-4-yl)-1,2,3,6-tetrahydro-7H-purine-7-carboxylate |

TABLE 1-continued

| Compound | Structure | Name |
|---|---|---|
| S | 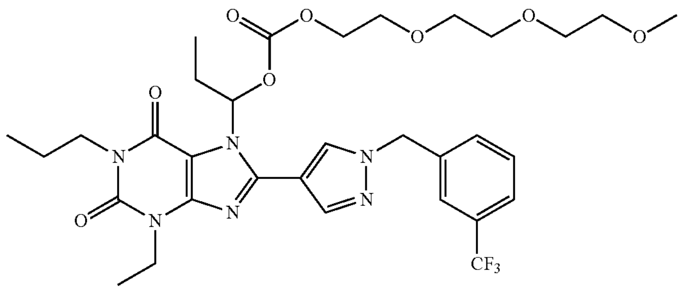 [SMILES: CCCn1c(=O)c2c(nc(-c3cnn(Cc4cccc(C(F)(F)F)c4)c3)n2C(CC)OC(=O)OCCOCCOCCOC)n(CC)c1=O] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl (2-(2-(2-methoxyethoxy)ethoxy)ethyl) carbonate |
| T | 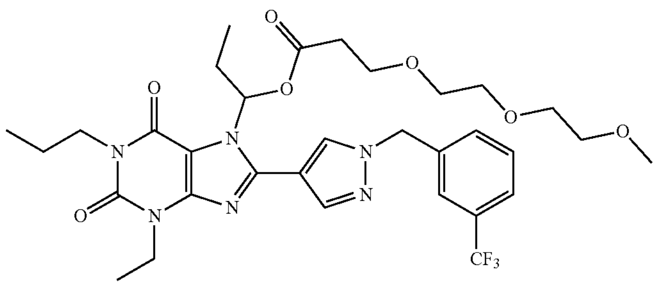 [SMILES: CCCn1c(=O)c2c(nc(-c3cnn(Cc4cccc(C(F)(F)F)c4)c3)n2C(CC)OC(=O)CCOCCOCCOC)n(CC)c1=O] | 1-(3-ethyl-2,6-dioxo-1-propyl-8-(1-(3-(trifluoromethyl)benzyl)-1H-pyrazol-4-yl)-1,2,3,6-tetrahydro-7H-purin-7-yl)propyl 3-(2-(2-methoxyethoxy)ethoxy)propanoate |

In another aspect, described herein is a compound represented by Formula (B):

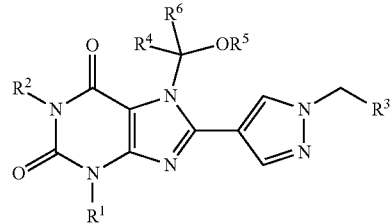

Formula (B)

or a pharmaceutically acceptable salt or solvate thereof, wherein:

$R^1$ and $R^2$ are each independently selected from hydrogen, and substituted or unsubstituted alkyl;

$R^3$ is selected from substituted or unsubstituted phenyl, and substituted or unsubstituted heteroaryl, wherein if $R^3$ is substituted then $R^3$ is substituted with one or more groups selected from halogen, —CN, —OH, $C_1$-$C_4$alkyl, $C_2$-$C_4$alkenyl, $C_2$-$C_4$alkynyl, $C_1$-$C_4$alkoxy, $C_1$-$C_4$fluoroalkyl, $C_1$-$C_4$fluoroalkoxy, and substituted or unsubstituted $C_1$-$C_4$heteroalkyl;

$R^4$ is hydrogen or substituted or unsubstituted alkyl;

$R^6$ is hydrogen or substituted or unsubstituted alkyl;

or $R^4$ and $R^6$ are taken together with the carbon atom to which they are attached to form a carbonyl (C=O);

or $R^4$ and $R^6$ are taken together with the carbon atom to which they are attached to form a ring that is a substituted or unsubstituted $C_3$-$C_{10}$cycloalkyl, or substituted or unsubstituted $C_2$-$C_{10}$heterocycloalkyl, wherein if the ring is substituted then it is substituted with one or more $R^{15}$;

$R^{15}$ is hydrogen, substituted or unsubstituted alkyl, substituted or unsubstituted heteroalkyl, substituted or unsubstituted phenyl, substituted or unsubstituted heteroaryl, -alkyl-(substituted or unsubstituted phenyl), -alkyl-(substituted or unsubstituted heteroaryl), —C(=O)$R^{16}$, —C(=O)—O$R^{16}$, —C(=O)N($R^{16}$)$_2$;

each $R^{16}$ is independently selected from hydrogen and substituted or unsubstituted alkyl;

$R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —(C($R^{10}$)$_2$O)$_m$—$R^{11}$, —C(=O)—(C($R^{10}$)$_2$O)$_m$—$R^{11}$, —C(=O)—(CH$_2$CH$_2$O)$_n$—$R^{11}$, —C(=O)—$R^a$ or —C(=O)—O$R^7$;

$R^a$ is substituted or unsubstituted bicyclic cycloalkyl, substituted or unsubstituted bicyclic heterocycloalkyl, substituted or unsubstituted bicyclic heteroaryl, (substituted or unsubstituted heterocycloalkyl containing at least one O atom in the ring), substituted or unsubstituted azetidinyl, substituted or unsubstituted piperidinyl, substituted or unsubstituted azapenyl, substituted or unsubstituted 5-membered heteroaryl, substituted or unsubstituted pyridin-2-yl, substituted or unsubstituted pyridin-4-yl, substituted or unsubstituted pyrimidinyl, substituted or unsubstituted pyrazinyl, substituted or unsubstituted pyridazinyl, substituted or unsubstituted triazinyl;

or $R^4$ and $R^5$ are taken together with the atoms to which they are attached to form a substituted or unsubstituted $C_2$-$C_{10}$heterocycloalkyl;

$R^7$ is substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —$(C(R^{10})_2O)_m$—$R^{11}$, —$(CH_2CH_2O)_n$—$R^{11}$, or —$(C(R^{10})_2)_p$—$OR^{11}$;

each $R^9$ is independently selected from hydrogen and alkyl;

each $R^{10}$ is independently selected from hydrogen and alkyl;

$R^{11}$ is hydrogen, substituted or unsubstituted alkyl, substituted or unsubstituted heteroalkyl, substituted or unsubstituted $C_2$-$C_{10}$heterocycloalkyl, —C(=O)$R^{12}$, —C(=O)—$OR^{12}$, —C(=O)N($R^{12}$)($R^8$), —C(=O)—$SR^{12}$, or —P(=O)$(OR^9)_2$;

$R^{12}$ is hydrogen, substituted or unsubstituted alkyl, substituted or unsubstituted heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), or -alkyl-(substituted or unsubstituted heteroaryl);

m is 1, 2, 3, 4, 5, or 6;

n is 1, 2, 3, 4, 5, or 6.

p is 1, 2, 3, 4, 5, or 6;

wherein substituted means that the referenced group is substituted with one or more additional groups individually and independently selected from halogen, —CN, —$NH_2$, —NH(alkyl), —N(alkyl)$_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone.

In some embodiments, m is 1, 2, 3, 4, 5, or 6. In some embodiments, m is 1, 2, 3, 4, or 5. In some embodiments, m is 1, 2, 3, or 4. In some embodiments, m is 1, 2, or 3. In some embodiments, m is 1 or 2. In some embodiments, m is 1. In some embodiments, m is 2, 3, 4, 5, or 6.

In some embodiments, n is 1, 2, 3, 4, 5, or 6. In some embodiments, n is 1, 2, 3, 4, or 5. In some embodiments, n is 1, 2, 3, or 4. In some embodiments, n is 1, 2, or 3. In some embodiments, n is 1 or 2. In some embodiments, n is 2 or 3. In some embodiments, n is 1. In some embodiments, n is 2. In some embodiments, n is 3. In some embodiments, n is 2, 3, 4, 5, or 6.

In some embodiments, p is 1, 2, 3, 4, 5, or 6. In some embodiments, p is 1, 2, 3, 4, or 5. In some embodiments, p is 1, 2, 3, or 4. In some embodiments, p is 1, 2, or 3. In some embodiments, p is 1 or 2. In some embodiments, p is 1. In some embodiments, p is 2, 3, 4, 5, or 6.

In some embodiments, $R^4$ is hydrogen; $R^6$ is hydrogen; $R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl), —$(C(R^{10})_2O)_m$—$R^{11}$, —C(=O)—$(C(R^{10})_2O)_m$—$R^{11}$, —C(=O)—$(CH_2CH_2O)_n$—$R^{11}$, —C(=O)—$R^a$ or —C(=O)—$OR^7$.

In some embodiments, $R^1$ and $R^2$ are each independently selected from substituted or unsubstituted $C_1$-$C_6$alkyl. In some embodiments, $R^1$ and $R^2$ are each independently selected from unsubstituted $C_1$-$C_3$alkyl. In some embodiments, $R^1$ is ethyl. In some embodiments, $R^2$ is n-propyl. In some embodiments, $R^1$ is ethyl and $R^2$ is n-propyl.

In some embodiments, $R^3$ is selected from substituted or unsubstituted phenyl. In some embodiments, $R^3$ is substituted phenyl. In some embodiments, $R^3$ is phenyl substituted by one or more groups independently selected from halogen, $C_1$-$C_4$ alkyl, or $C_1$-$C_4$ fluoroalkyl. In some embodiments, $R^3$ is phenyl substituted by one or more groups independently selected from $C_1$-$C_4$ fluoroalkyl. In some embodiments, $R^3$ is selected from phenyl substituted with one, two, or three —$CF_3$ substituents. In some embodiments, $R^3$ is selected from phenyl substituted with one —$CF_3$ substituent. In some embodiments, $R^3$ is

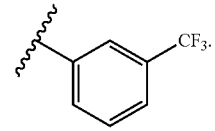 [SMILES: *c1cccc(C(F)(F)F)c1]

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ and $R^2$ are each independently selected from substituted or unsubstituted $C_1$-$C_6$alkyl; $R^3$ is selected from substituted or unsubstituted phenyl.

In some embodiments, $R^1$ and $R^2$ are each independently selected from methyl, ethyl, n-propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, and neohexyl.

In some embodiments, $R^1$ is ethyl; $R^2$ is n-propyl; and $R^3$ is 3-(trifluoromethyl)phenyl.

In some embodiments, the compound has the following structure:

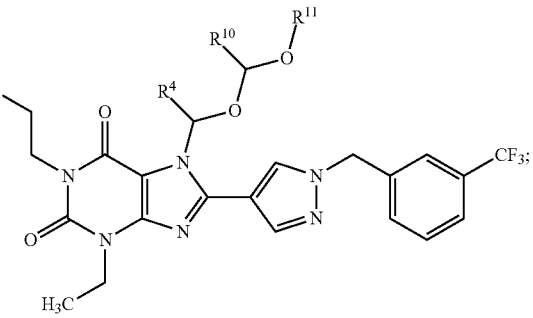

or a pharmaceutically acceptable salt or solvate thereof.

In some embodiments, $R^{11}$ is hydrogen, substituted or unsubstituted alkyl, —C(=O)$R^{12}$, —C(=O)—$OR^{12}$, —C(=O)N($R^{12}$)($R^8$), or —P(=O)$(OR^9)_2$. In some embodiments, $R^{11}$ is substituted or unsubstituted alkyl, —C(=O)$R^{12}$, —C(=O)—$OR^{12}$, or —P(=O)$(OR^9)_2$. In some embodiments, $R^{11}$ is —C(=O)$R^{12}$ or —P(=O)$(OR^9)_2$. In some embodiments, $R^{11}$ is —C(=O)$R^{12}$ or —P(=O)$(OH)_2$.

In some embodiments, the compound has one of the following structures:

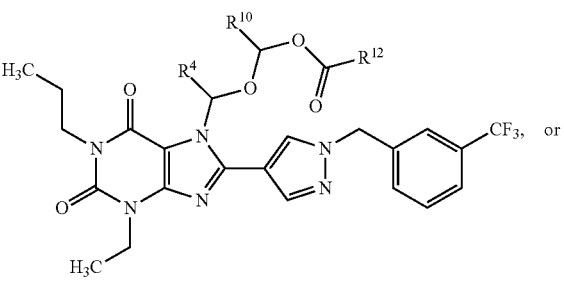

-continued

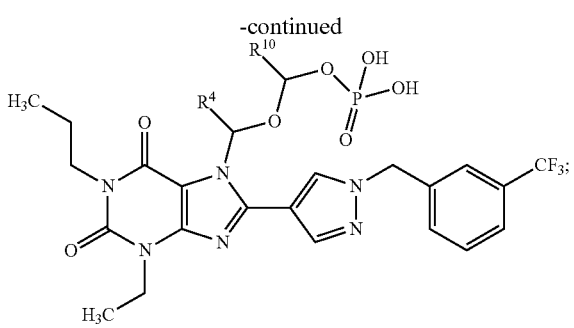

or a pharmaceutically acceptable salt or solvate thereof.

In some embodiments, $R^{12}$ is substituted or unsubstituted alkyl or substituted or unsubstituted $C_3$-$C_{10}$ cycloalkyl. In some embodiments, $R^{12}$ is unsubstituted $C_1$-$C_6$ alkyl or unsubstituted $C_3$-$C_{10}$ cycloalkyl. In some embodiments, $R^{12}$ is unsubstituted $C_1$-$C_3$ alkyl. In some embodiments, $R^{12}$ is unsubstituted $C_3$-$C_6$ cycloalkyl.

In some embodiments, the compound has one of the following structures:

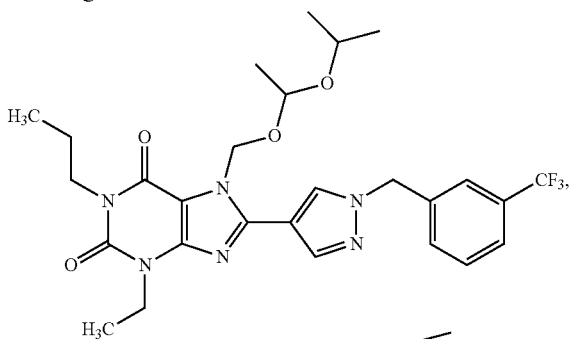

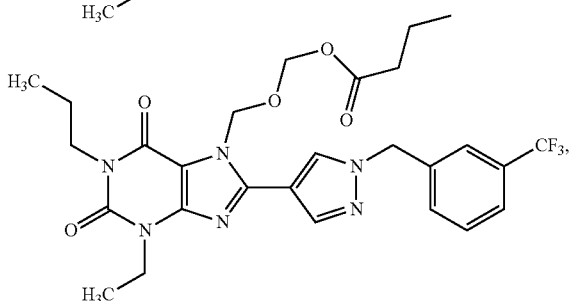

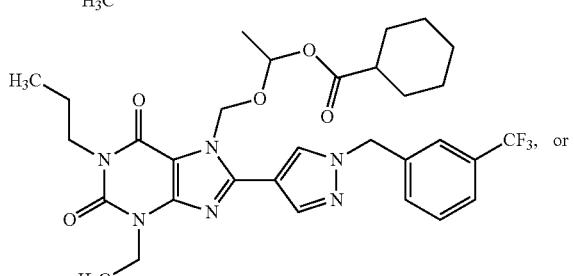

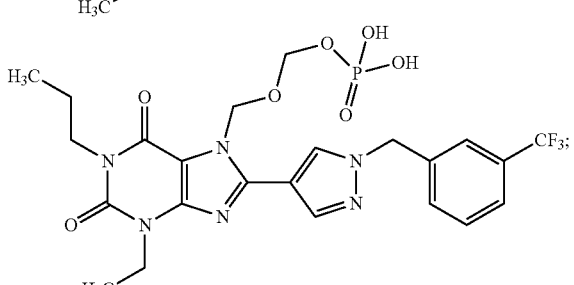

or a pharmaceutically acceptable salt or solvate thereof.

In some embodiments, $R^5$ is —C(=O)—(C($R^{10}$)$_2$O)$_n$$R^{11}$, —C(=O)—(CH$_2$CH$_2$O)$_n$$R^{11}$, —C(=O)—$R^a$ or —C(=O)—O$R^7$.

In some embodiments, the compound has the following structure:

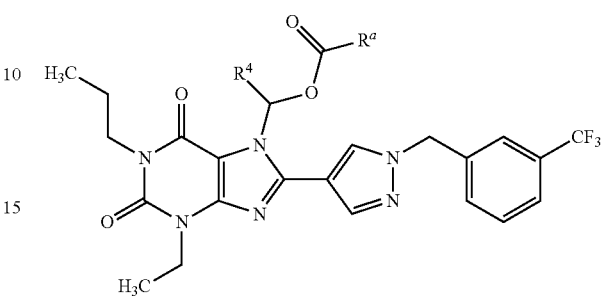

or a pharmaceutically acceptable salt or solvate thereof.

In some embodiments, $R^a$ is substituted or unsubstituted bicyclic cycloalkyl that is a fused bicyclic cycloalkyl, bridged bicyclic cycloalkyl, or spiro bicyclic cycloalkyl; or $R^a$ is substituted or unsubstituted bicyclic heterocycloalkyl that is a fused bicyclic heterocycloalkyl, bridged bicyclic heterocycloalkyl, or spiro bicyclic heterocycloalkyl; or $R^a$ is substituted or unsubstituted bicyclic heteroaryl.

In some embodiments, $R^a$ is substituted or unsubstituted bicyclo[1.1.1]pentanyl, substituted or unsubstituted bicyclo[2.2.1]heptanyl, substituted or unsubstituted bicyclo[2.2.2]octanyl, substituted or unsubstituted bicyclo[3.2.1]octanyl, substituted or unsubstituted bicyclo[3.3.0]octanyl, substituted or unsubstituted bicyclo[4.3.0]nonanyl, or substituted or unsubstituted decalinyl.

In some embodiments, the compound has one of the following structures:

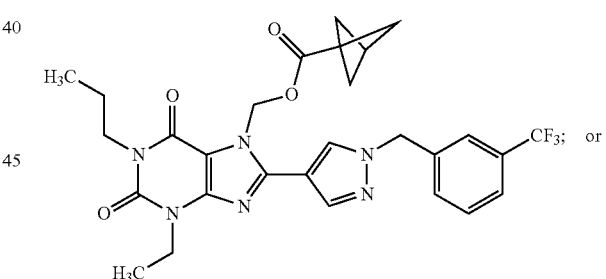

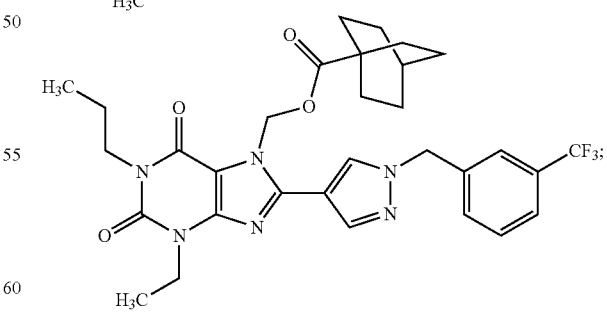

or a pharmaceutically acceptable salt or solvate thereof.

In some embodiments, $R^a$ is substituted or unsubstituted heterocycloalkyl containing at least one O atom in the ring, substituted or unsubstituted azetidinyl, substituted or unsubstituted piperidinyl, substituted or unsubstituted azapenyl, substituted or unsubstituted 5-membered heteroaryl, substituted or unsubstituted pyridin-2-yl, substituted or unsubstituted pyridin-4-yl, substituted or unsubstituted pyrimidinyl, substituted or unsubstituted pyrazinyl, substituted or unsubstituted pyridazinyl, substituted or unsubstituted triazinyl. In some embodiments, $R^a$ is substituted or unsubstituted tetrahydrofuranyl, substituted or unsubstituted tetrahydropyranyl, substituted or unsubstituted tetrahydrodioxanyl, substituted or unsubstituted azetidinyl, substituted or unsubstituted piperidinyl, substituted or unsubstituted azapenyl, substituted or unsubstituted pyrrolyl, substituted or unsubstituted imidazolyl, substituted or unsubstituted pyrazolyl, substituted or unsubstituted triazolyl, substituted or unsubstituted tetrazolyl, substituted or unsubstituted oxazolyl, substituted or unsubstituted isoxazolyl, substituted or unsubstituted thiazolyl, substituted or unsubstituted isothiazolyl, substituted or unsubstituted pyridin-2-yl, substituted or unsubstituted pyridin-4-yl, substituted or unsubstituted pyrimidinyl, substituted or unsubstituted pyrazinyl, substituted or unsubstituted pyridazinyl, substituted or unsubstituted triazinyl. In some embodiments, $R^a$ is substituted or unsubstituted tetrahydrodioxanyl, substituted or unsubstituted azetidinyl, substituted or unsubstituted piperidinyl, substituted or unsubstituted imidazolyl, substituted or unsubstituted pyridin-2-yl, substituted or unsubstituted pyridin-4-yl, or substituted or unsubstituted pyrimidinyl.

In some embodiments, $R^a$ is a substituted or unsubstituted heterocycloalkyl containing at least one O atom in the ring that is substituted or unsubstituted tetrahydrofuranyl, substituted or unsubstituted dihydrofuranyl, substituted or unsubstituted oxazolidinonyl, substituted or unsubstituted tetrahydropyranyl, substituted or unsubstituted dihydropyranyl, substituted or unsubstituted tetrahydrothiopyranyl, substituted or unsubstituted morpholinyl, substituted or unsubstituted oxetanyl, substituted or unsubstituted oxepanyl, substituted or unsubstituted oxazepinyl, or substituted or unsubstituted dioxanyl.

In some embodiments, $R^a$ is a substituted or unsubstituted 5-membered heteroaryl that is substituted or unsubstituted furanyl, substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, or substituted or unsubstituted thiadiazolyl.

In some embodiments, the compound has one of the following structures:

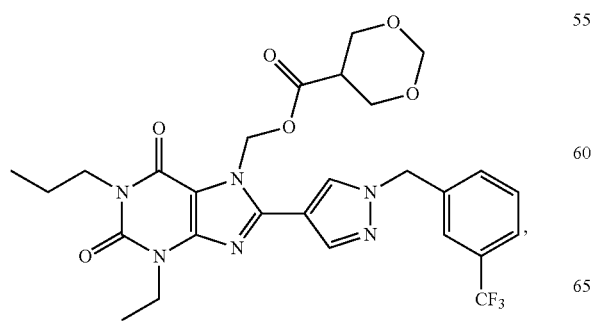

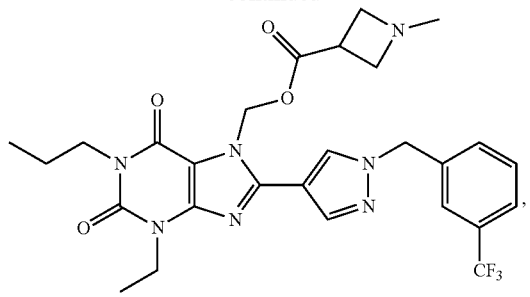

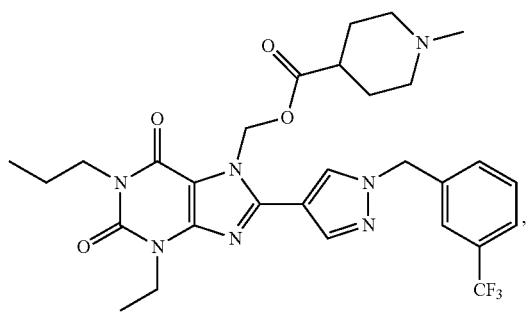

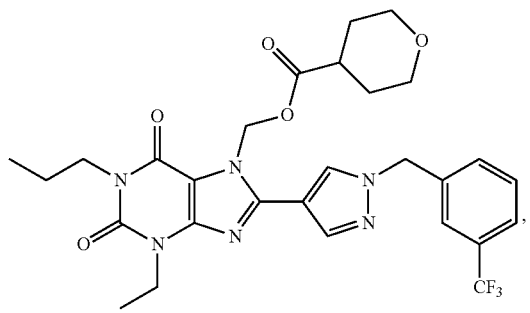

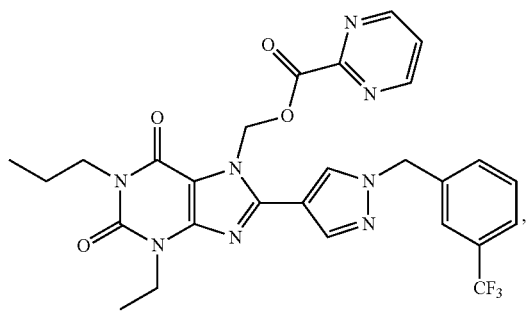

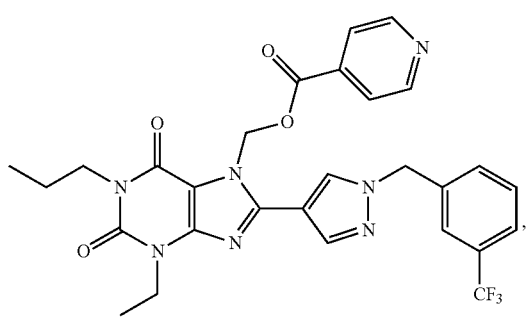

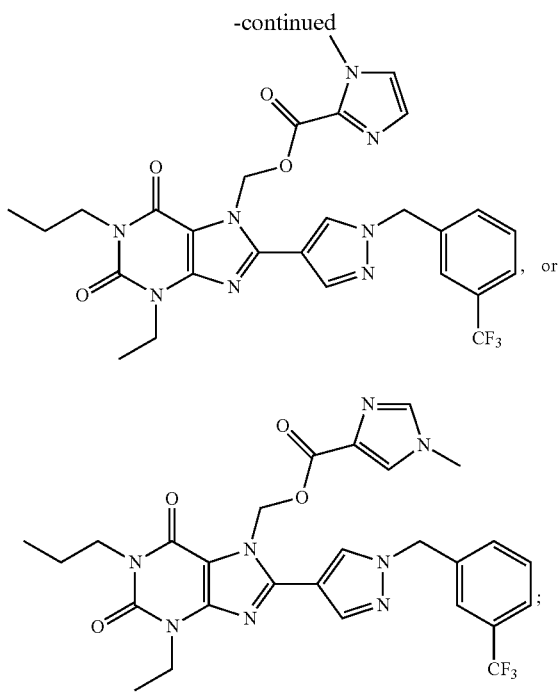

, or

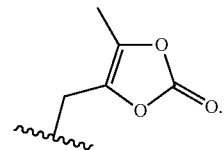 [SMILES: *Cc1oc(=O)oc1C]

or a pharmaceutically acceptable salt or solvate thereof.

In some embodiments, $R^1$ is ethyl; $R^2$ is n-propyl; $R^3$ is 3-(trifluoromethyl)phenyl; and $R^5$ is —C(=O)—(C(R$^{10}$)$_2$O)$_m$—R$^{11}$, —C(=O)—(CH$_2$CH$_2$O)$_n$—R$^{11}$, or —C(=O)—OR$^7$.

In some embodiments, the compound has one of the following structures:

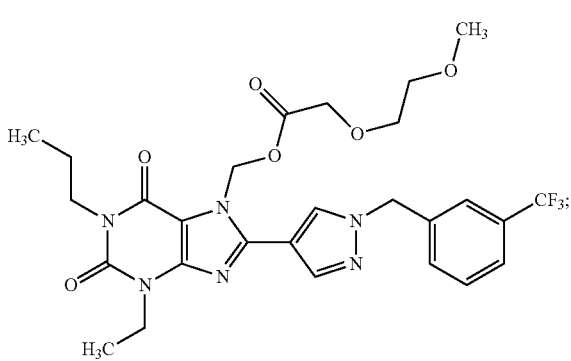 [SMILES: CCCn1c(=O)c2c(nc(-c3cnn(Cc4cccc(C(F)(F)F)c4)c3)n2COC(=O)COCCOC)n(CC)c1=O]

or a pharmaceutically acceptable salt or solvate thereof.

In some embodiments, $R^1$ is ethyl; $R^2$ is n-propyl; $R^3$ is 3-(trifluoromethyl)phenyl; $R^5$ is substituted or unsubstituted $C_3$-$C_{10}$cycloalkyl, substituted or unsubstituted $C_2$-$C_{10}$heterocycloalkyl, substituted or unsubstituted phenyl, substituted or unsubstituted heteroaryl, -alkyl-(substituted or unsubstituted phenyl), -alkyl-(substituted or unsubstituted heteroaryl), -alkyl-(substituted or unsubstituted cycloalkyl), -alkyl-(substituted or unsubstituted heterocycloalkyl). In some embodiments, $R^5$ is —CH$_2$-(substituted or unsubstituted $C_2$-$C_8$heterocycloalkyl). In some embodiments, $R^5$ is —CH$_2$-(substituted $C_5$-$C_6$heterocycloalkyl). In some embodiments, $R^5$ is

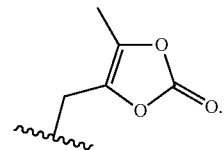 [SMILES: *Cc1oc(=O)oc1C]

In some embodiments, substituted means that the referenced group is substituted with one or more additional groups individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, substituted means that the referenced group is substituted with one or more additional groups individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, and heterocycloalkyl. In yet other embodiments, substituted means that the referenced group is substituted with one or more additional groups individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, fluoroalkyl, alkoxy, and fluoroalkoxy.

In some embodiments, the compound has the following structure:

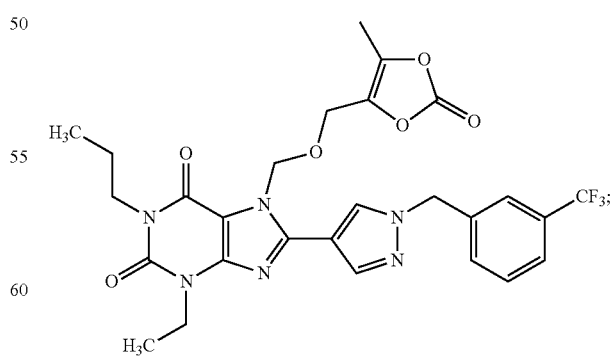

or a pharmaceutically acceptable salt or solvate thereof.

In some embodiments, compounds of Formula (B) include those presented in Table 2.

TABLE 2

| Compound | Structure | Name |
|---|---|---|
| C | 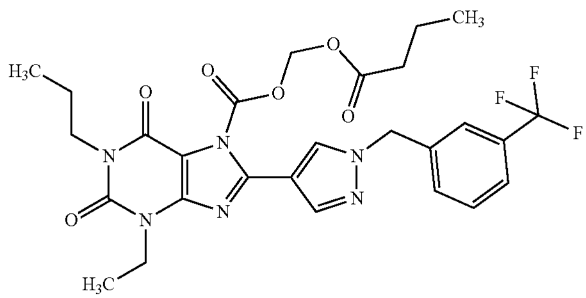 [SMILES: CCCC(=O)OCOC(=O)n1c(-c2cnn(Cc3cccc(C(F)(F)F)c3)c2)nc2c1c(=O)n(CCC)c(=O)n2CC] | ((3-ethyl-2,6-dioxo-1-propyl-8-(1-(3-(trifluoromethyl)benzyl)-1H-pyrazol-4-yl)-1,2,3,6-tetrahydro-7H-purin-7-yl)methoxy)methyl butyrate |
| D | 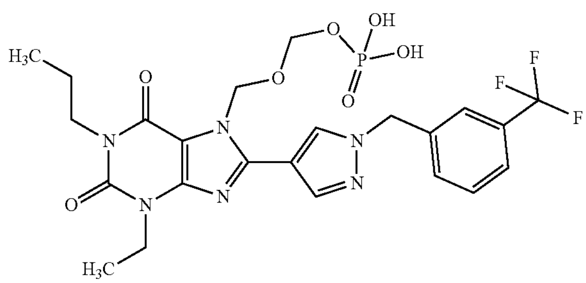 [SMILES: CCCn1c(=O)c2c(nc(-c3cnn(Cc4cccc(C(F)(F)F)c4)c3)n2COCOP(=O)(O)O)n(CC)c1=O] | ((3-ethyl-2,6-dioxo-1-propyl-8-(1-(3-(trifluoromethyl)benzyl)-1H-pyrazol-4-yl)-1,2,3,6-tetrahydro-7H-purin-7-yl)methoxy)methyl dihydrogen phosphate |
| E | 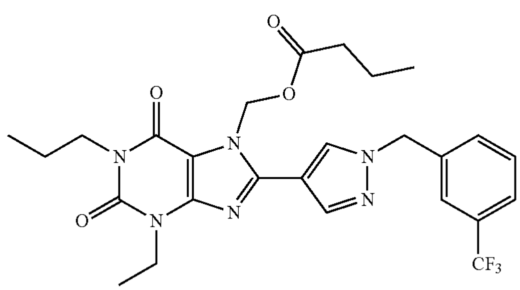 [SMILES: CCCC(=O)OCn1c(-c2cnn(Cc3cccc(C(F)(F)F)c3)c2)nc2c1c(=O)n(CCC)c(=O)n2CC] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl butyrate |
| J | 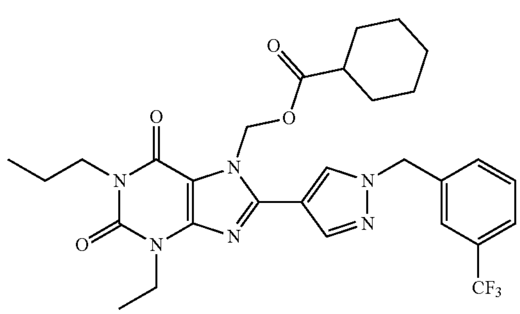 | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl cyclohexanecarboxylate |
| L | 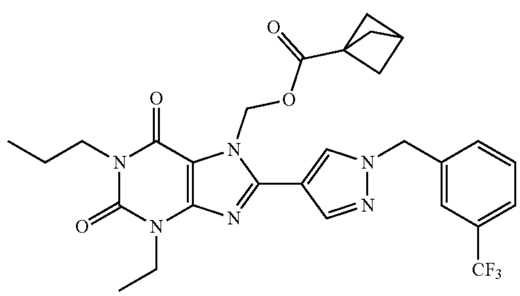 [SMILES: CCCn1c(=O)c2c(nc(-c3cnn(Cc4cccc(C(F)(F)F)c4)c3)n2COC(=O)C23CC(C2)C3)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl bicyclo[1.1.1]pentane-1-carboxylate |

TABLE 2-continued

| Compound | Structure | Name |
| --- | --- | --- |
| N | 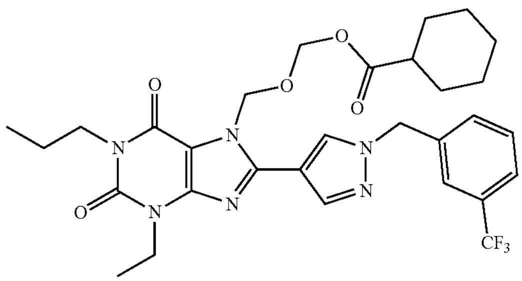 [SMILES: CCCn1c(=O)c2c(nc(-c3cnn(Cc4cccc(C(F)(F)F)c4)c3)n2COCOC(=O)C2CCCCC2)n(CC)c1=O] | ((3-ethyl-2,6-dioxo-1-propyl-8-(1-(3-(trifluoromethyl)benzyl)-1H-pyrazol-4-yl)-1,2,3,6-tetrahydro-7H-purin-7-yl)methoxy)methyl cyclohexanecarboxylate |
| R | 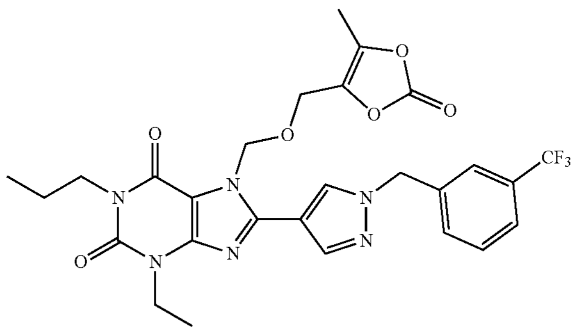 | 3-ethyl-7-(((5-methyl-2-oxo-1,3-dioxol-4-yl)methoxy)methyl)-1-propyl-8-(1-(3-(trifluoromethyl)benzyl)-1H-pyrazol-4-yl)-3,7-dihydro-1H-purine-2,6-dione |
| U | 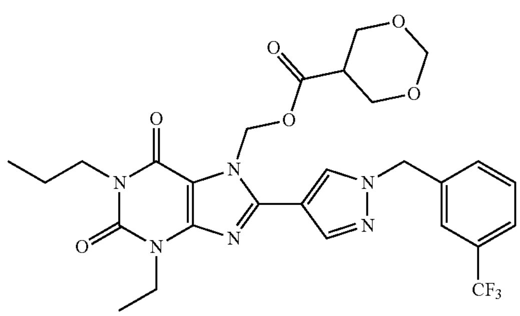 [SMILES: CCCn1c(=O)c2c(nc(-c3cnn(Cc4cccc(C(F)(F)F)c4)c3)n2COC(=O)C2COCOC2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl 1,3-dioxane-5-carboxylate |
| V | 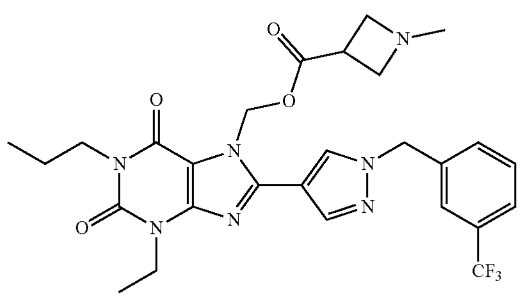 [SMILES: CCCn1c(=O)c2c(nc(-c3cnn(Cc4cccc(C(F)(F)F)c4)c3)n2COC(=O)C2CN(C)C2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl 1-methylazetidine-3-carboxylate |
| AA | 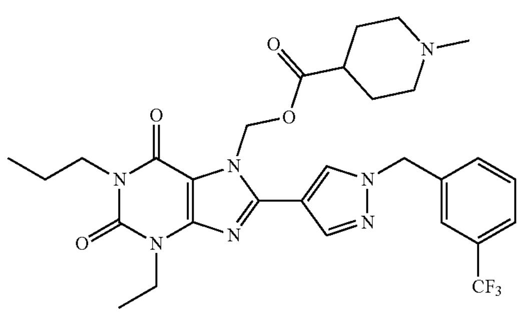 [SMILES: CCCn1c(=O)c2c(nc(-c3cnn(Cc4cccc(C(F)(F)F)c4)c3)n2COC(=O)C2CCN(C)CC2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl 1-methylpiperidine-4-carboxylate |

TABLE 2-continued

| Compound | Structure | Name |
|---|---|---|
| BB | 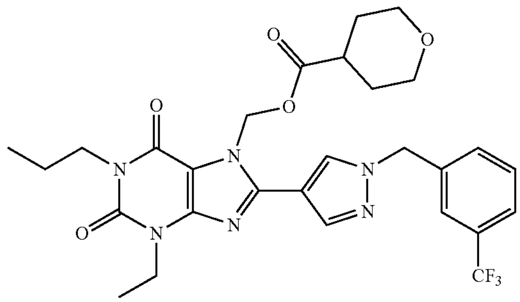 [SMILES: CCCn1c(=O)c2c(nc(-c3cnn(Cc4cccc(C(F)(F)F)c4)c3)n2COC(=O)C2CCOCC2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl tetrahydro-2H-pyran-4-carboxylate |
| CC | 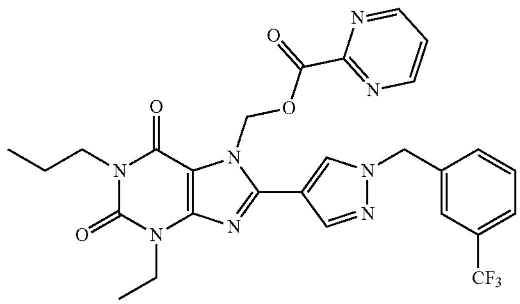 [SMILES: CCCn1c(=O)c2c(nc(-c3cnn(Cc4cccc(C(F)(F)F)c4)c3)n2COC(=O)c2ncccn2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl pyrimidine-2-carboxylate |
| DD | 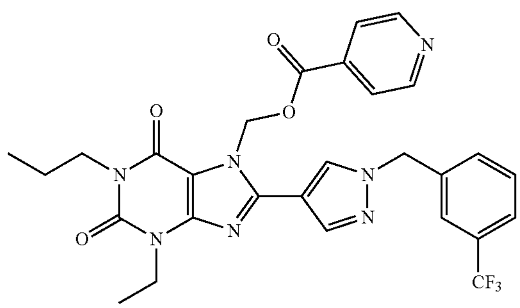 [SMILES: CCCn1c(=O)c2c(nc(-c3cnn(Cc4cccc(C(F)(F)F)c4)c3)n2COC(=O)c2ccncc2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl isonicotinate |
| EE | 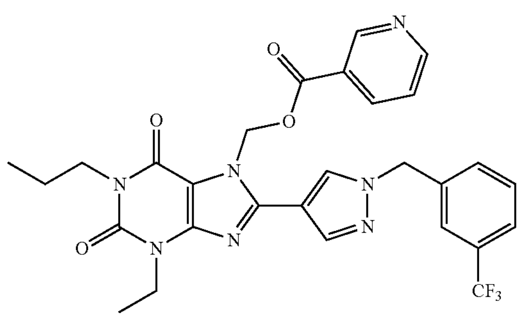 [SMILES: CCCn1c(=O)c2c(nc(-c3cnn(Cc4cccc(C(F)(F)F)c4)c3)n2COC(=O)c2cccnc2)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl nicotinate |
| FF | 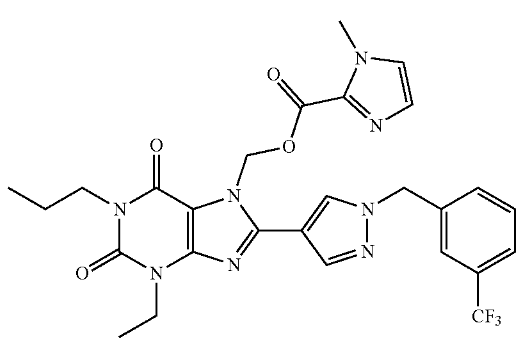 [SMILES: CCCn1c(=O)c2c(nc(-c3cnn(Cc4cccc(C(F)(F)F)c4)c3)n2COC(=O)c2nccn2C)n(CC)c1=O] | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl 1-methyl-1H-imidazole-2-carboxylate |

TABLE 2-continued

| Compound | Structure | Name |
|---|---|---|
| GG | 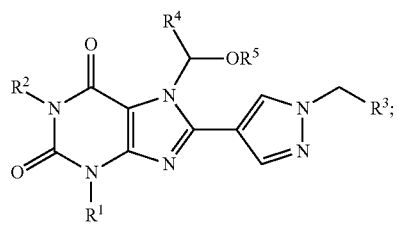 | (3-ethyl-2,6-dioxo-1-propyl-8-(1-(3-(trifluoromethyl)benzyl)-1H-pyrazol-4-yl)-1,2,3,6-tetrahydro-7H-purin-7-yl)methyl 1-methyl-1H-imidazole-4-carboxylate |

In one aspect, the present disclosure provides a compound represented by Formula (I):

(I)

or any pharmaceutically acceptable salt or solvate thereof, wherein:

$R^1$, $R^2$, $R^3$, and $R^5$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl; and $R^4$ is selected from substituted or unsubstituted $C_2$-$C_{10}$ alkyl, substituted or unsubstituted aryl, substituted or unsubstituted arylalkyl, substituted or unsubstituted cycloalkyl, and substituted or unsubstituted acyl.

In one embodiment, $R^1$ and $R^2$ are each independently lower alkyl. In one embodiment, $R^1$ is ethyl. In one embodiment, $R^2$ is n-propyl. In one embodiment, $R^3$ is 3-(trifluoromethyl)phenyl.

In one embodiment, the compound is represented by:

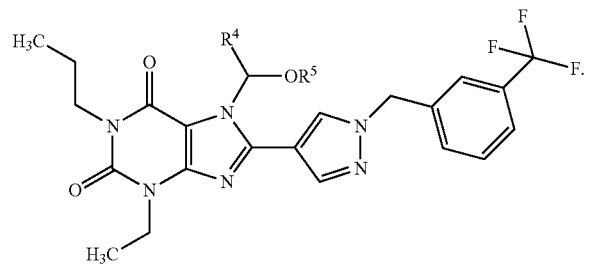

In one embodiment, the compound is represented by:

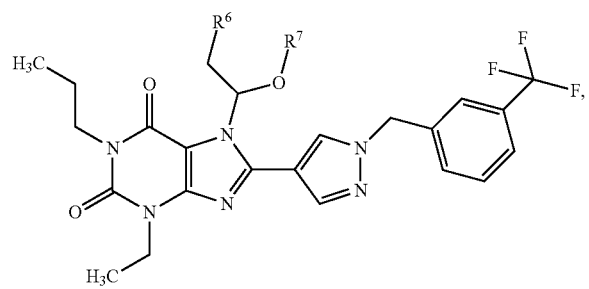

-continued

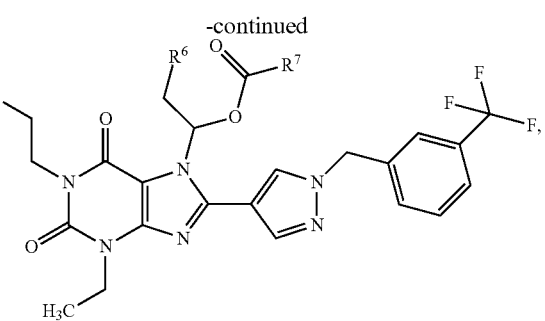

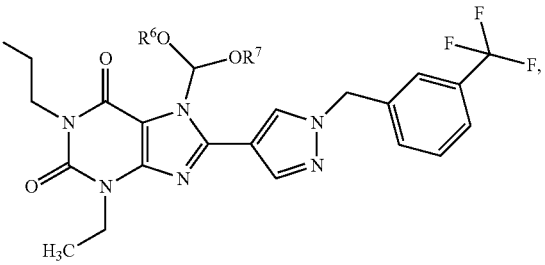

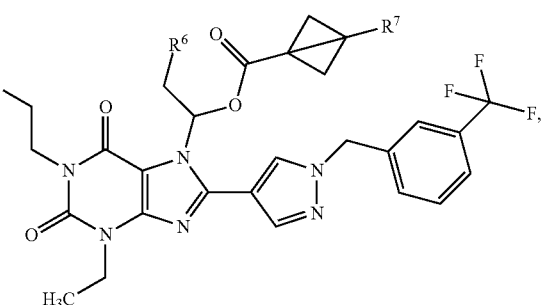

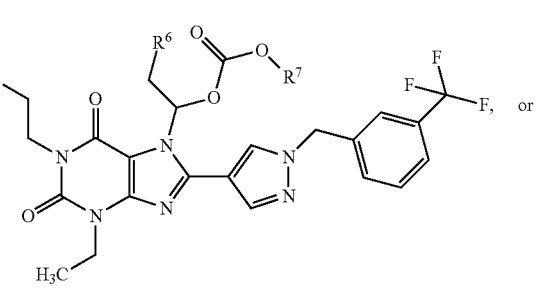

, or

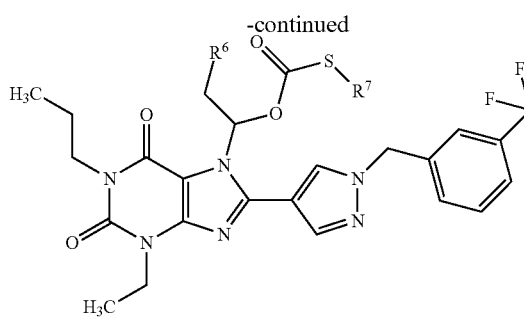

wherein:
R⁶ and R⁷ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, R⁶ and R⁷ are each independently hydrogen or lower alkyl. In a further embodiment, the compound is selected from the group consisting of

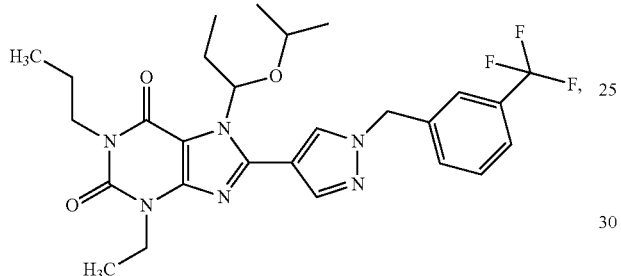

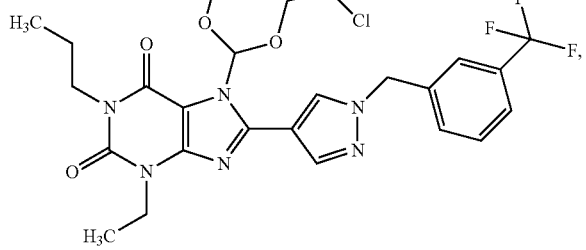

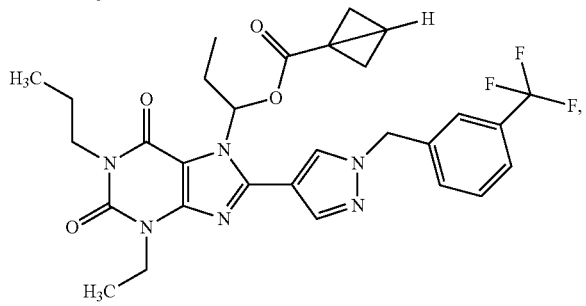

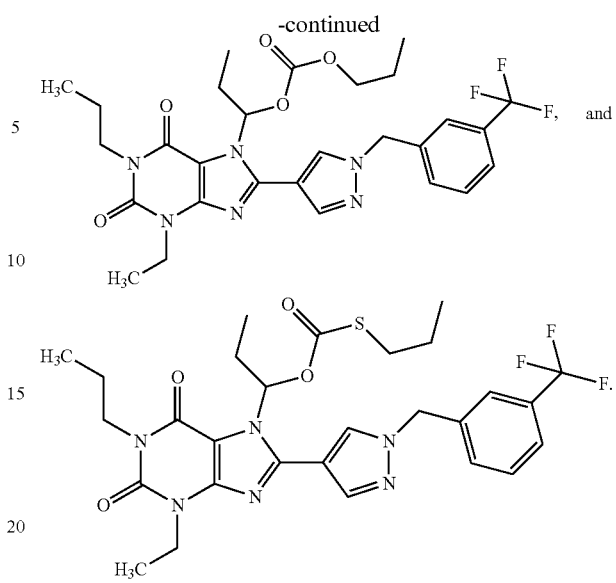

In one aspect, the present disclosure provides a compound of Formula (II):

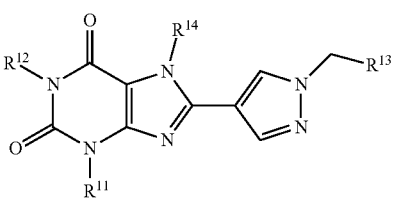

(II)

or any pharmaceutically acceptable salt or solvate thereof, wherein:
R¹¹, R¹², and R¹³ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl; and
R¹⁴ is substituted or unsubstituted cycloalkyl.

In one embodiment, R¹¹ and R¹² are each independently lower alkyl. In one embodiment, R¹¹ is ethyl. In one embodiment, R¹² is n-propyl. In one embodiment, R¹³ is 3-(trifluoromethyl)phenyl.

In one embodiment, the compound is represented by:

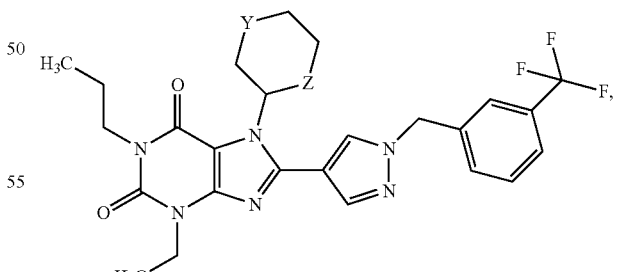

wherein:
Y is selected from O, S, substituted or unsubstituted —CH₂—, —NR¹⁵—, —S(O)₂—, and a bond;
Z is O or S; and
R¹⁵ is selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, the compound is represented by:

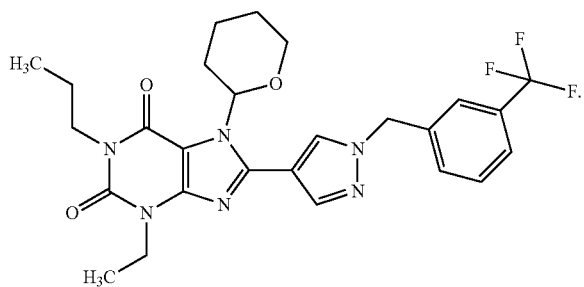

In one embodiment, the compound is represented by:

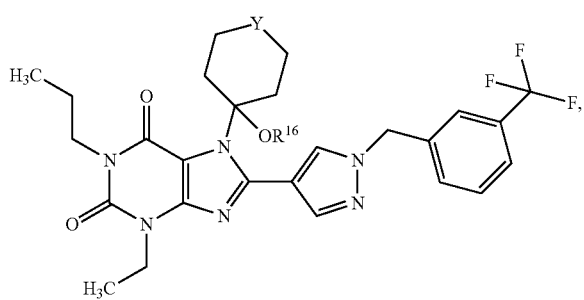

wherein:
Y is selected from O, S, substituted or unsubstituted —CH$_2$—, —NR$^{17}$—, —S(O)$_2$—, and a bond; and
R$^{16}$ and R$^{17}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, the compound is represented by:

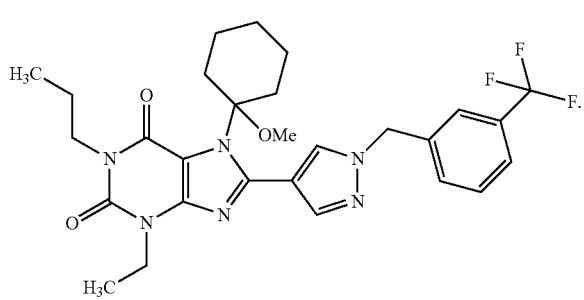 [SMILES: CCCn1c(=O)c2c(nc(-c3cnn(Cc4cccc(C(F)(F)F)c4)c3)n2C2(OC)CCCCC2)n(CC)c1=O]

In one aspect, the present disclosure provides a compound of Formula (III):

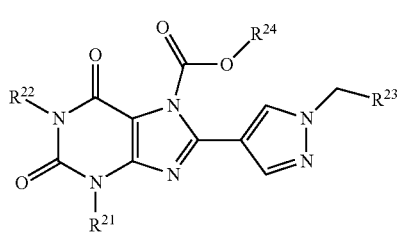

(III)

or any pharmaceutically acceptable salt or solvate thereof, wherein:
R$^{21}$, R$^{22}$, R$^{23}$, and R$^{24}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, R$^{21}$ and R$^{22}$ are each independently lower alkyl. In one embodiment, R$^{21}$ is ethyl. In one embodiment, R$^{22}$ is n-propyl. In one embodiment, R$^{23}$ is 3-(trifluoromethyl)phenyl.

In one embodiment, the compound is represented by:

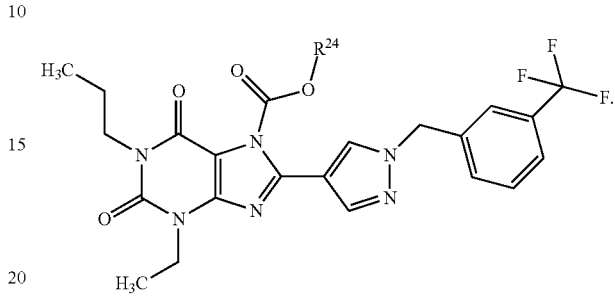

In one embodiment, the compound is selected from the group consisting of

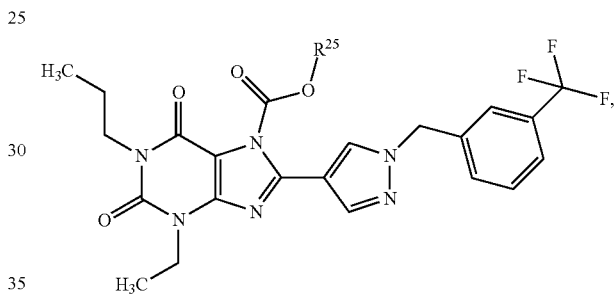

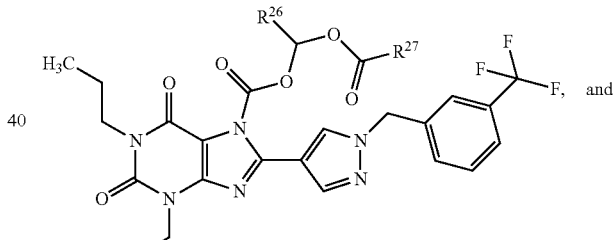
and

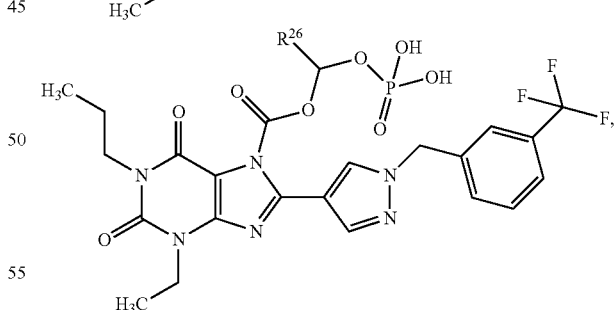

wherein:
R$^{25}$, R$^{26}$, and R$^{27}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, $^{25}$, R$^{26}$, and R$^{27}$ are each independently hydrogen or lower alkyl. In one embodiment, the compound is selected from the group consisting of

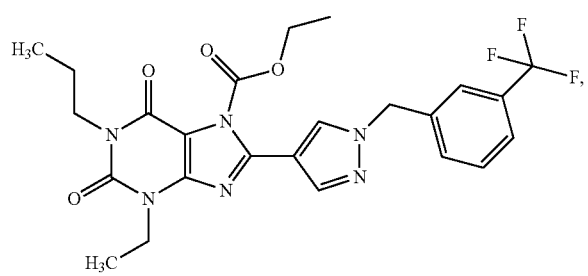

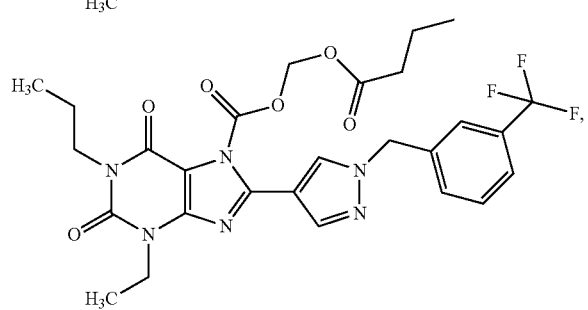

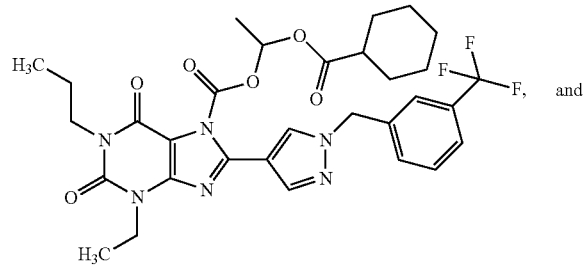

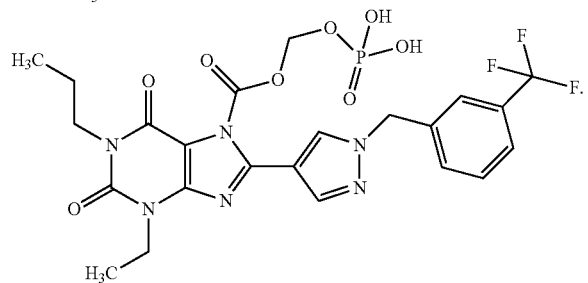

In one aspect, the present disclosure provides a compound of Formula (IV):

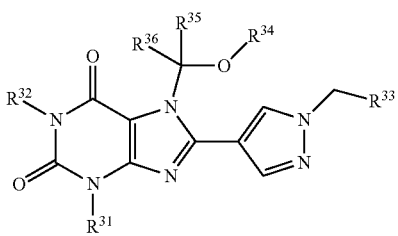

(IV)

or any pharmaceutically acceptable salt or solvate thereof, wherein:

$R^{31}$, $R^{32}$, $R^{33}$, $R^{34}$, $R^{35}$, and $R^{36}$ are each independently hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, $R^{31}$ and $R^{32}$ are each independently lower alkyl. In one embodiment, $R^{31}$ is ethyl. In one embodiment, $R^{32}$ is n-propyl. In one embodiment, $R^{33}$ is 3-(trifluoromethyl)phenyl. In one embodiment, the compound is represented by:

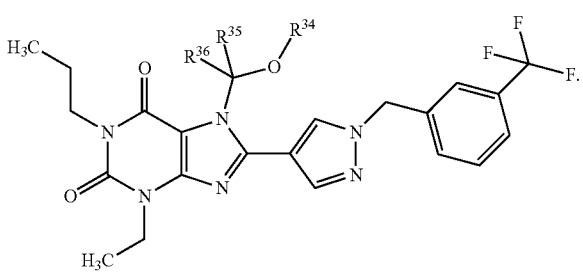

In one embodiment, the compound is represented by:

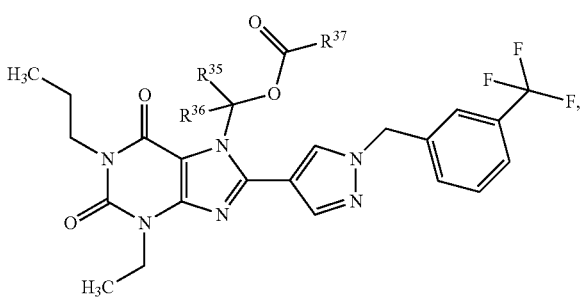

wherein:

$R^{37}$ is selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, $R^{35}$, $R^{36}$, and $R^{37}$ are each independently hydrogen or lower alkyl. In one embodiment, the compound is selected from the group consisting of

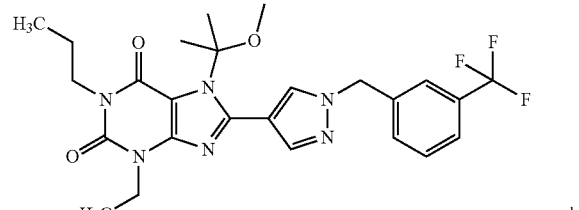

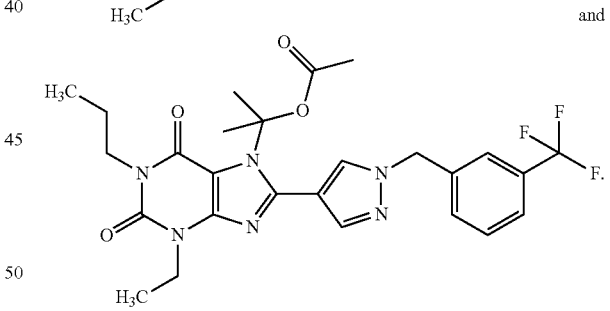

and

In one aspect, the present disclosure provides a compound of Formula (V):

(V)

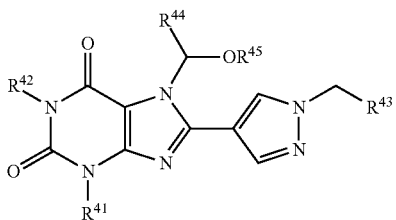

or any pharmaceutically acceptable salt or solvate thereof, wherein:

$R^{41}$, $R^{42}$, $R^{43}$ and $R^{44}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl; and $R^{45}$ is selected from hydrogen, substituted or unsubstituted alkyl, substituted or unsubstituted aryl, substituted or unsubstituted arylalkyl, and substituted or unsubstituted cycloalkyl.

In one embodiment, $R^{41}$ and $R^{42}$ are each independently selected from lower alkyl. In one embodiment, $R^{41}$ is ethyl. In one embodiment, $R^{42}$ is n-propyl. In one embodiment, $R^{43}$ is 3-(trifluoromethyl)phenyl. In one embodiment, when $R^{45}$ is not —C(O)$R^{47}$ or —P(O)(O$R^{47}$)$_2$, then $R^{47}$ is selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, the compound is represented by:

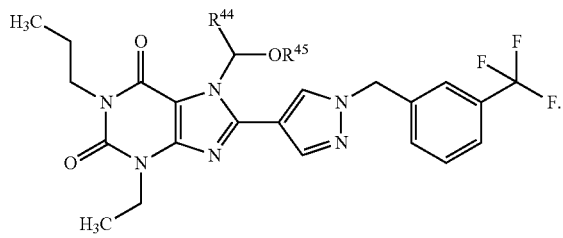

In one embodiment, the compound is selected from the group consisting of

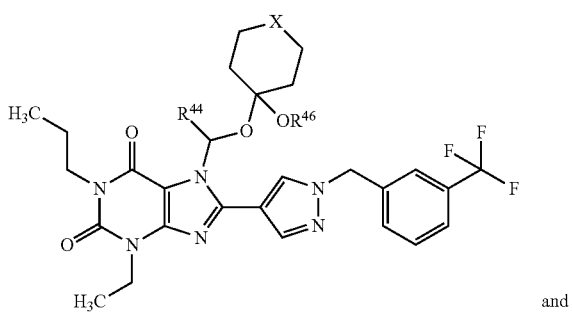

and

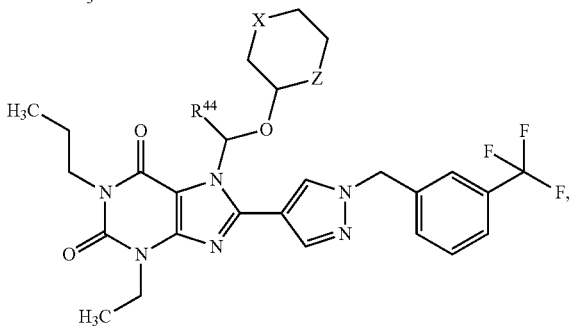

wherein:
$R^{46}$ is selected from hydrogen, substituted or unsubstituted alkyl, substituted or unsubstituted aryl, substituted or unsubstituted arylalkyl, substituted or unsubstituted cycloalkyl, and substituted or unsubstituted acyl;
X is selected from O, S, substituted or unsubstituted —CH$_2$—, —N$R^{48}$—, —S(O)$_2$—, and a bond;
Z is O or S; and
$R^{48}$ is selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, $R^{44}$ and $R^{46}$ are each independently hydrogen or lower alkyl. In one embodiment, the compound is selected from the group consisting of

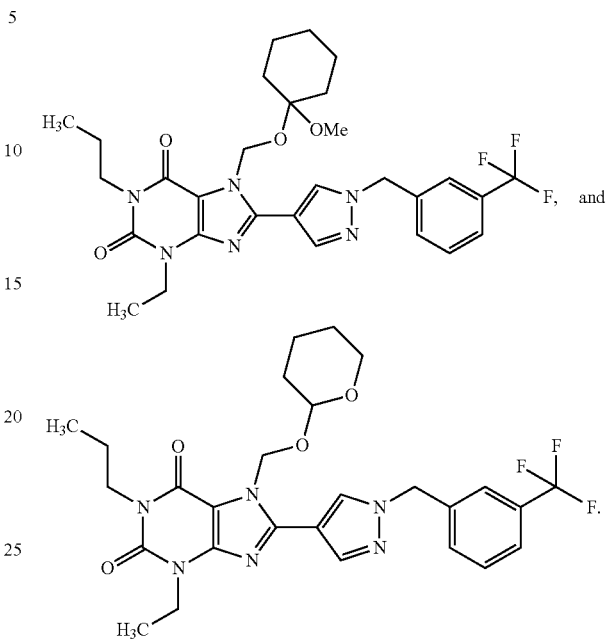

In one aspect, the present disclosure provides a compound of Formula (VI):

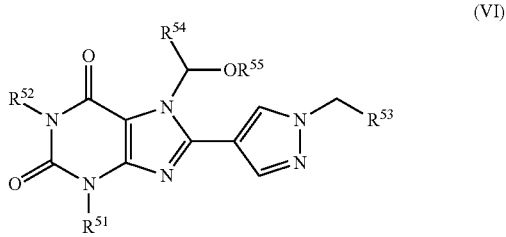

(VI)

or any pharmaceutically acceptable salt or solvate thereof, wherein:
$R^{51}$, $R^{52}$, $R^{53}$, and $R^{55}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl; and
$R^{54}$ is hydrogen or methyl.

In one embodiment, $R^{51}$ and $R^{52}$ are each independently lower alkyl. In one embodiment, $R^{51}$ is ethyl. In one embodiment, $R^{52}$ is n-propyl. In one embodiment, $R^{53}$ is 3-(trifluoromethyl)phenyl.

In one embodiment, the compound is represented by:

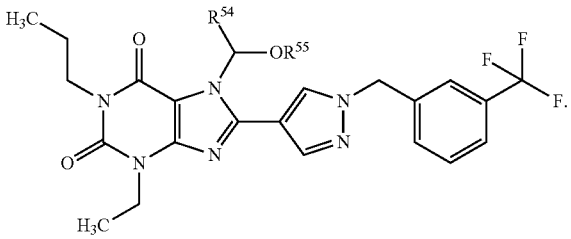

In one embodiment, the compound is selected from the group consisting of:

71

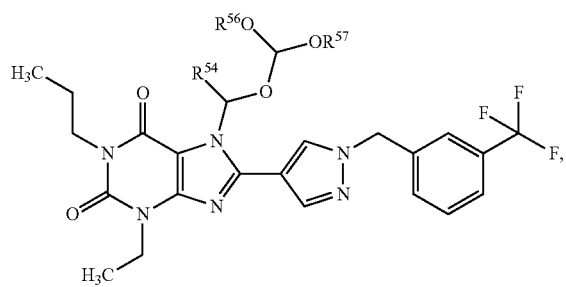

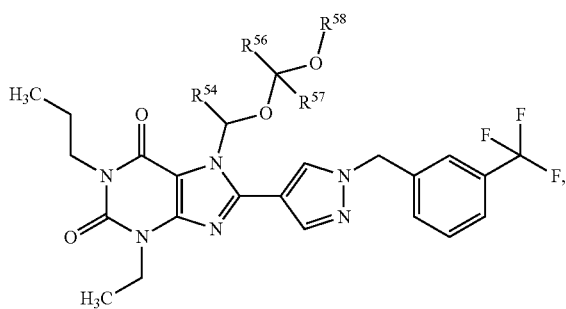

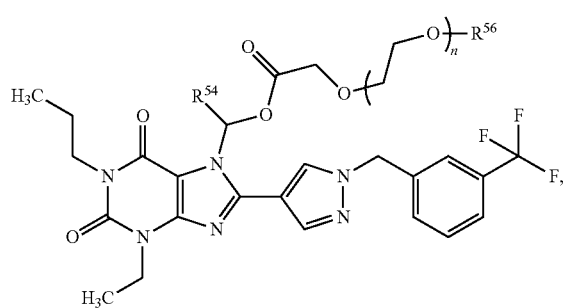

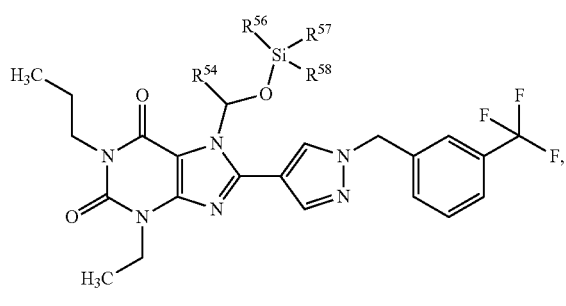

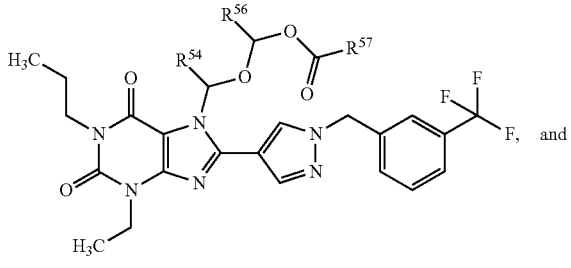, and

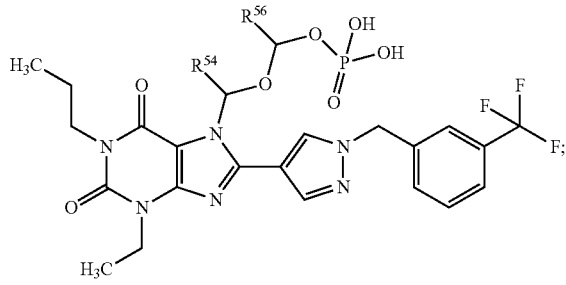

72 wherein:

R⁵⁶, R⁵⁷, and R⁵⁸ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.

In one embodiment, R⁵⁶, R⁵⁷, and R⁵⁸ are each independently hydrogen or lower alkyl. In one embodiment, the compound is selected from the group consisting of:

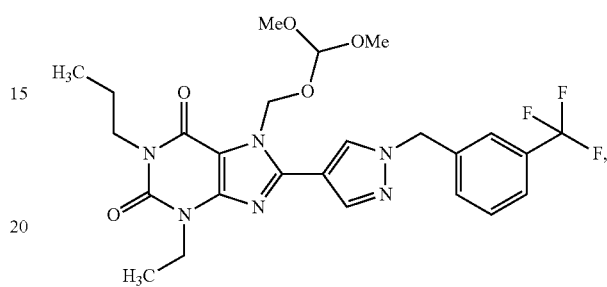

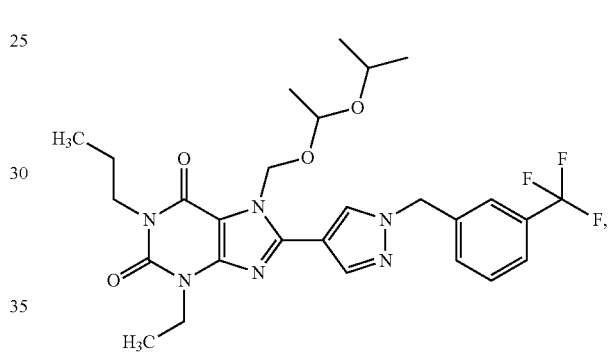

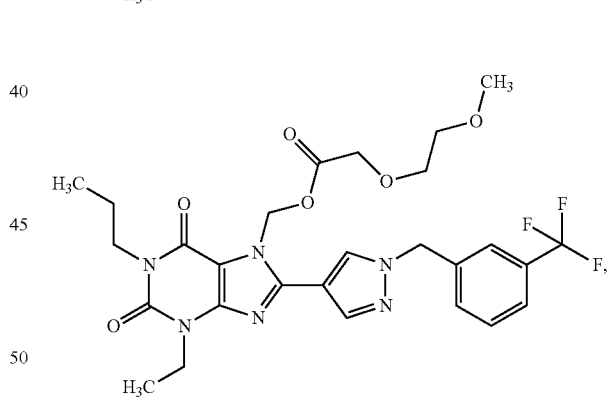

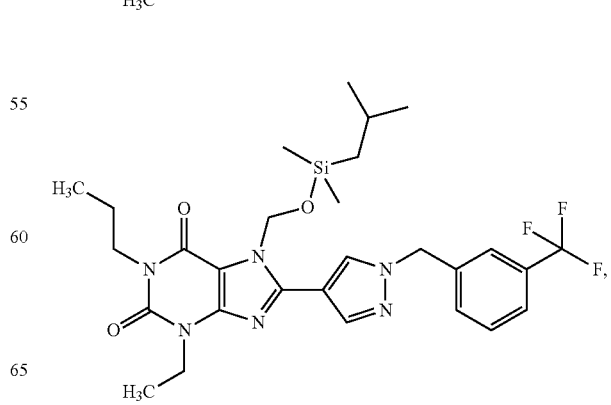

-continued

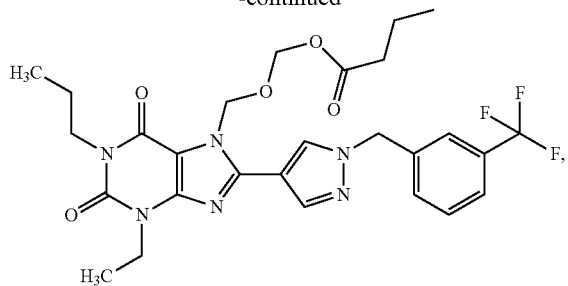

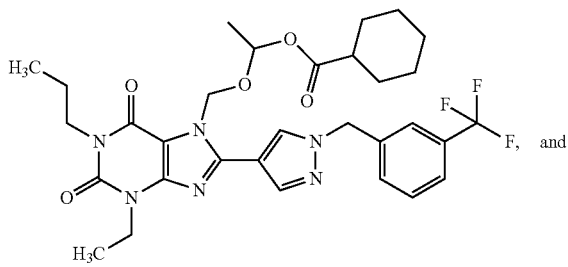

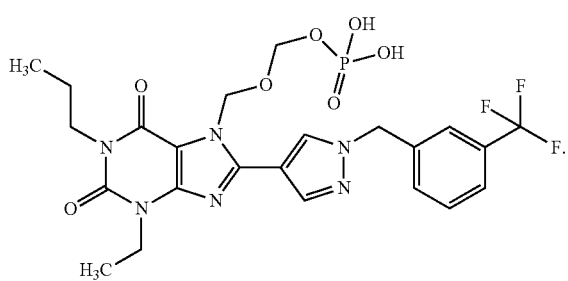 [SMILES: CCCn1c(=O)c2c(nc(-c3cnn(Cc4cccc(C(F)(F)F)c4)c3)n2COCOP(=O)(O)O)n(CC)c1=O]

In one aspect, the present disclosure provides a compound of Formula (VII):

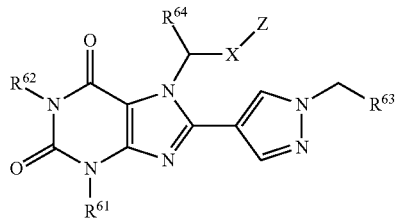

(VII)

or any pharmaceutically acceptable salt or solvate thereof, wherein:
X is selected from O, S, substituted or unsubstituted —CH$_2$—, —NR$^{65}$—, —S(O)$_2$—, and a bond;
Z is —SO$_2$OH or —S(O)OH; and
R$^{61}$, R$^{62}$, R$^{63}$, R$^{64}$, and R$^{65}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.
In one embodiment, R$^{61}$ and R$^{62}$ are each independently lower alkyl. In one embodiment, R$^{61}$ is ethyl. In one embodiment, R$^{62}$ is n-propyl. In one embodiment, R$^{63}$ is 3-(trifluoromethyl)phenyl.

In one embodiment, the compound is represented by:

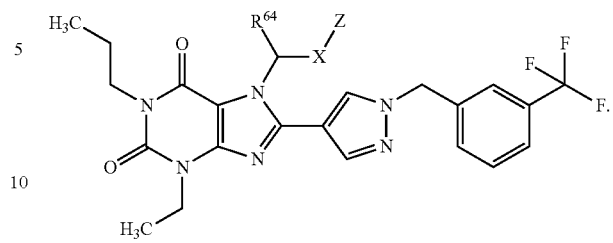

In one embodiment, R$^{64}$ is hydrogen or lower alkyl. In one embodiment, the compound is selected from the group consisting of

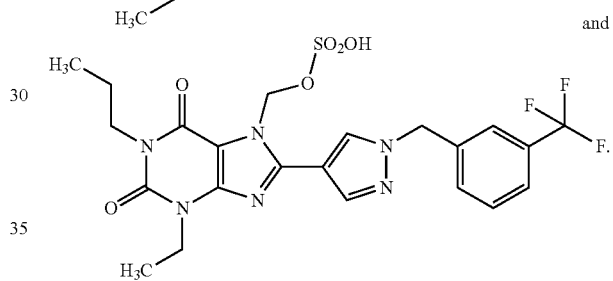

and

In one aspect, the present disclosure provides a compound of Formula (VIII):

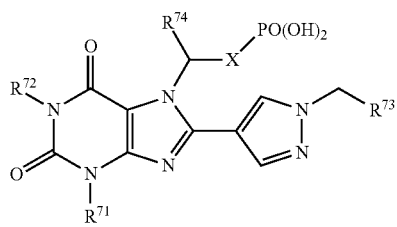

(VIII)

or any pharmaceutically acceptable salt or solvate thereof, wherein:
X is selected from S, substituted or unsubstituted —CH$_2$—, —NR$^{75}$—, and —S(O)$_2$—; and
R$^{71}$, R$^{72}$, R$^{73}$, R$^{74}$ and R$^{75}$ are each independently selected from hydrogen, substituted or unsubstituted alkyl, substituted or unsubstituted aryl, substituted or unsubstituted arylalkyl, substituted or unsubstituted cycloalkyl, and substituted or unsubstituted acyl.
In one embodiment, R$^{71}$ and R$^{72}$ are each independently lower alkyl. In one embodiment, R$^{71}$ is ethyl. In one embodiment, R$^{72}$ is n-propyl. In one embodiment, R$^{73}$ is 3-(trifluoromethyl)phenyl.

In one embodiment, the compound is represented by:

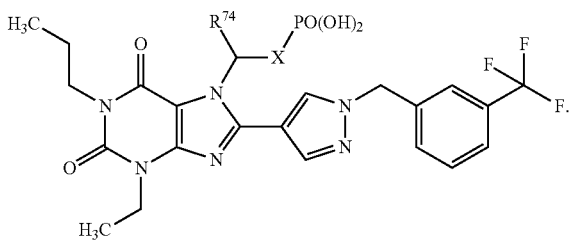

In one embodiment, $R^{74}$ is hydrogen or lower alkyl. In one embodiment, the compound is represented by:

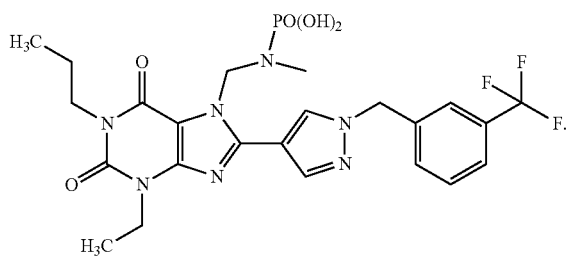

Disclosed herein are compounds of Formula (1):

Formula (1)

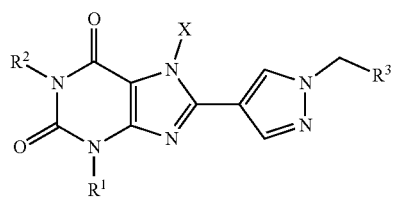

or any pharmaceutically acceptable salt or solvate thereof, wherein:

$R^1$, $R^2$, and $R^3$, are each independently H, substituted or unsubstituted alkyl, or substituted or unsubstituted aryl;

X is H, amino, halo, substituted or unsubstituted alkyl, substituted or unsubstituted aryl, substituted or unsubstituted arylalkyl, substituted or unsubstituted cycloalkyl, or substituted or unsubstituted acyl.

In some cases, $R^1$ is unsubstituted alkyl, preferably ethyl. In some cases, $R^2$ is unsubstituted alkyl, preferably propyl. In some cases, $R^3$ is substituted aryl, preferably 3-(trifluoromethyl)phenyl. In some cases, the compound can be a compound of Formula (2):

Formula (2)

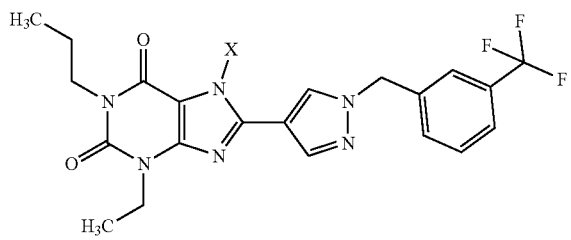

or any pharmaceutically acceptable salt or solvate thereof, wherein X is H, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, the prodrug is the compound of

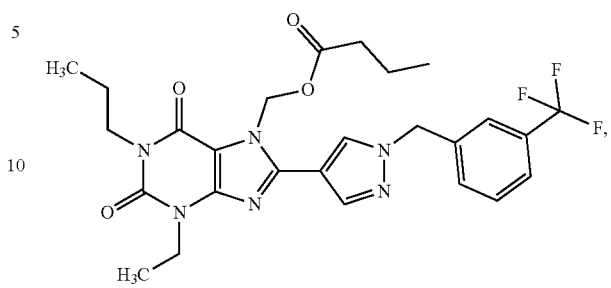

or any pharmaceutically acceptable salt or solvate thereof.

In one example, the prodrug is the compound of

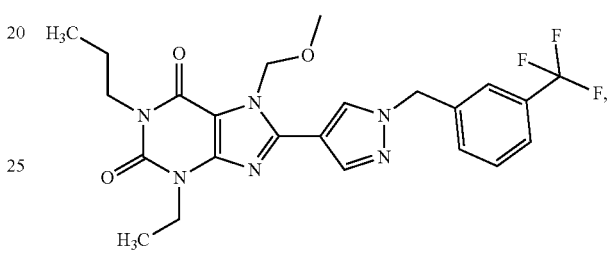

or any pharmaceutically acceptable salt or solvate thereof.

In some cases, disclosed herein are compounds of Formula (3):

Formula (3)

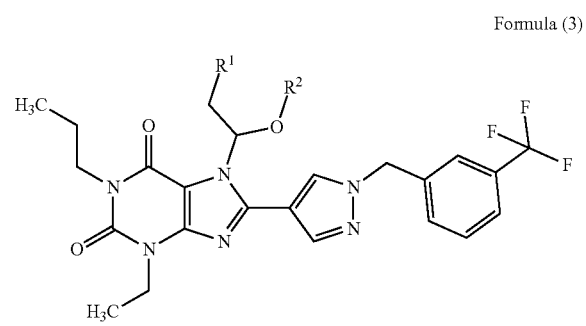

or any pharmaceutically acceptable salt or solvate thereof, wherein:

$R^1$ and $R^2$ are each independently amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

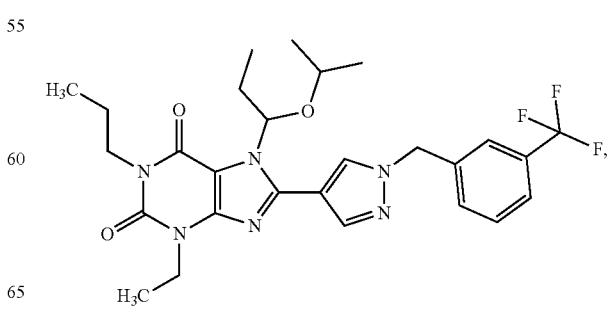

or any pharmaceutically acceptable salt or solvate thereof.

In some cases, disclosed herein are compounds of Formula (4):

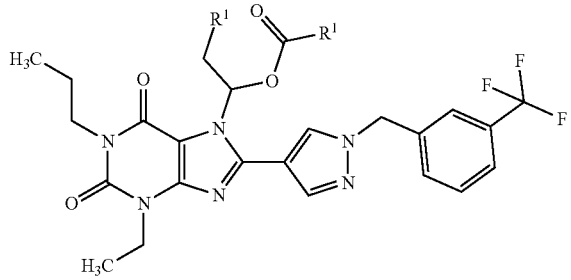

Formula (4)

or any pharmaceutically acceptable salt or solvate thereof, wherein:

$R^1$, and $R^2$, are each independently amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

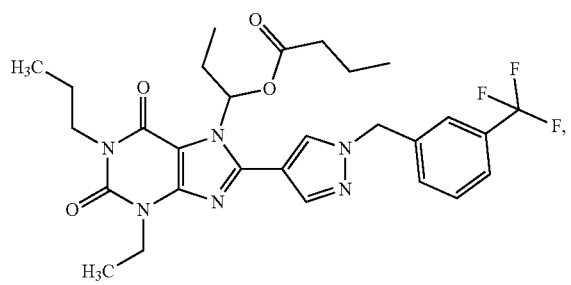 [SMILES: CCCC(=O)OC(CC)n1c(-c2cnn(Cc3cccc(C(F)(F)F)c3)c2)nc2c1c(=O)n(CCC)c(=O)n2CC]

or any pharmaceutically acceptable salt or solvate thereof.

In some cases, disclosed herein are compounds of Formula (5):

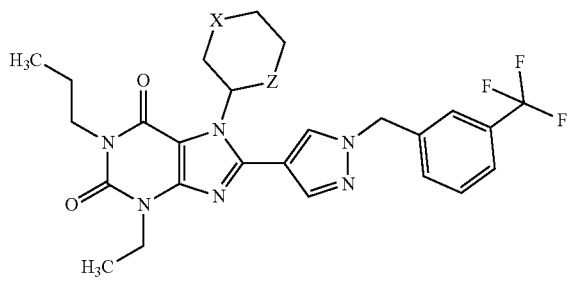 [SMILES: CCCn1c(=O)c2c(nc(-c3cnn(Cc4cccc(C(F)(F)F)c4)c3)n2C2CCCCO2)n(CC)c1=O]

Formula (5)

or any pharmaceutically acceptable salt or solvate thereof, wherein:

X is O, S, substituted or unsubstituted —CH$_2$—, —NR'—, —S(O)$_2$—, or a bond;

Z is O or S; and

R' is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

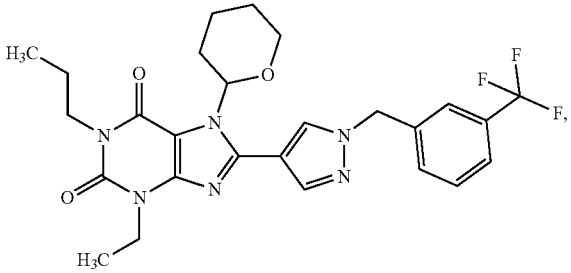

or any pharmaceutically acceptable salt or solvate thereof.

In some cases, disclosed herein are compounds of Formula (6):

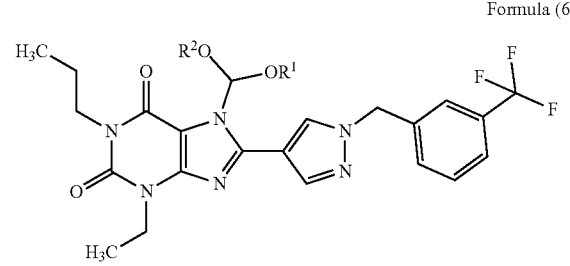

Formula (6)

or any pharmaceutically acceptable salt or solvate thereof, wherein:

$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

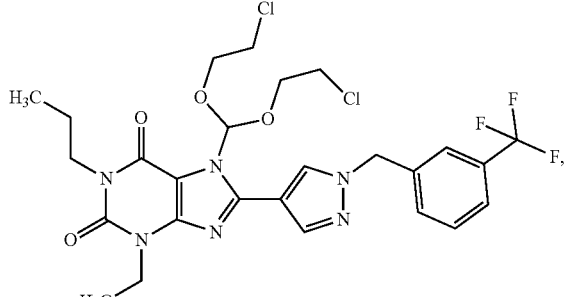

or any pharmaceutically acceptable salt or solvate thereof.

In some cases, disclosed herein are compounds of Formula (7):

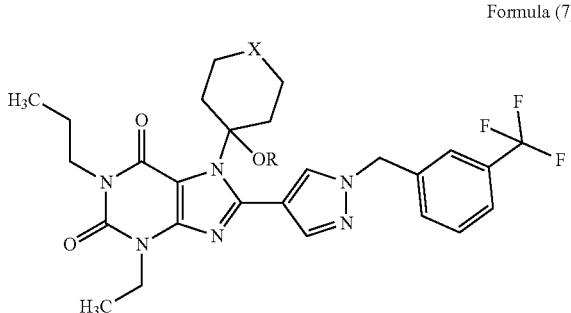

Formula (7)

or any pharmaceutically acceptable salt or solvate thereof, wherein:

X is O, S, substituted or unsubstituted —CH$_2$—, —NR'—, —S(O)$_2$—, and

R and R' are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

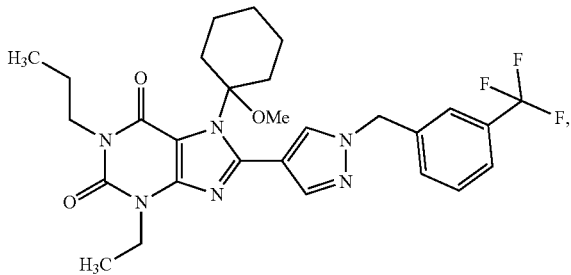 [SMILES: CCCn1c(=O)c2c(nc(-c3cnn(Cc4cccc(C(F)(F)F)c4)c3)n2C2(OC)CCCCC2)n(CC)c1=O]

or any pharmaceutically acceptable salt or solvate thereof.

In some cases, disclosed herein are compounds of Formula (8):

Formula (8)

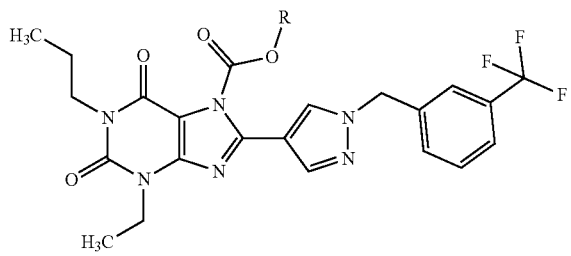

or any pharmaceutically acceptable salt or solvate thereof, wherein:
R is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

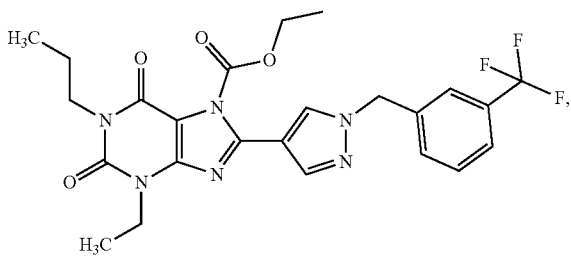 [SMILES: CCCn1c(=O)c2c(nc(-c3cnn(Cc4cccc(C(F)(F)F)c4)c3)n2C(=O)OCC)n(CC)c1=O]

or any pharmaceutically acceptable salt or solvate thereof.

In some cases, disclosed herein are compounds of Formula (9):

Formula (9)

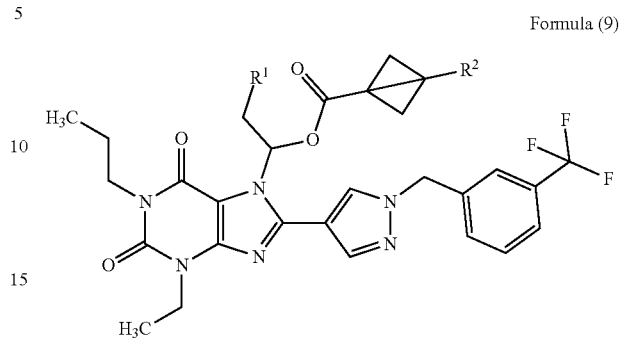

or any pharmaceutically acceptable salt or solvate thereof, wherein:
$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

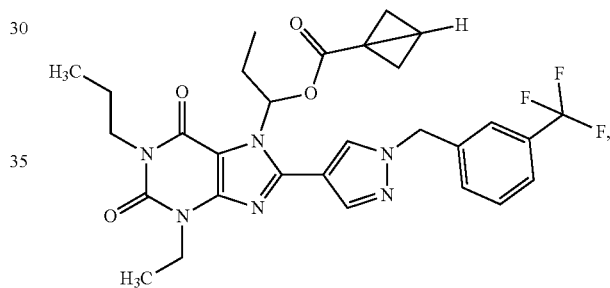

or any pharmaceutically acceptable salt or solvate thereof.

In some cases, disclosed herein are compounds of Formula (10):

Formula (10)

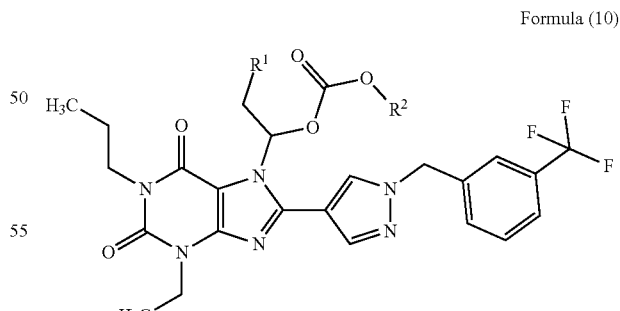

or any pharmaceutically acceptable salt or solvate thereof, wherein:
$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

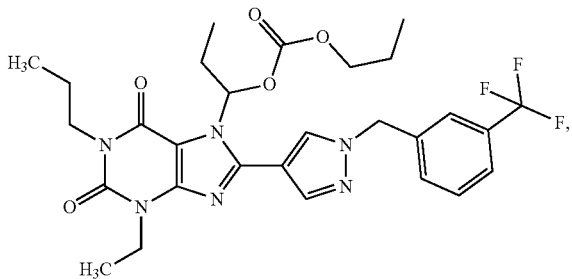 [SMILES: CCCOC(=O)OC(CC)n1c(-c2cnn(Cc3cccc(C(F)(F)F)c3)c2)nc2c1c(=O)n(CCC)c(=O)n2CC]

or any pharmaceutically acceptable salt or solvate thereof.

In some cases, disclosed herein are compounds of Formula (11):

Formula (11)

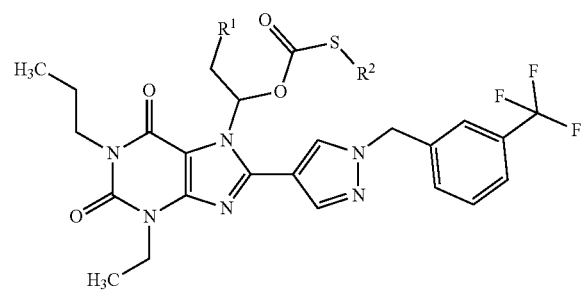

or any pharmaceutically acceptable salt or solvate thereof, wherein:
$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

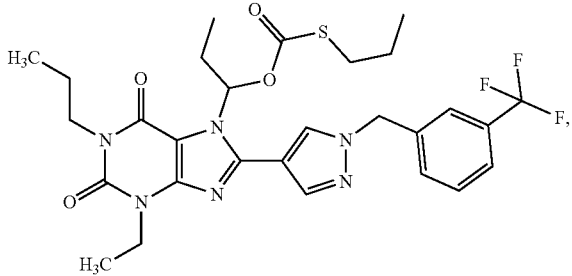

or any pharmaceutically acceptable salt or solvate thereof.

In some cases, disclosed herein are compounds of Formula (12):

Formula (12)

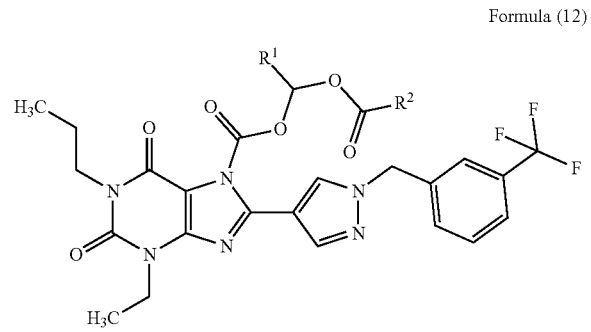

or any pharmaceutically acceptable salt or solvate thereof, wherein:
$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

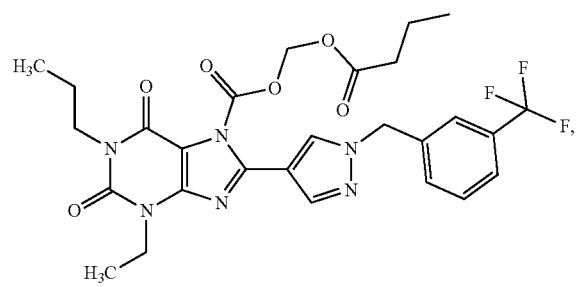 [SMILES: CCCC(=O)OCOC(=O)n1c(-c2cnn(Cc3cccc(C(F)(F)F)c3)c2)nc2c1c(=O)n(CCC)c(=O)n2CC]

or any pharmaceutically acceptable salt or solvate thereof.

In another example, disclosed herein is the compound:

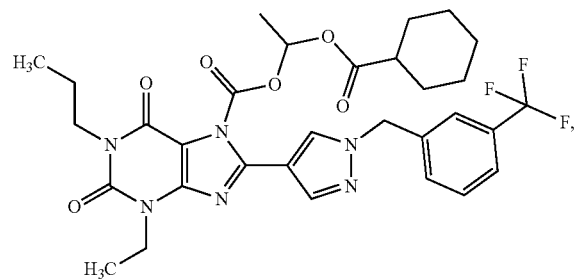 [SMILES: CCCn1c(=O)c2c(nc(-c3cnn(Cc4cccc(C(F)(F)F)c4)c3)n2C(=O)OC(C)OC(=O)C2CCCCC2)n(CC)c1=O]

or any pharmaceutically acceptable salt or solvate thereof.

In some cases, disclosed herein are compounds of Formula (13):

Formula (13)

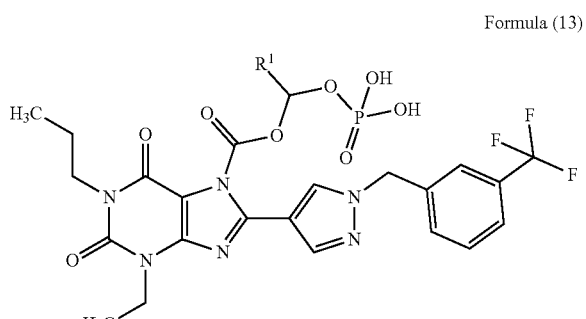

or any pharmaceutically acceptable salt or solvate thereof, wherein:
$R^1$ is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

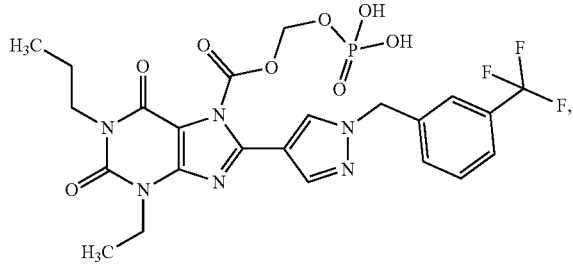 [SMILES: CCCn1c(=O)c2c(nc(-c3cnn(Cc4cccc(C(F)(F)F)c4)c3)n2C(=O)OCOP(=O)(O)O)n(CC)c1=O]

or any pharmaceutically acceptable salt or solvate thereof.

In some cases, disclosed herein are compounds of Formula (14):

Formula (14)

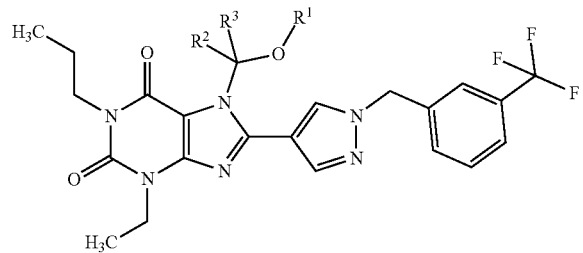

or any pharmaceutically acceptable salt or solvate thereof, wherein:
$R^1$, $R^2$, and $R^3$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

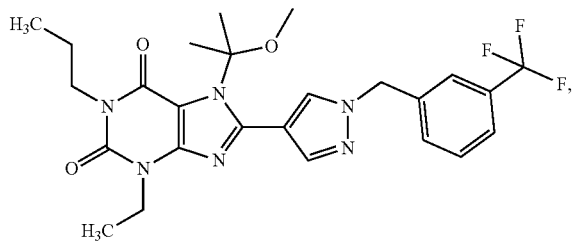 [SMILES: CCCn1c(=O)c2c(nc(-c3cnn(Cc4cccc(C(F)(F)F)c4)c3)n2C(C)(C)OC)n(CC)c1=O]

or any pharmaceutically acceptable salt or solvate thereof.

In some cases, disclosed herein are compounds of Formula (15):

Formula (15)

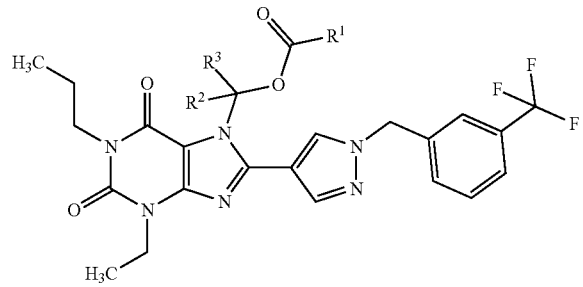 [SMILES: CCCn1c(=O)c2c(nc(-c3cnn(Cc4cccc(C(F)(F)F)c4)c3)n2C(C)(C)OC(C)=O)n(CC)c1=O]

or any pharmaceutically acceptable salt or solvate thereof, wherein:
$R^1$, $R^2$, and $R^3$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

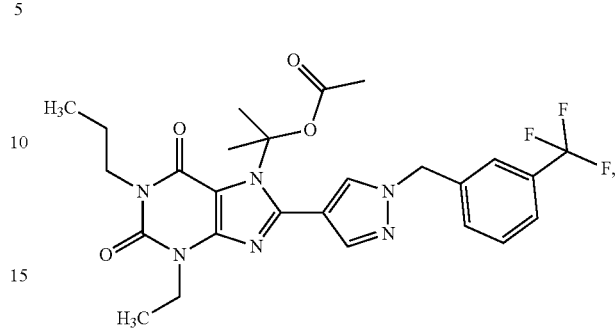

or any pharmaceutically acceptable salt or solvate thereof.

In some cases, disclosed herein are compounds of Formula (16):

Formula (16)

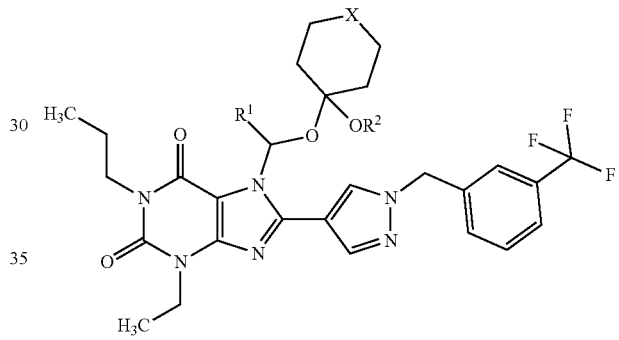

or any pharmaceutically acceptable salt or solvate thereof, wherein:
X is O, S, substituted or unsubstituted —CH$_2$—, —NR'—, —S(O)$_2$—, or a bond; and
$R^1$, $R^2$, and R', are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

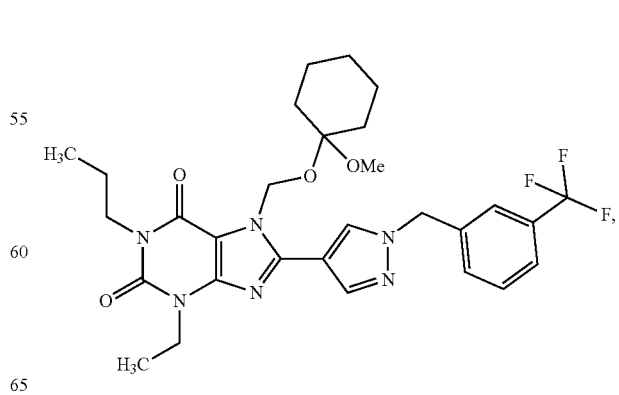

or any pharmaceutically acceptable salt or solvate thereof.

In some cases, disclosed herein are compounds of Formula (17):

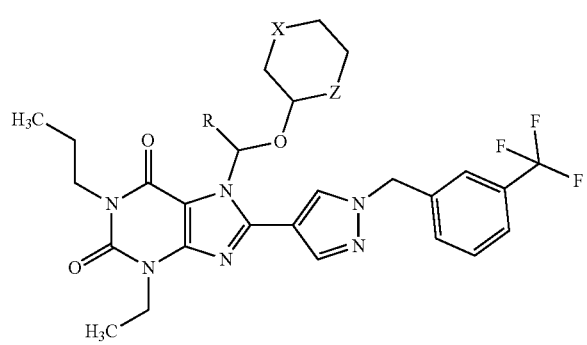

Formula (17)

or any pharmaceutically acceptable salt or solvate thereof, wherein:

X is O, S, substituted or unsubstituted —CH$_2$—, —NR'—, —S(O)$_2$—, or a bond;

Z is O or S; and

R is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

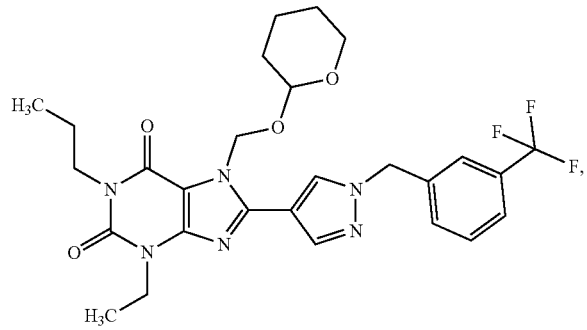 [SMILES: CCCn1c(=O)c2c(nc(-c3cnn(Cc4cccc(C(F)(F)F)c4)c3)n2COC2CCCCO2)n(CC)c1=O]

or any pharmaceutically acceptable salt or solvate thereof.

In some cases, disclosed herein are compounds of Formula (18):

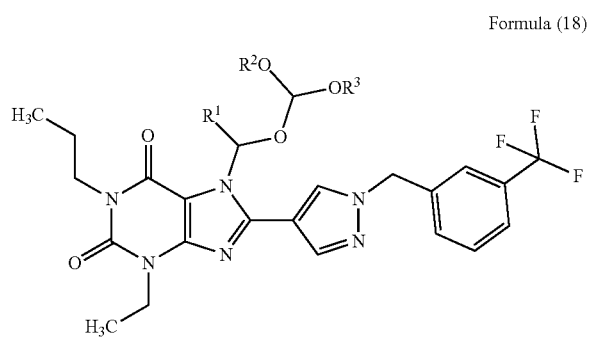

Formula (18)

or any pharmaceutically acceptable salt or solvate thereof, wherein:

$R^1$, $R^2$, and $R^3$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

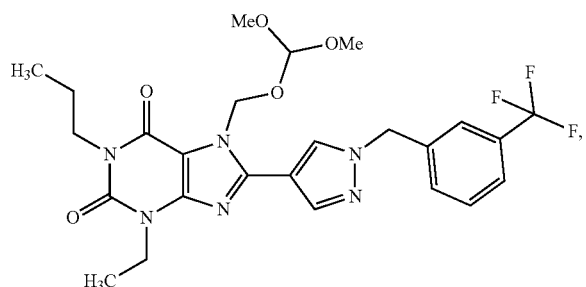

or any pharmaceutically acceptable salt or solvate thereof.

In some cases, disclosed herein are compounds of Formula (19):

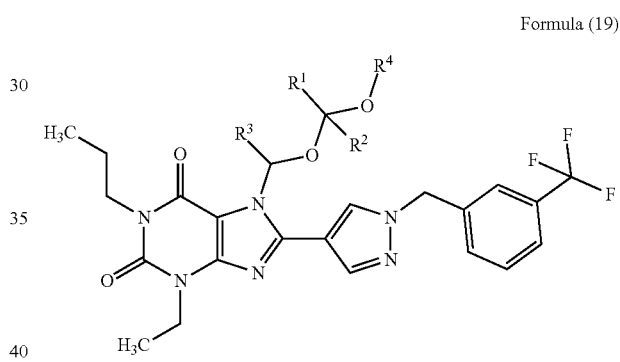

Formula (19)

or any pharmaceutically acceptable salt or solvate thereof, wherein:

$R^1$, $R^2$, $R^3$, and $R^4$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

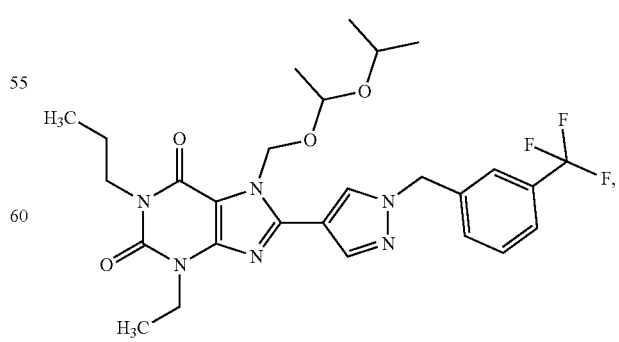

or any pharmaceutically acceptable salt or solvate thereof.

In some cases, disclosed herein are compounds of Formula (20):

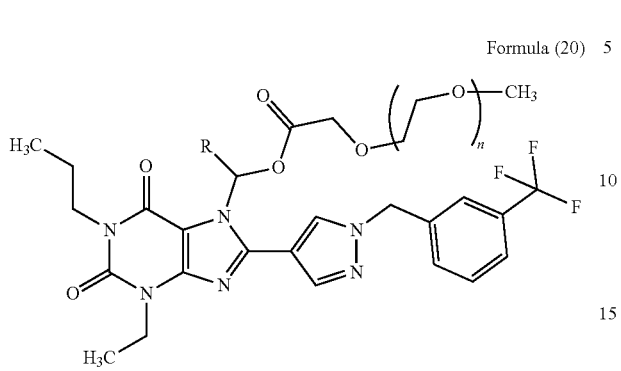

Formula (20)

or any pharmaceutically acceptable salt or solvate thereof, wherein:
R is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl; and n is any of 1-5.

In one example, disclosed herein is the compound:

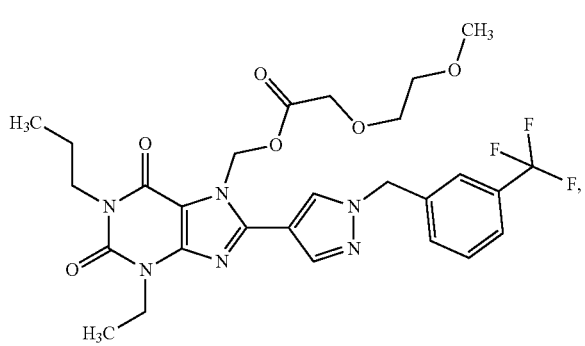 [SMILES: CCCn1c(=O)c2c(nc(-c3cnn(Cc4cccc(C(F)(F)F)c4)c3)n2COC(=O)COCCOC)n(CC)c1=O]

or any pharmaceutically acceptable salt or solvate thereof.

In some cases, disclosed herein are compounds of Formula (21):

Formula (21)

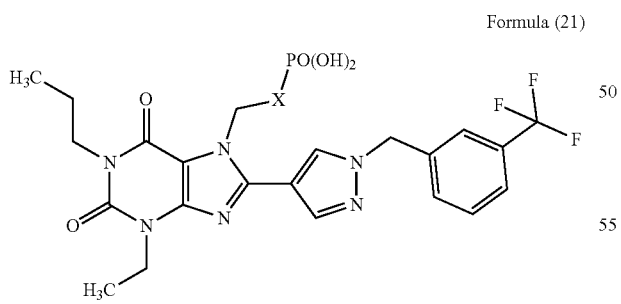

or any pharmaceutically acceptable salt or solvate thereof, wherein:
X is O, S, substituted or unsubstituted —CH$_2$—, —NR'—, or —S(O)$_2$—; and
R' is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

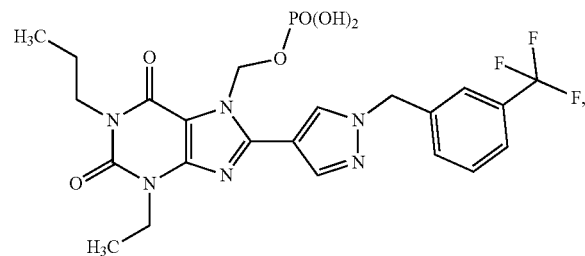

or any pharmaceutically acceptable salt or solvate thereof.

In one example, disclosed herein is the compound:

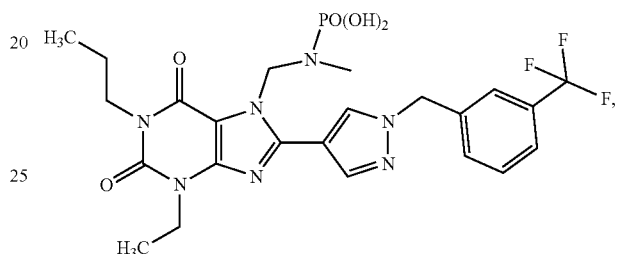

or any pharmaceutically acceptable salt or solvate thereof.

In one example, disclosed herein is the compound:

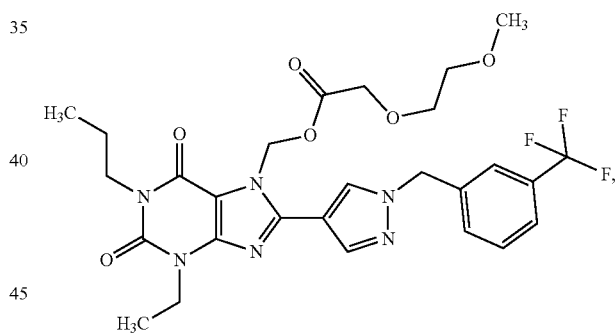

or any pharmaceutically acceptable salt or solvate thereof.

In some cases, disclosed herein are compounds of Formula (22):

Formula (22)

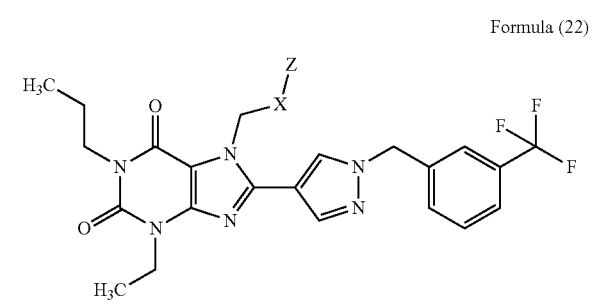

or any pharmaceutically acceptable salt or solvate thereof, wherein:

X is O, S, substituted or unsubstituted —CH$_2$—, —NR'—, —S(O)$_2$—, or a bond;

Z is —SO$_2$OH or —S(O)OH; and

R' is hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

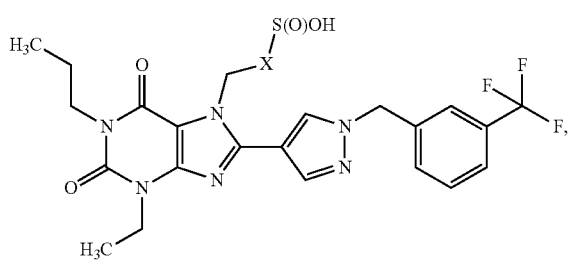

or any pharmaceutically acceptable salt or solvate thereof.

In one example, disclosed herein is the compound:

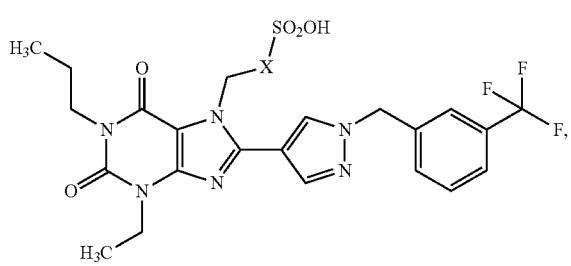

or any pharmaceutically acceptable salt or solvate thereof.

In some cases, disclosed herein are compounds of Formula (23):

Formula (23)

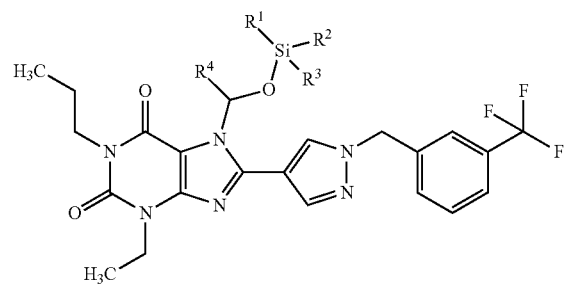

or any pharmaceutically acceptable salt or solvate thereof, wherein:

R$^1$, R$^2$, R$^3$, and R$^4$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

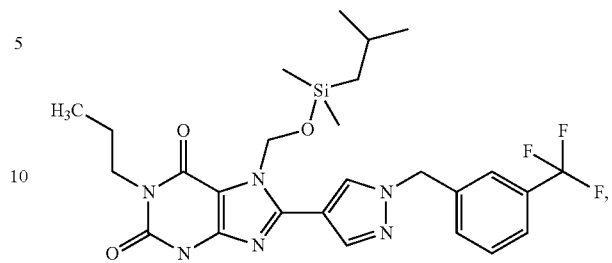

or any pharmaceutically acceptable salt or solvate thereof.

In some cases, disclosed herein are compounds of Formula (24):

Formula (24)

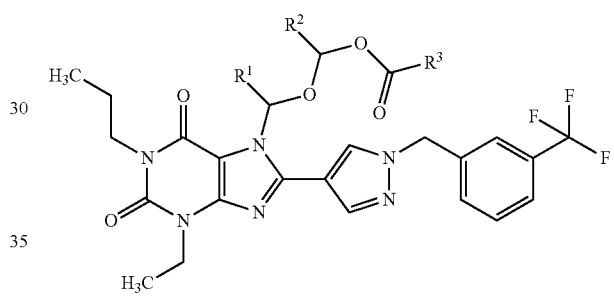

or any pharmaceutically acceptable salt or solvate thereof, wherein:

R', R$^2$, and R$^3$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

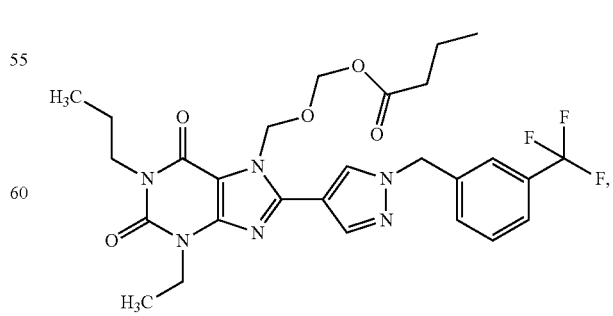

or any pharmaceutically acceptable salt or solvate thereof.

In one example, disclosed herein is the compound:

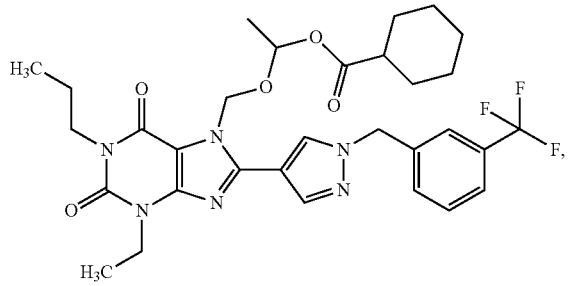 [SMILES: CCCn1c(=O)c2c(nc(-c3cnn(Cc4cccc(C(F)(F)F)c4)c3)n2COC(C)OC(=O)C2CCCCC2)n(CC)c1=O]

or any pharmaceutically acceptable salt or solvate thereof.

In some cases, disclosed herein are compounds of Formula (25):

Formula (25)

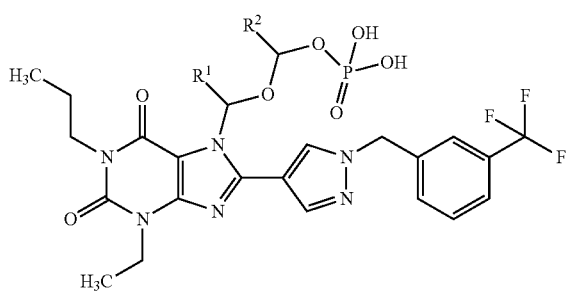

or any pharmaceutically acceptable salt or solvate thereof, wherein:

$R^1$, and $R^2$, are each independently hydrogen, amino, halo, substituted or unsubstituted alkyl, substituted or unsubstituted aryl, substituted or unsubstituted arylalkyl, substituted or unsubstituted cycloalkyl, or substituted or unsubstituted acyl.

In one example, disclosed herein is the compound:

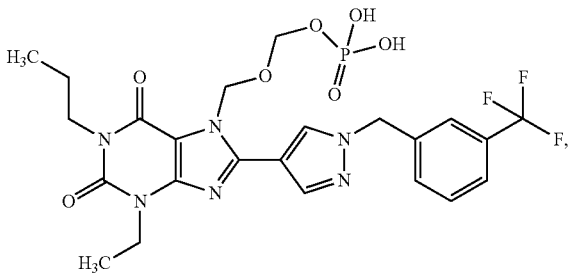 [SMILES: CCCn1c(=O)c2c(nc(-c3cnn(Cc4cccc(C(F)(F)F)c4)c3)n2COCOP(=O)(O)O)n(CC)c1=O]

or a pharmaceutically acceptable salt or solvate thereof.

In some cases, also disclosed herein are compounds selected from the group consisting of:

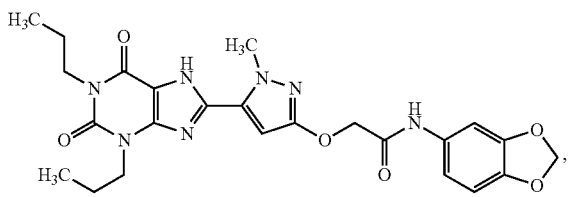

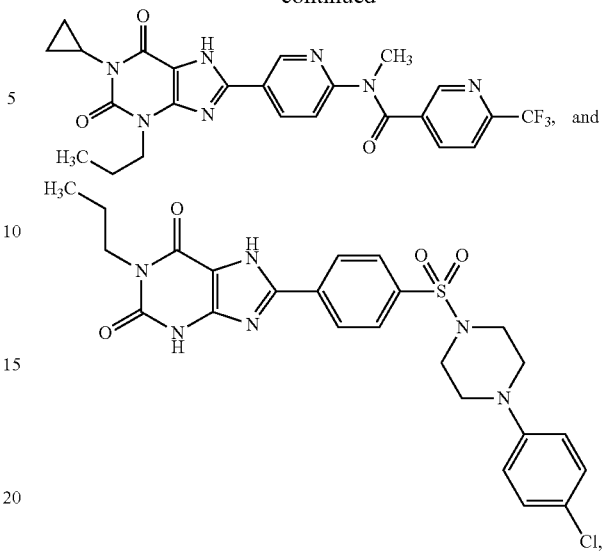

or any pharmaceutically acceptable salt or solvate thereof. Prodrugs of these $A_{2B}$ adenosine receptor antagonists can be designed and synthesized in a similar way to the prodrugs of the Compound 1 by substituting the xanthine at 7-position.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action.

Pharmaceutical compositions incorporating a compound described herein may take any physical form that is pharmaceutically acceptable. Pharmaceutical compositions for oral administration are particularly preferred. For example, such pharmaceutical compositions include, but are not limited to, tablets, troches, lozenges, aqueous or oily suspensions, dispersible powders or granules, emulsions, hard or soft capsules, or syrups or elixirs.

Known methods of formulating used in pharmaceutical science may be followed to prepare pharmaceutical compositions. All of the usual types of compositions are contemplated, including, but not limited to, tablets, chewable tablets, capsules, and solutions.

Capsules may be prepared by mixing a compound described herein with a suitable diluent and filling the proper amount of the mixture in capsules. Tablets may be prepared by direct compression, by wet granulation, or by dry granulation. Their formulations usually incorporate diluents, binders, lubricants, and disintegrators, as well as the compound described herein as an active therapeutic agent. A lubricant in a tablet formulation may help prevent the tablet and punches from sticking in the die. Tablet disintegrators are substances that swell when wetted to break up the tablet and release the compound. Enteric formulations are often used to protect an active ingredient from the strongly acidic contents of the stomach and to delay disintegration and absorption in the gastrointestinal tract. Such formulations are created by coating a solid dosage form with a film of a polymer that is insoluble in acid environments, and soluble in basic environments. Tablets are often coated with sugar as a flavor and sealant.

EXAMPLES

The following examples are provided for illustrative purposes only and not to limit the scope of the claims provided herein.

Example 1—Synthesis of Exemplary Compound A

Compound A can be synthesized according to the scheme below.

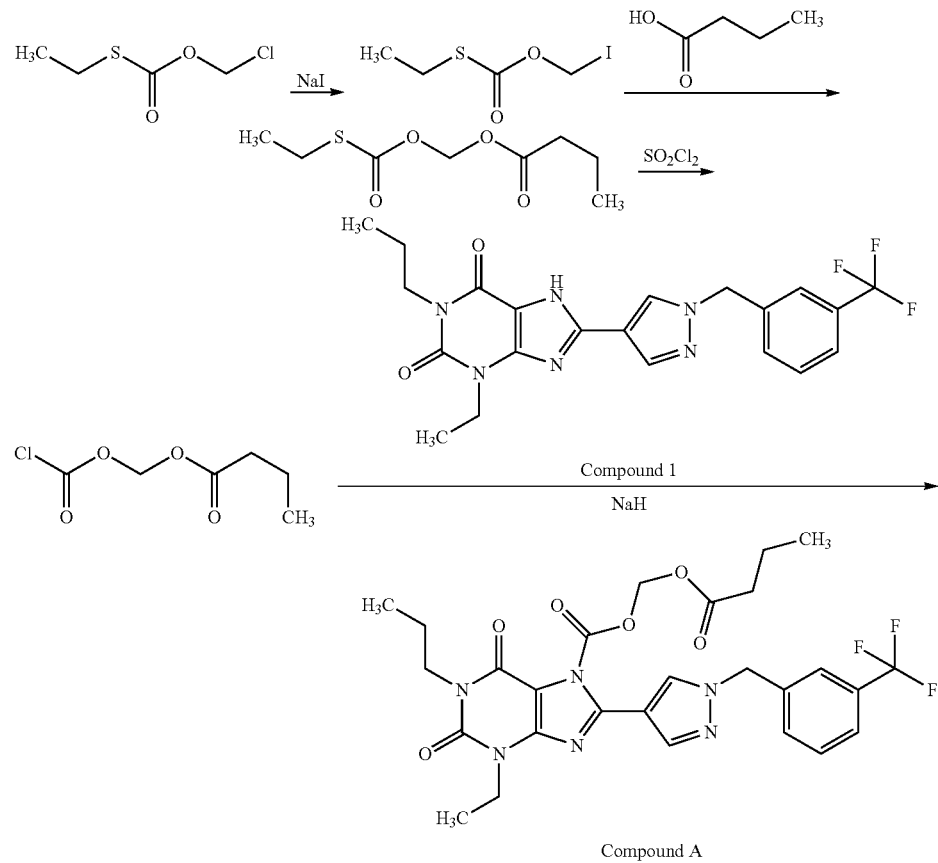

Step 1. O-(chloromethyl) S-ethyl carbonothioate, sodium iodide and 18-crown-6 are dissolved in toluene and heated to about 100° C. for about 5 hours to yield S-ethyl O-(iodomethyl) carbonothioate. Step 2. n-Butyric acid and tetrabutyl ammonium bisulfate, sodium carbonate are added to a solution of chloro(chloromethoxy)methane in methylene chloride/water at room temperature and stirred overnight to afford solid (((ethylthio)carbonyl)oxy)methyl butyrate. Step 3. Sulfuryl acid is added dropwise to a solution of (((ethylthio)carbonyl)oxy)methyl butyrate at about −30° C. The reaction mixture is allowed to warm to room temperature and stir for about 2 hours to yield a solution of ((chlorocarbonyl)oxy)methyl butyrate. Step 4. ((Chlorocarbonyl)oxy)methyl butyrate is added to a solution of compound 1 and sodium hydride in DMF at room temperature and allowed to stir for about 3 hours to yield Compound A.

Example 2—Synthesis of Exemplary Compound B

Compound B can be synthesized according the scheme below.

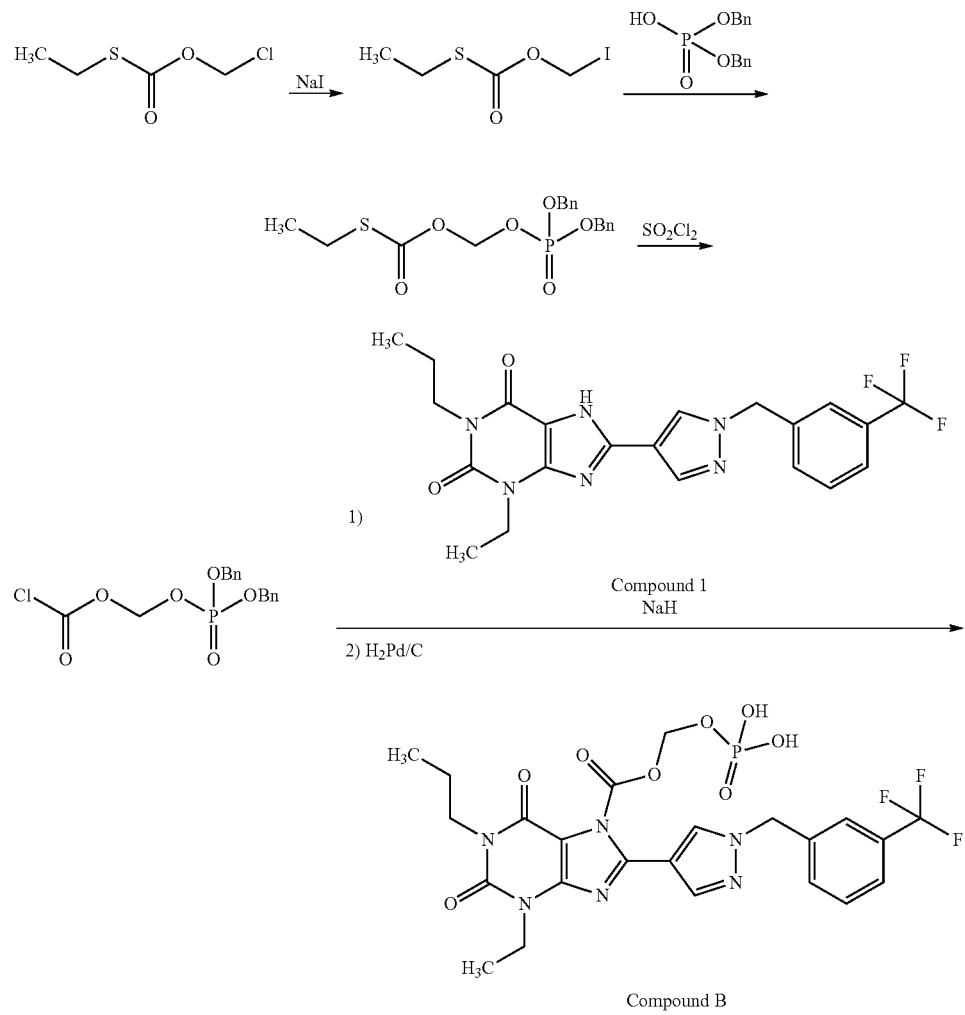

Step 1. O-(chloromethyl) S-ethyl carbonothioate, sodium iodide, and 18-crown-6 are dissolved in toluene and heated to 100° C. for 5 hours to form S-ethyl O-(iodomethyl) carbonothioate. Step 2. S-ethyl O-(iodomethyl) carbonothioate and dibenzyl hydrogen phosphate are reacted to form O-(((bis(benzyloxy)phosphoryl)oxy)methyl)S-ethyl carbonothioate. Step 3. Sulfuryl acid is added to a solution of O-(((bis(benzyloxy)phosphoryl)oxy)methyl)S-ethyl carbonothioate at −30° C. and allowed to warm to room temperature and stir for 2 hours to afford ((bis(benzyloxy) phosphoryl)oxy)methyl carbonochloridate. Step 4. To a DMF solution of ((bis(benzyloxy)phosphoryl)oxy)methyl carbonochloridate and compound 1 is added sodium hydride at room temperature. The solution is stirred for 3 hours. Pd/C in DMSO is added under $H_2$ at room temperature, and the reaction mixture is allowed to stir for 5 hours to afford Compound B.

Example 3—Synthesis of Exemplary Compound C

Compound C was synthesized according to the steps below.

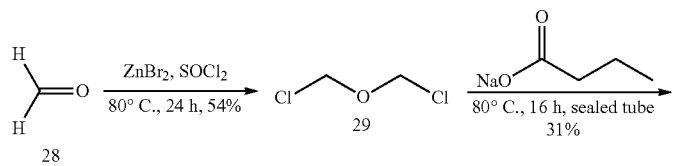

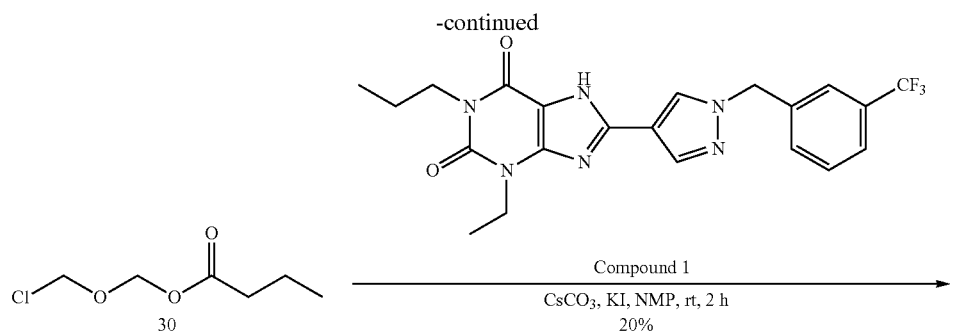

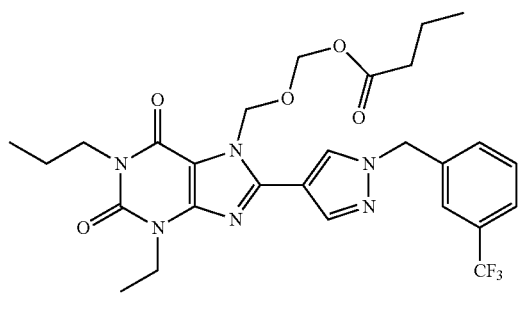

Compound C

To a solution of compound 28 (50.0 g, 1650 mmol, 1.0 eq) and thionyl chloride (63.0 mL, 849.9 mmol, 0.5151 eq) was added zinc bromide (4.58 g, 19.99 mmol, 0.01212 eq) under nitrogen atmosphere. The resulting mixture was stirred at 80° C. for 24 h. The progress of the reaction mixture was monitored by $^1$H NMR. After completion of the reaction, the resulting mixture was isolated by distillation (b.p. 103-104° C.) to afford a mixture of slightly yellow oil and white solid. The mixture was filtered to afford compound 29 (51.645 g, 54%) as a slightly yellow oil.

To a solution of compound 29 (10.0 g, 87.72 mmol, 3.0 eq) in hexane (50 mL) was added sodium butyrate (3.2 g, 29.24 mmol, 1.0 eq) in a sealed tube. The resulting mixture was stirred at 80° C. for 16 h. The progress of the reaction mixture was monitored by $^1$H NMR. After completion of the reaction, the resulting mixture was filtered and the filtrate was diluted with water and extracted with ethyl acetate. The organic layer was dried over anhydrous sodium sulfate and concentrated under reduced pressure to afford crude compound 30 (1.5 g, 31%).

$^1$H NMR (300 MHz, Chloroform-d) δ 5.51 (d, J=0.6 Hz, 2H), 5.42 (d, J=0.6 Hz, 2H), 2.36 (td, J=7.4, 0.6 Hz, 2H), 1.75-1.61 (m, 2H), 0.97 (td, J=7.4, 0.6 Hz, 3H).

A mixture of compound 30 (1.1 g, 6.63 mmol, 1.2 eq), compound 1 (2.5 g, 5.52 mmol, 1.0 eq), cesium carbonate (2.7 g, 8.28 mmol, 1.5 eq) and potassium iodide (1.1 g, 6.63 mmol, 1.2 eq) in 1-methyl-2-pyrrolidinone (30 mL) was stirred at room temperature for 2 h. The progress of the reaction mixture was monitored by TLC. After completion of the reaction, the mixture was quenched with water and extracted with ethyl acetate. The organic layer was washed with brine, dried over anhydrous sodium sulfate and concentrated under reduced pressure. The residue was purified by silica gel chromatography. The desired Compound C was obtained as white solid, 648 mg, in 20% yield.

LC-MS: 577.25 [M+1]$^+$. $^1$H NMR (300 MHz, CDCl$_3$): δ 8.12-8.04 (m, 2H), 7.59 (d, J=7.6 Hz, 1H), 7.55-7.40 (m, 3H), 5.91 (s, 2H), 5.53 (s, 2H), 5.42 (s, 2H), 4.18 (d, J=7.1 Hz, 2H), 3.97 (s, 2H), 2.16 (t, J=7.4 Hz, 2H), 1.68 (dd, J=15.1, 7.4 Hz, 2H), 1.53-1.46 (m, 2H), 1.34 (t, J=7.1 Hz, 3H), 0.95 (t, J=7.4 Hz, 3H), 0.84 (t, J=7.4 Hz, 3H).

Example 4—Synthesis of Exemplary Compound D

Compound D can be synthesized according to the scheme below.

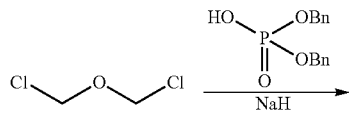

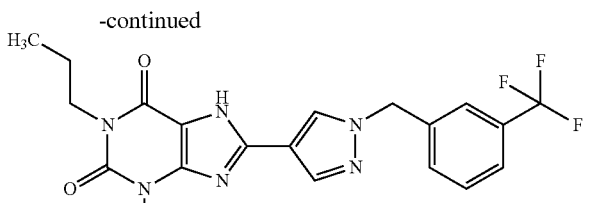

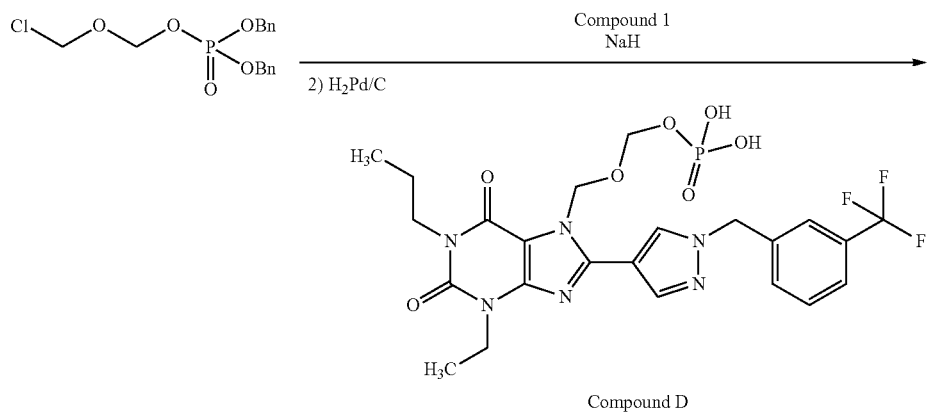

Compound D

Step 1. Chloro(chloromethoxy)methane and dibenzyl hydrogen phosphate is stirred in solution to afford dibenzyl ((chloromethoxy)methyl) phosphate. Step 2. Sodium hydride is added to a DMF solution of dibenzyl ((chloromethoxy)methyl) phosphate and compound 1 at room temperature. The reaction is stirred for about about 3 hours. Pd/C in DMSO is added and stirred under $H_2$ at room temperature for about 5 hours to afford Compound D.

Example 5—Synthesis of Exemplary Compound E

Compound E was synthesized according to the steps below.

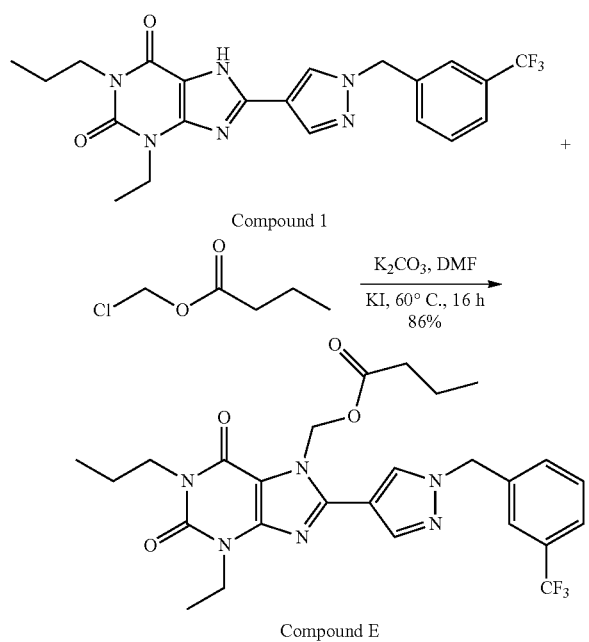

To a solution of compound 1 (400 mg, 0.897 mmol, 1.0 eq) in DMF (10 mL) was added $K_2CO_3$ (371 mg, 2.69 mmol, 3.0 eq) and KI (15 mg, 0.0897 mmol, 0.1 eq), followed by chloromethyl butyrate (366 mg, 2.69 mmol, 3.0 eq), and the mixture was stirred at 60° C. for 16 h. The solid was filtered off, and the filtrate was concentrated under reduced pressure. The residue was purified by silica gel chromatography using 30% ethyl acetate/hexane to afford Compound E (420 mg, 86%) as a white solid.

LCMS: [M+1]=547.45; $^1$H NMR (400 MHz, CDCl$_3$) δ 7.96 (d, J=2.1 Hz, 2H), 7.63-7.44 (m, 4H), 6.33 (s, 2H), 5.41 (s, 2H), 4.17 (d, J=7.1 Hz, 2H), 4.01-3.90 (m, 2H), 2.30 (t, J=7.4 Hz, 2H), 1.72-1.57 (m, 4H), 1.34 (t, J=7.1 Hz, 3H), 0.92 (dt, J=19.0, 7.5 Hz, 6H).

Example 6—Alternate Synthesis of Exemplary Compound E

Compound E was synthesized according to the steps below.

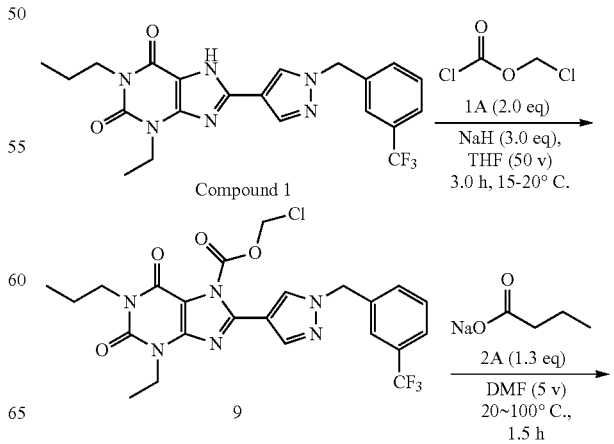

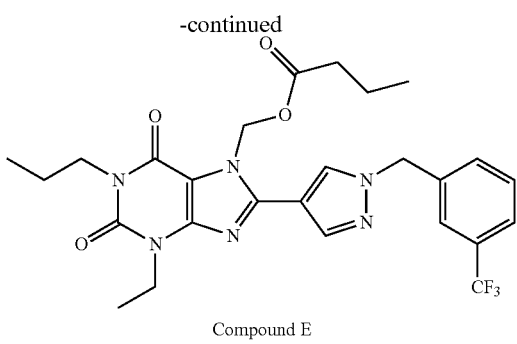

Compound E

To a solution of compound 1 (100 g, 224 mmol, 1.00 eq) in dry tetrahydrofuran (5.00 L) was added NaH (26.9 g, 672 mmol, 60% purity, 3.00 eq) at 15° C. The reaction was stirred for 1 h at 15-20° C. Compound 1A (57.8 g, 448 mmol, 2.00 eq) was added dropwise at 15-20° C. The reaction was stirred at 20° C. for 2 h. LCMS and TLC showed ~13% of Compound 1 remaining and ~80% of desired compound 9 was detected. Twelve reactions were combined for work up. The reaction mixture was filtered and the filtrate was concentrated under reduced pressure to give a residue (1.2 kg). The residue was taken in methyl tertbutyl ether (6.00 L) and the mixture was stirred at 15° C. for 3 h, then the mixture was filtered and the filtrate cake was dried to give compound 9 (950 g, 1.76 mol, 65.6% yield) as a white solid.

LCMS: (Product Rt=1.498 min, M+1=539.1) $^1$H NMR (400 MHz, CDCl$_3$) δ 8.23 (d, J=10.8 Hz, 2H), 7.62 (d, J=7.6 Hz, 1H), 7.46-7.56 (m, 3H), 5.96 (s, 2H), 5.44 (s, 2H), 4.21 (q, J=7.2 Hz, 2H), 3.95-3.99 (m, 2H), 1.64-1.74 (m, 2H), 1.37 (t, J=6.8 Hz, 3H), 0.97 (t, J=7.2 Hz, 3H).

To a mixture of compound 9 (50.0 g, 92.8 mmol, 1.00 eq) in DMF (250 mL) was added compound 2A (13.3 g, 121 mmol, 1.30 eq) in one portion at 20° C. under N2. The mixture was stirred at 100° C. (inner temperature) for 1.5 h. LCMS showed the reaction was complete. Nineteen reactions were combined for work up. The mixture was cooled to 20° C. and the suspension was filtered. The filtrate was purified using reversed-phase HPLC. The aqueous phase (~20.0 L) was concentrated in vacuo at 45° C. and it was extracted with ethyl acetate (5.00 L×3). The combined organic phase was washed with brine (3.00 L), dried with anhydrous sodium sulfate, filtered and concentrated in vacuo at 45° C. Isopropyl ether (4.00 L) was added to the residue and stirred for 6 h at 60° C. The mixture was cooled to 15° C. and the mixture was filtered. The filter cake was collected and dried at 45° C. to give Compound E (417 g, 697 mmol, 39.6% yield, 98.8% purity) as a white solid.

$^1$H NMR (400 MHz, CDCl$_3$) δ 7.98 (s, 2H), 7.62 (d, J=7.6 Hz, 1H) 7.47-7.56 (m, 3H), 6.35 (s, 2H), 5.44 (s, 2H), 4.18 (q, J=7.2 Hz, 2H), 3.96-4.00 (m, 2H), 2.33 (t, J=7.2 Hz, 2H), 1.62-1.70 (m, 4H), 1.35 (t, J=7.2 Hz, 3H), 0.96 (t, J=7.6 Hz, 3H), 0.91 (t, J=7.6 Hz, 3H).

Example 7—Synthesis of Exemplary Compound F

Compound F was synthesized according to the steps below.

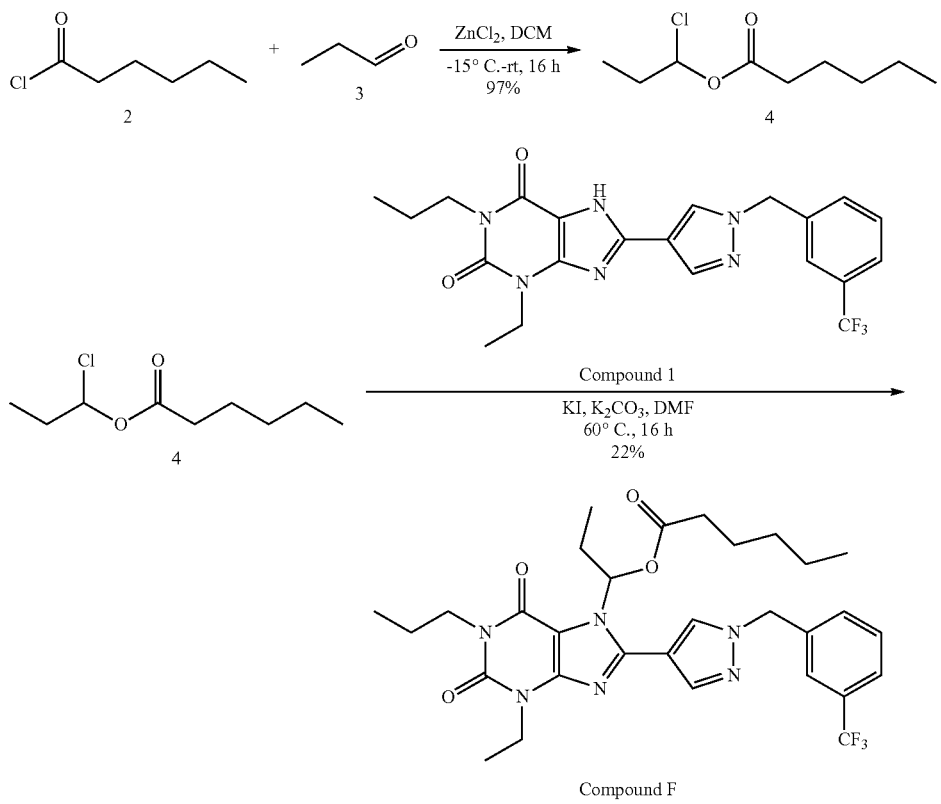

Compound F

To a solution of compound 2 (1 g, 7.46 mmol, 1.0 eq) in DCM (10 mL) was added ZnCl$_2$ (20 mg, 0.149 mmol, 0.02 eq). After being stirred at room temperature for 15 min, the mixture was cooled to −15° C. Then compound 3 (433 mg, 7.46 mmol, 1.0 eq) was added dropwise over 15 min. The mixture was allowed to warm to room temperature and stirred at room temperature for 16 h. The progress of the reaction mixture was monitored by TLC. The mixture was diluted with water and extracted with DCM. The organic layer was dried over anhydrous Na$_2$SO$_4$ and concentrated under reduced pressure to afford crude compound 4 (1.4 g, 97%).

To a solution of compound 1 (808 mg, 1.81 mmol, 1.0 eq) in DMF (10 mL) was added K$_2$CO$_3$ (750 mg, 5.44 mmol, 3.0 eq) and KI (30 mg, 0.181 mmol, 0.1 eq), followed by compound 4 (1.044 g, 5.44 mmol, 3.0 eq), and the mixture was stirred at 60° C. for 16 h. The progress of the reaction mixture was monitored by TLC. The solid was filtered off, and the filtrate was concentrated under reduced pressure. The residue was purified by silica gel chromatography using 30% ethyl acetate/hexane to afford Compound F (237 mg, 22%) as a white solid.

LCMS: [M+1]=603.45; $^1$H NMR (400 MHz, CDCl$_3$) δ 7.96 (d, J=2.1 Hz, 2H), 7.63-7.44 (m, 4H), 6.33 (s, 2H), 5.41 (s, 2H), 4.17 (d, J=7.1 Hz, 2H), 4.01-3.90 (m, 2H), 2.30 (t, J=7.4 Hz, 2H), 1.72-1.57 (m, 4H), 1.34 (t, J=7.1 Hz, 3H), 0.92 (dt, J=19.0, 7.5 Hz, 6H).

Example 8—Synthesis of Exemplary Compound G

Compound G was synthesized according to the steps below.

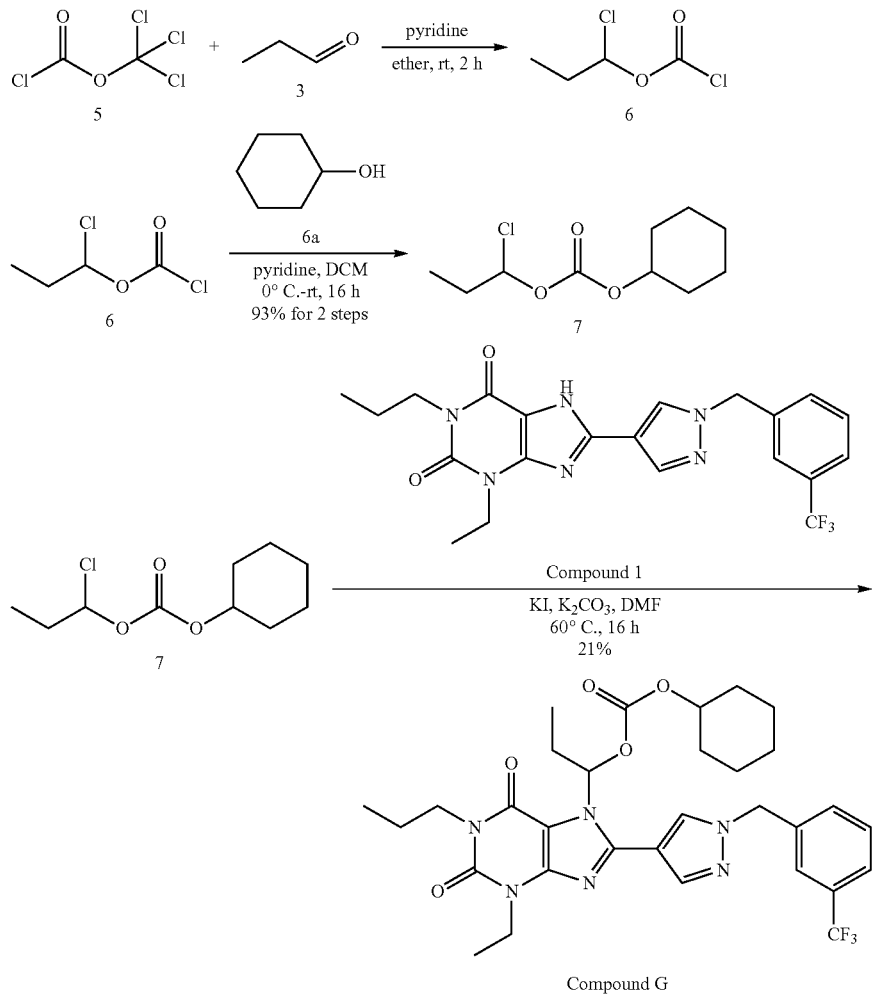

Compound G

A mixture of compound 5 (2 g, 10.20 mmol, 1.0 eq), compound 3 (947 mg, 16.33 mmol, 1.6 eq) and pyridine (81 mg, 1.02 mmol, 0.1 eq) in diethyl ether (20 mL) was stirred at room temperature for 2 h. The progress of the reaction mixture was monitored by TLC. The mixture was concentrated under reduced pressure to afford crude compound 6, which was used for next step directly.

To a mixture of crude compound 6 from previous step in DCM (20 mL) was successively added pyridine (1.6 g, 20.40 mmol, 2.0 eq) and a solution of compound 6a (1.07 g, 10.71 mmol, 1.05 eq) in DCM (10 mL). The mixture was allowed to warm to room temperature and stirred at room temperature for 16 h. The progress of the reaction mixture was monitored by TLC. The mixture was diluted with 1 N HCl and extracted with DCM. The organic layer was dried over anhydrous Na$_2$SO$_4$ and concentrated under reduced pressure to afford crude compound 7 (2.1 g, 93%).

To a solution of compound 1 (1.06 g, 2.38 mmol, 1.0 eq) in DMF (20 mL) was added KI (395 mg, 0.238 mmol, 0.1 eq). After being stirred for 15 min, K$_2$CO$_3$ (983 mg, 7.13 mmol, 3.0 eq) and compound 7 (2.1 g, 9.50 mmol, 4.0 eq) was added. The mixture was stirred at 60° C. for 16 h. The progress of the reaction mixture was monitored by TLC. The mixture was diluted with water and extracted with DCM. The organic layer was dried over anhydrous Na$_2$SO$_4$ and concentrated under reduced pressure. The residue was purified by silica gel chromatography to afford Compound G (316 mg, 21%) as a white solid.

LCMS: [M+1]=631.55; $^1$H NMR (400 MHz, CDCl$_3$) δ8.11 (s, 2H), 7.67-7.40 (m, 4H), 5.42 (s, 2H), 5.29 (d, J=6.6 Hz, 1H), 4.56 (s, 1H), 4.16 (d, J=6.9 Hz, 2H), 3.97 (dd, J=14.5, 7.0 Hz, 2H), 2.14 (s, 2H), 1.88 (s, 1H), 1.68 (dd, J=14.7, 7.3 Hz, 5H), 1.49 (s, 1H), 1.41 (d, J=9.6 Hz, 1H), 1.33 (t, J=6.9 Hz, 4H), 1.25-1.14 (m, 3H), 0.94 (t, J=7.3 Hz, 3H), 0.83 (t, J=7.2 Hz, 3H).

Example 9—Synthesis of Exemplary Compound H

Compound H was synthesized according to the steps below.

To a mixture of crude compound 6 (1.5 g, 9.62 mmol, 1.0 eq) from previous step in DCM (20 mL) was successively added pyridine (1.52 g, 19.23 mmol, 2.0 eq) and a solution of compound 8a (606 mg, 10.10 mmol, 1.05 eq) in DCM (5 mL). The mixture was allowed to warm to room temperature and stirred at room temperature for 16 h. The progress of the reaction mixture was monitored by TLC. The mixture was diluted with 1 N HCl and extracted with DCM. The organic layer was dried over anhydrous Na$_2$SO$_4$ and concentrated under reduced pressure to afford crude compound 8 (2.1 g, 100%).

To a solution of the Compound 1 (1.36 g, 2.92 mmol, 1.0 eq) in DMF (20 mL) was added KI (48 mg, 0.292 mmol, 0.1 eq). After being stirred for 15 min, K$_2$CO$_3$ (1.2 g, 8.76 mmol, 3.0 eq) and compound 8 (2.1 g, 11.67 mmol, 4.0 eq) was added. The mixture was stirred at 60° C. for 16 h. The progress of the reaction mixture was monitored by TLC. The mixture was diluted with water and extracted with DCM. The organic layer was dried over anhydrous Na$_2$SO$_4$ and concentrated under reduced pressure. The residue was purified by silica gel chromatography to afford Compound H (462 mg, 25%) as a colorless oil.

LCMS: [M+1]=592.50; $^1$H NMR (400 MHz, CDCl$_3$) δ8.10 (s, 2H), 7.58-7.46 (m, 4H), 5.42 (s, 2H), 4.17-3.92 (m, 7H), 2.21-2.13 (m, 2H), 1.69-1.58 (m, 4H), 1.35 (m, 3H), 0.87-0.82 (m, 9H).

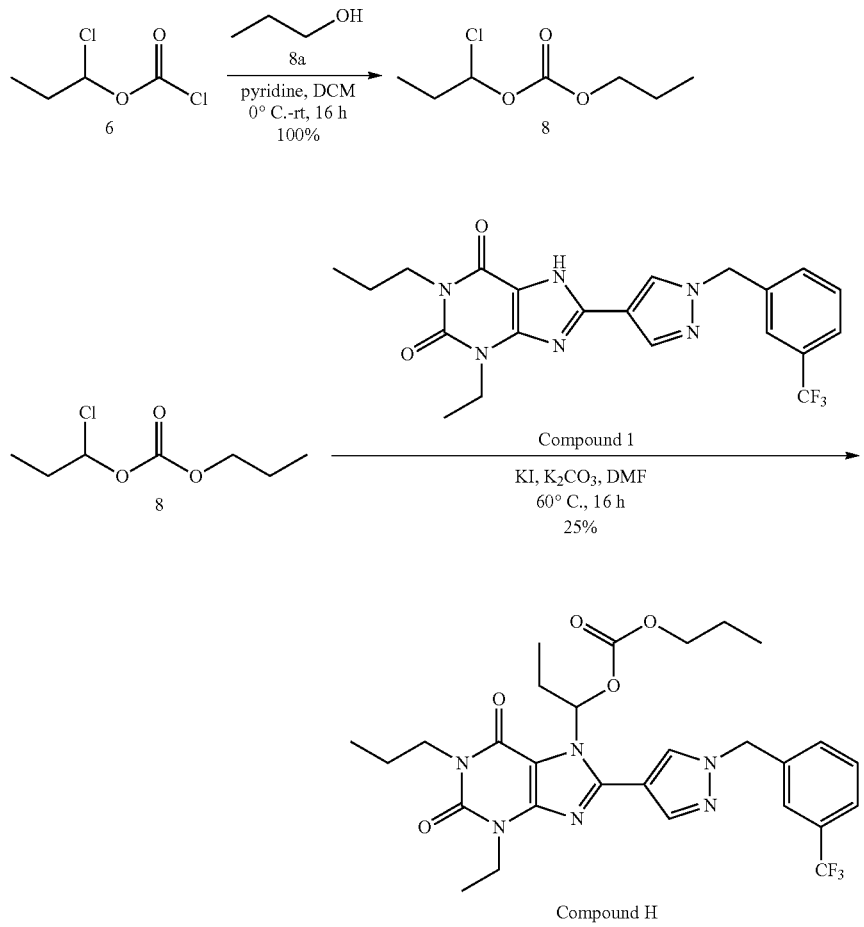

Compound H

Example 10—Synthesis of Exemplary Compound I

Compound I was synthesized according to the steps below.

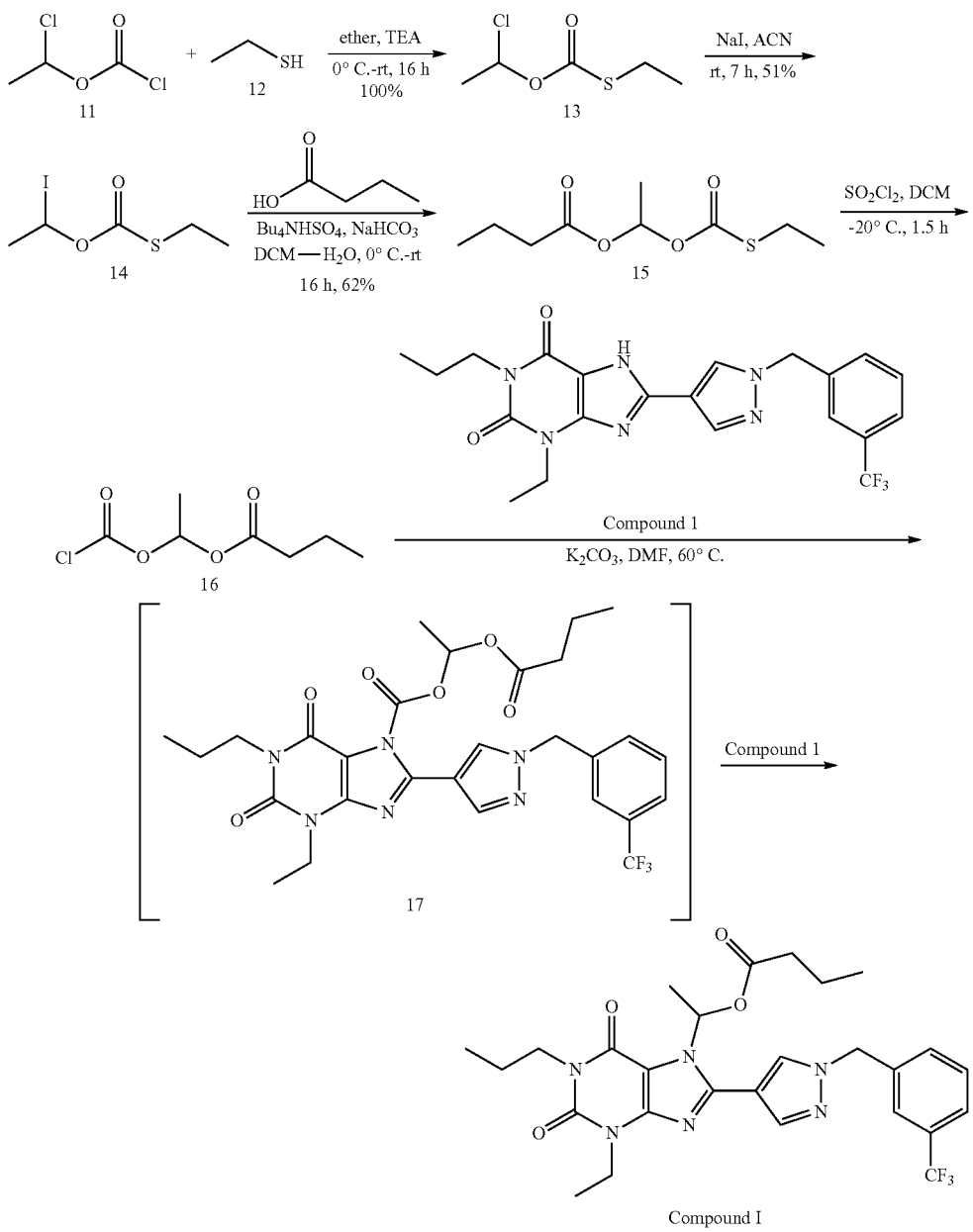

A solution of compound 11 (2.17 g, 34.97 mmol, 1.0 eq) and triethylamine (3.54 g, 34.97 mmol, 1.0 eq) in ether (10 mL) was cooled to 0° C. and a solution of compound 12 (5.0 g, 34.97 mmol, 1.0 eq) in ether (60 mL) was added dropwise. The mixture was stirred at 0° C. for 30 min and warmed to room temperature and stirred for 16 h. The progress of the reaction mixture was monitored by $^1$H NMR. After completion of the reaction, the mixture was filtered, and the filtrate was concentrated under reduced pressure to afford crude compound 13 (6.2 g, 100%) as a green oil.

To a solution of compound 13 (5.0 g, 29.76 mmol, 1.0 eq) in acetonitrile (50 mL) was sodium iodide (22.3 g, 148.8 mmol, 5.0 eq). The mixture was stirred at room temperature for 7 h. The progress of the reaction mixture was monitored by $^1$H NMR. After completion of the reaction, the mixture was concentrated under reduced pressure to remove the acetonitrile solvent. The residue was diluted with ethyl acetate and extracted with water. The organic layer was dried over anhydrous sodium sulfate and concentrated under reduced pressure to afford crude compound 14 (4.0 g, 51%).

A solution of butyric acid (21.0 g, 238.5 mmol, 2.0 eq) in dichloromethane (200 mL/100 mL) was cooled to 0° C. and a solution of tetrabutylammonium hydrogen sulfate (81.0 g, 238.5 mmol, 2.0 eq) and sodium bicarbonate (40.1 g, 476.9 mmol, 4.0 eq) was added. The resulting solution was warmed to room temperature and stirred at room temperature for 1 h. A solution of compound 14 (32.0 g, 119.2 mmol, 1.0 eq) was then added at this temperature and the mixture was stirred for 16 h. The progress of the reaction mixture was monitored by TLC. After completion of the reaction, the mixture was diluted with water and extracted with ethyl acetate. The organic layer was dried over anhydrous sodium sulfate and concentrated under reduced pressure. The residue was purified by chromatography over silica gel (0-1% ethyl acetate in petroleum ether). The desired compound 15 was obtained as yellow oil, 17.0 g, in 62% yield.

LCMS: 221.25 [M+1]. $^1$H NMR (400 MHz, CDCl$_3$) δ 6.93 (q, J=5.5 Hz, 1H), 2.89-2.80 (m, 2H), 2.29 (td, J=7.3, 3.0 Hz, 2H), 1.64 (dd, J=14.8, 7.4 Hz, 2H), 1.48 (d, J=5.5 Hz, 3H), 1.34-1.27 (m, 3H), 0.93 (t, J=7.4 Hz, 3H).

To a stirred solution of compound 15 (0.5 g, 2.27 mmol) in DCM (5 mL) sulfuryl chloride (0.60 g, 4.52 mmol) was added at −25° C. and reaction was stirred at same temperature for 1.5 h. The solvent was removed to afford compound 16 (0.52 g). Compound 16 was pure enough for further use.

To a stirred solution of compound 1 (0.5 g, 1.12 mmol) in DMF (5 mL), K$_2$CO$_3$ (0.31 g, 2.24 mmol) was added followed by addition of compound 16 (0.65 g, 3.36 mmol) at room temperature and reaction was heated at 60° C. for overnight. Reaction was monitored using LCMS. LCMS showed nearly ~5% conversion. Reaction was diluted with ethyl acetate and water was added. Organic layer was separated and aqueous was washed with ethyl acetate (15× 2). Combined organic layer was dried over sodium sulfate, concentrated. To the solid residue 1:1 mixture of ethyl acetate and hexane was added and solid compound 1 was filtered. Filtrate was concentrated and purified using prep-HPLC by eluting 10-100% ACN (0.1% TFA) and water (0.1% TFA) to afford Compound I (35 mg, 5%).

LC-MS: 561.3 (M+1). $^1$H NMR (300 MHz, Chloroform-d) δ 8.08 (s, 1H), 8.06 (s, 1H), 7.64-7.49 (m, 4H), 7.34 (q, J=6.4 Hz, 1H), 5.44 (s, 2H), 4.17 (q, J=7.1 Hz, 2H), 4.02-3.97 (m, 2H), 2.33-2.22 (m, 2H), 1.87 (d, J=6.4 Hz, 3H), 1.73-1.44 (m, 2H), 1.62-1.55 (m, 2H), 1.34 (t, J=7.0 Hz, 3H), 0.96 (t, J=7.4 Hz, 3H), 0.85 (t, J=7.4 Hz, 3H).

Example 11—Synthesis of Exemplary Compound J

Compound J was synthesized according to the steps below, in a similar way as Example 9.

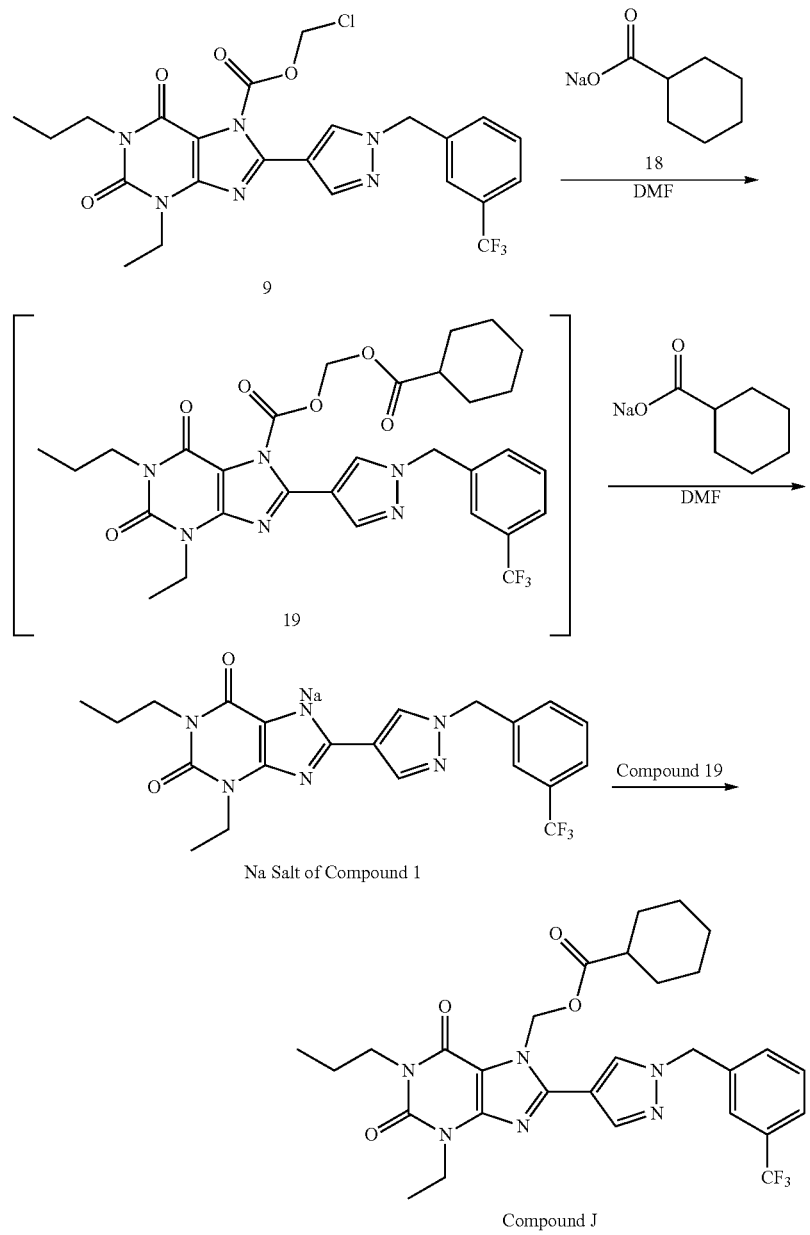

Compound J

A mixture of compound 9 (0.3 g, 0.55 mmol) and 18 (0.08 g, 0.71 mmol) was heated at 80° C. in DMF for 1 h. LCMS showed complete conversion to Compound J. The reaction is believed to form intermediate compound 19, which further reacts with compound 18 to form the sodium salt of compound 1. The sodium salt of compound 1 further reacts with intermediate compound 19 to form Compound J. The solvent was removed under vacuum and the residue was purified using prep HPLC by eluting 10-100% ACN (0.1% TFA) and water (0.1% TFA) to afford Compound J (140 mg, 43%).

LC-MS: 587.3 (M+1). $^1$H NMR (300 MHz, Chloroform-d) δ 7.97 (s, 1H), 7.96 (s, 1H), 7.72-7.42 (m, 4H), 6.33 (s, 2H), 5.43 (s, 2H), 4.18 (q, J=7.0 Hz, 2H), 4.03-3.90 (m, 2H), 2.39-2.27 (m, 1H), 1.85-1.69 (m, 8H), 1.36 (t, J=7.0 Hz, 3H), 1.30-1.14 (m, 4H), 0.96 (t, J=7.0 Hz, 3H).

Example 12—Synthesis of Exemplary Compound K

Compound K was synthesized according to the steps below, in a similar way as Example 10.

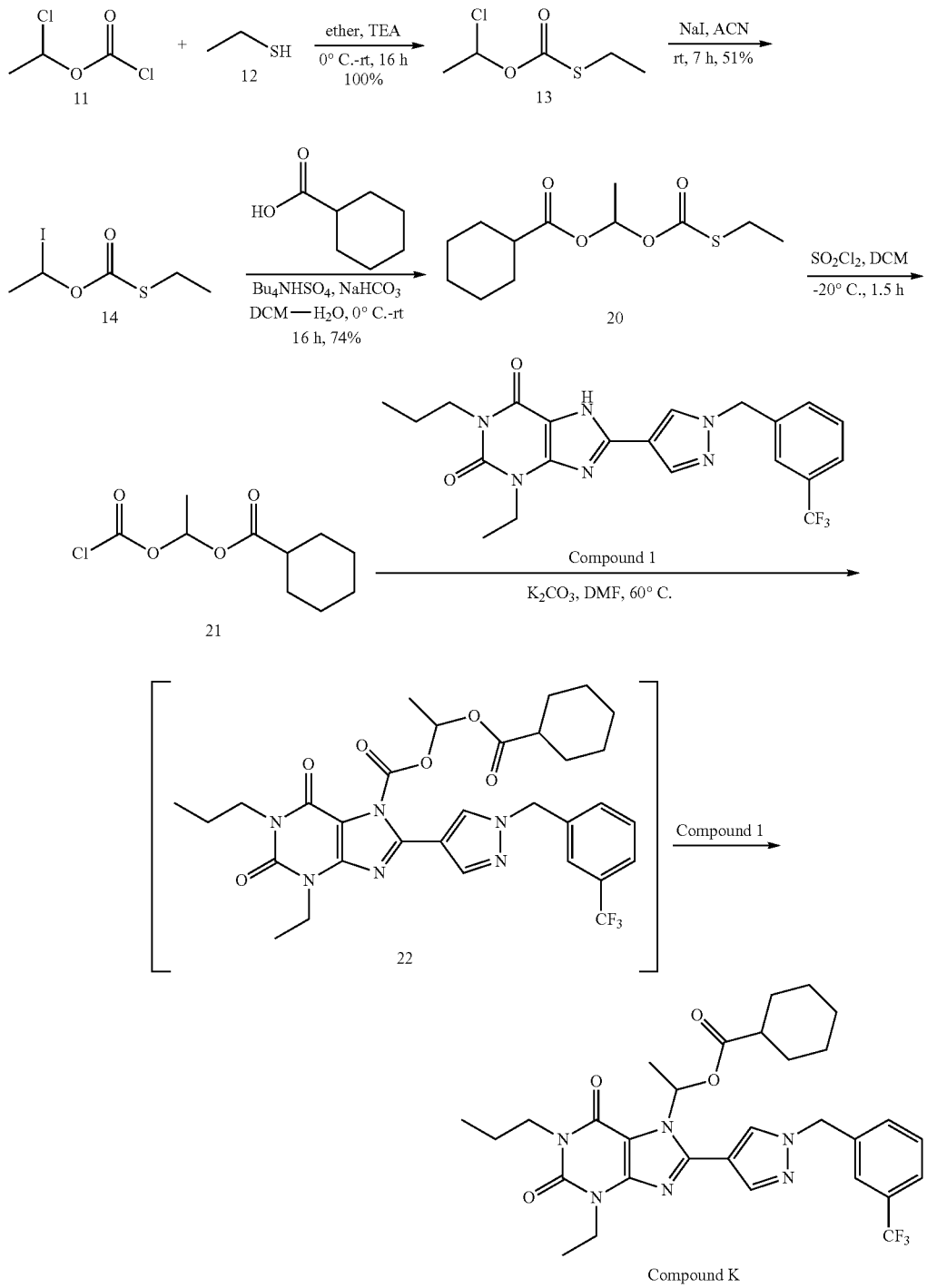

A solution of cyclohexyl carboxylic acid (2.6 g, 29.85 mmol, 2.0 eq) in dichloromethane (30 mL/15 mL) was cooled to 0° C. and a solution of tetrabutylammonium hydrogen sulfate (10.1 g, 29.85 mmol, 2.0 eq) and sodium bicarbonate (5.0 g, 59.70 mmol, 4.0 eq) was added. The resulting solution was warmed to room temperature and stirred for 1 h. A solution of compound 14 (4.0 g, 14.93 mmol, 1.0 eq) was then added and the mixture was stirred for 16 h. The progress of the reaction mixture was monitored by TLC. After completion of the reaction, the mixture was diluted with water and extracted with ethyl acetate. The organic layer was dried over anhydrous sodium sulfate and concentrated under reduced pressure. The residue was purified by chromatography over silica gel (0-1% ethyl acetate in petroleum ether). The desired compound 20 was obtained as a colorless oil, 2.98 g, in 74% yield.

LC-MS: 283.05 [M+23]±. $^1$H NMR (300 MHz, CDCl$_3$): δ 6.91 (d, J=5.5 Hz, 1H), 2.85 (qd, J=7.4, 3.5 Hz, 2H), 2.33-2.24 (m, 1H), 1.88 (d, J=10.9 Hz, 2H), 1.76-1.69 (m, 2H), 1.47 (d, J=5.5 Hz, 3H), 1.43 (d, J=12.5 Hz, 2H), 1.29 (dd, J=11.5, 4.2 Hz, 4H), 1.25-1.20 (m, 3H).

To a stirred solution of compound 20 (0.5 g, 2.27 mmol) in DCM (5 mL) sulfuryl chloride (0.60 g, 4.52 mmol) was added at −25° C. and reaction was stirred at same temperature for 1.5 h. The solvent was removed to afford compound 21 (0.52 g). Compound 21 was pure enough for further use.

To a stirred solution of compound 1 (0.5 g, 1.12 mmol) in DMF (5 mL), K$_2$CO$_3$ (0.31 g, 2.24 mmol) was added followed by addition of compound 21 (0.65 g, 3.36 mmol) at room temperature and the reaction was stirred overnight at 60° C. The reaction was monitored using LCMS. LCMS showed nearly ~10-15% conversion. The reaction was diluted with ethyl acetate and water was added. The organic layer was separated and the aqueous layer was washed with ethyl acetate (15 mL×2). The organic layer was combined with the ethyl acetate washings and dried over sodium sulfate before drying the solution under vacuum. To the solid residue 1:1 mixture of ethyl acetate and hexane was added and solid compound 1 was removed via filtration. The filtrate was concentrated and purified using prep HPLC by eluting 10-100% ACN (0.1% TFA) and water (0.1% TFA) to afford Compound K (72 mg, 10%).

LC-MS: 601.3 (M+1). $^1$H NMR (300 MHz, Chloroform-d) δ 8.10 (s, 1H), 8.06 (s, 1H), 7.67-7.43 (m, 4H), 7.24 (q, J=6.4 Hz, 1H), 5.45 (s, 2H), 4.17 (q, J=7.0 Hz, 2H), 4.13-3.97 (m, 2H), 2.36-2.24 (m, 1H), 1.89 (d, J=6.4 Hz, 3H), 1.83-1.62 (m, 8H), 1.34 (t, J=7.0 Hz, 3H), 1.27-1.09 (m, 4H), 0.96 (t, J=7.4 Hz, 3H).

Example 13—Synthesis of Exemplary Compound L

Compound L was synthesized according to the steps below.

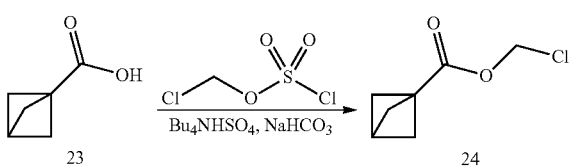

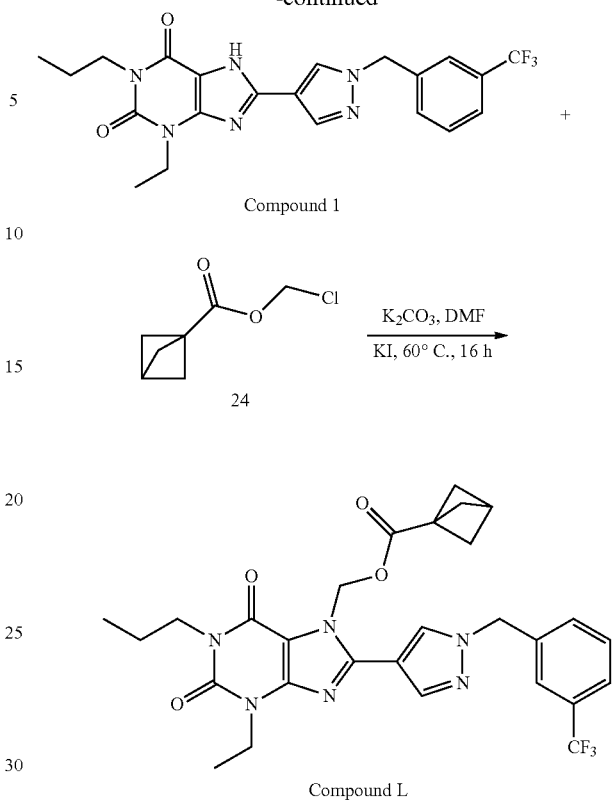

To a mixture of acid 23 (150 mg, 1.34 mmol), tetrabutylammonium hydrogen sulfate (45.4 mg, 0.1 eq) and NaHCO$_3$ (566 mg, 5 eq) in DCM:H$_2$O (1:1, 6.6 mL) was added a solution of chloromethyl chlorosulfate (222 mg, 1 eq) in DCM (1.1 mL) at 0° C. The reaction mixture was warmed up to room temperature and stirred overnight. The reaction mixture was diluted with DCM, washed with brine, dried over Na$_2$SO$_4$, filtrated and concentrated. The crude mixture was dissolved in DCM and passed through a small amount of silica gel (pipette used), eluting with DCM. After concentrating, 125 mg of compound 24 obtained as a colorless oil.

Compound 24 (117 mg, 1.5 eq) was combined with compound 1 (215 mg, 0.49 mmol), K$_2$CO$_3$ (206 mg, 3 eq), and anhydrous DMF (8.1 mL). The reaction mixture was heated to 60° C. for 14 hrs, filtered through celite, and concentrated. Purification via FCC (SiO2: 30-50% EtOAc/hexanes) provided 134 mg of desire product (about 93% purity). The solid was purified via Prep-HPLC (H$_2$O/CH$_3$CN in 0.1% formic acid, 10-100, 20 mL/min, 30 min). After lyophilizing, 92 mg of Compound L was obtained as a white solid (96% purity).

LCMS: [M+H]$^+$=571. $^1$H NMR (300 MHz, CDCl$_3$): δ 7.97 (s, 2H), 7.62 (d, J=7.8 Hz, 1H), 7.46-7.56 (m, 3H), 6.32 (s, 2H), 5.43 (s, 2H), 4.18 (q, J=6.9 Hz, 2H), 3.97 (t, J=7.5 Hz, 2H), 2.40 (s, 1H), 2.04 (s, 6H), 1.62-1.75 (m, 2H), 1.35 (t, J=6.9 Hz, 3H), 0.95 (t, J=7.5 Hz, 3H)

Example 14—Synthesis of Exemplary Compound M

Compound M was synthesized according to the steps below.

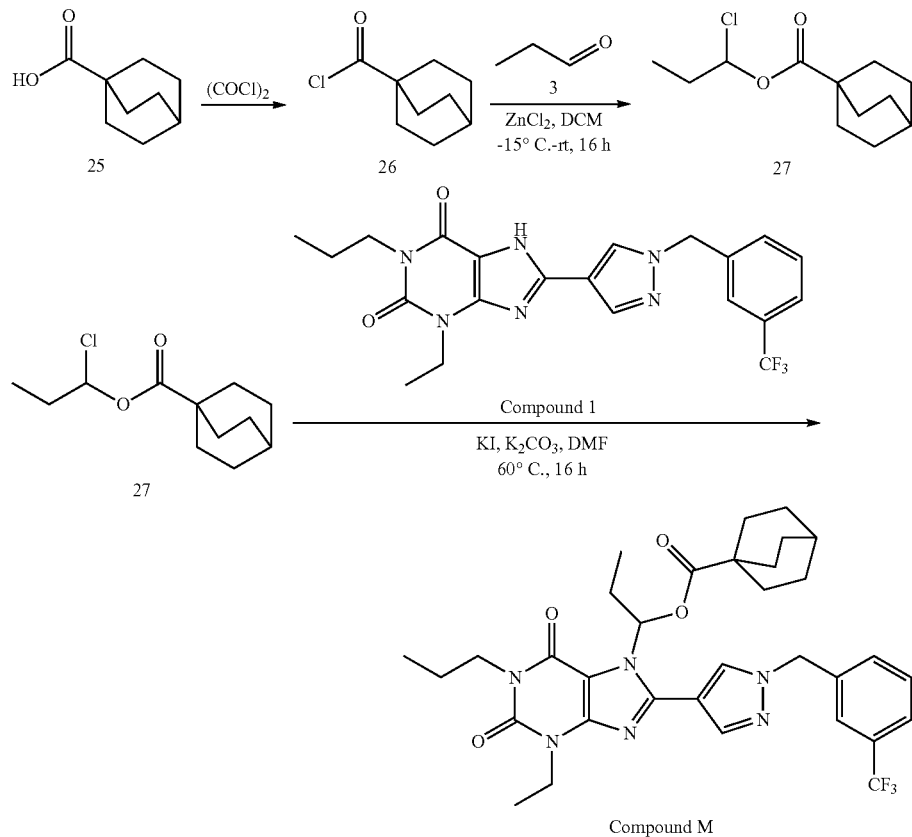

Compound M

To a solution of compound 25 (548 mg, 3.56 mmol) in anhydrous Et$_2$O (17 mL) was added oxalyl chloride (0.61 mL, 2 eq) at room temperature, followed by 3 drops of DMF. The reaction mixture was stirred at room temperature for 4 hrs and concentrated. The crude compound 26 was dissolved in anhydrous DCM (11 mL), anhydrous ZnCl$_2$ (10.3 mg, 0.02 eq) was added, cooled to −15° C., and propanal (0.26 mL, 1 eq) was added dropwise. The mixture was warmed up to room temperature, stirred overnight, and concentrated. The crude mixture was dissolved in DCM and passed through a small amount of silica gel (pipette used), eluting with DCM. After concentrating, 714 mg of compound 27 obtained as a white solid.

Compound 27 (704 mg, 2 eq) was combined with compound 1 (680 mg, 1.52 mmol), K$_2$CO$_3$ (640 mg, 3 eq), NaI (46.6 mg, 0.15 eq), and anhydrous DMF (25 mL). The reaction mixture was heated to 80° C. for 14 hrs, filtered through celite, and concentrated. HPLC showed about 30% conversion. Purification via FCC (SiO$_2$: 20-30% EtOAc/hexanes) provided 210 mg of desire product Compound M (99% purity).

LCMS: [M+H]$^+$=641. $^1$H NMR (300 MHz, CDCl$_3$): δ 8.13 (s, 1H), 8.06 (s, 1H), 7.60 (d, J=6.9 Hz, 1H), 7.45-7.54 (m, 3H), 6.94 (bs, 1H), 5.43 (s, 2H), 4.16 (q, J=6.9 Hz, 2H), 3.99 (t, J=7.2 Hz, 2H), 2.42 (m, 1H), 2.19 (m, 2H), 1.62-1.75 (m, 6H), 1.56-1.62 (m, 2H), 1.48-1.55 (m, 6H), 1.33 (t, J=7.1 Hz, 3H), 0.95 (t, J=7.2 Hz, 3H), 0.87 (t, J=7.5 Hz, 3H)

Example 15—Synthesis of Exemplary Compound N

Compound N was synthesized according to the steps below.

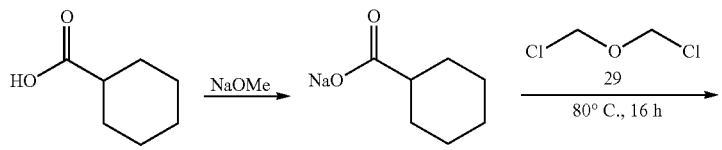

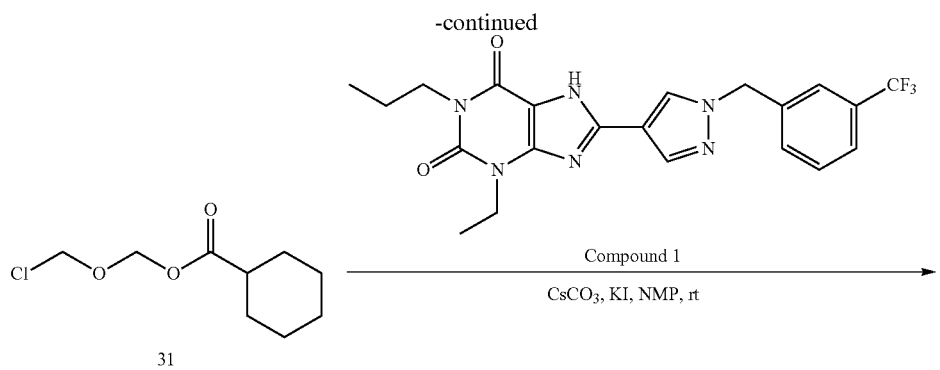

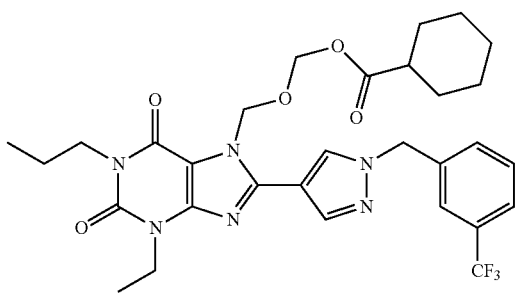

Compound N

Cyclohexane carboxylic acid (1.31 g, 10.23 mmol) was dissolved in MeOH (5 mL) and to which was added NaOMe (2.34 mg, 10.23 mmol, 25% wt) dropwise at room temperature. The reaction was stirred for 1 h. The solvent was removed in vacuo and the solid was dried under vacuum to afford sodium cyclohexanecarboxylate (1.46 g, 95% yield) as a white solid. Compound 29 (0.5 M in hexane, 3.1 eq) and sodium cyclohexanecarboxylate (1.0 eq) was charged in sealed reaction tube and heated 80° C. for 16 h. The reaction was cooled and dried under vacuum. The residue was purified with flash chromatography column in 0-20% EtOAc/Hex. 28.5 mg (24% yield) of compound 31 was obtained as a colorless oil.

$^1$H NMR (300 MHz, Chloroform-d) δ 5.50 (d, J=1.2 Hz, 2H), 5.41 (d, J=1.2 Hz, 2H), 2.36 (dddd, J=11.4, 10.2, 4.4, 3.2 Hz, 1H), 1.99-1.87 (m, 2H), 1.82-1.71 (m, 2H), 1.70-1.38 (m, 4H), 1.38-1.30 (m, 1H), 1.30-1.20 (m, 2H).

Compound 31 (1.2-2.5 eq) and compound 1 (1.0 eq) was dissolved in anhydrous NMP (0.4 M), to which was added Cs$_2$CO$_3$ (1.5 eq), KI (1.2 eq) at room temperature under N2 atmosphere. The reaction was stirred for 1 h and monitored by LCMS. Then the reaction was diluted with EtOAc and the organic phase was washed with water (3×). The organic phase was dried over anhydrous Na$_2$SO$_4$, filtered and concentrated. The residue was purified with flash chromatography column in 0-80% EtOAc/Hex to afford Compound N as a colorless oil.

LCMS (M+1)±: 617; $^1$H NMR (300 MHz, Chloroform-d) δ 8.10 (d, J=3.7 Hz, 2H), 7.64-7.41 (m, 4H), 5.92 (s, 2H), 5.56 (s, 2H), 5.43 (s, 2H), 4.19 (q, J=7.0 Hz, 2H), 4.07-3.89 (m, 2H), 2.12 (td, J=7.0, 3.2 Hz, 1H), 1.85-1.47 (m, 8H), 1.35 (t, J=7.0 Hz, 3H), 1.20 (ddd, J=18.4, 10.6, 4.7 Hz, 4H), 0.96 (t, J=7.4 Hz, 3H).

Example 16—Synthesis of Exemplary Compound O

Compound O was synthesized according to the steps below.

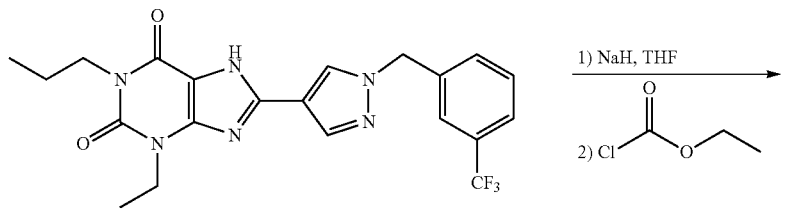

Compound 1

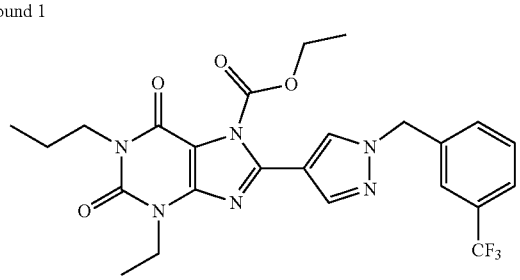

Compound O

To a solution of compound 1 (400 mg, 0.89 mmol, 1.0 eq) in tetrahydrofuran (5 mL) was added sodium hydride (60%, 286 mg, 7.14 mmol, 8.0 eq) at 0° C. The mixture was warmed to room temperature and stirred for 1 h. Then the mixture was cooled to 0° C. and ethyl carbonochloridate (386 mg, 3.57 mmol, 4.0 eq) was added dropwise. The resulting mixture was stirred from 0° C. to room temperature overnight. The progress of the reaction mixture was monitored by TLC. After completion, the mixture was quenched with ice-cold water and extracted with ethyl acetate. The organic layer was dried over anhydrous sodium sulfate and concentrated under reduced pressure. The residue was purified by chromatography over silica gel (0-25% ethyl acetate in petroleum ether). The desired Compound O was obtained as a white solid, 354 mg, in 76% yield.

LC-MS: 519.25 [M+1]$^+$. $^1$H NMR (400 MHz, CDCl$_3$): δ 8.19 (s, 1H), 8.14 (s, 1H), 7.62-7.57 (m, 1H), 7.54-7.42 (m, 3H), 5.39 (s, 2H), 4.49 (d, J=7.1 Hz, 2H), 4.18 (d, J=7.1 Hz, 2H), 4.00-3.92 (m, 2H), 1.72-1.63 (m, 2H), 1.40 (t, J=7.2 Hz, 3H), 1.35 (d, J=7.1 Hz, 3H), 0.94 (s, 3H).

Example 17—Synthesis of Exemplary Compound P

Compound P was synthesized according to the steps below.

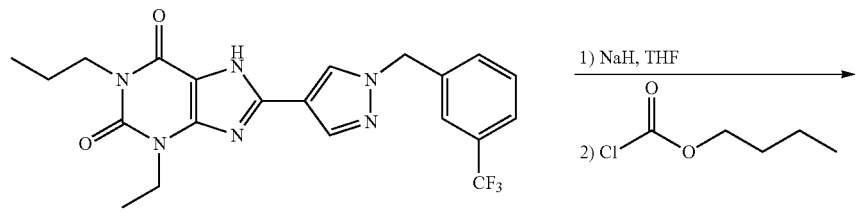

Compound 1

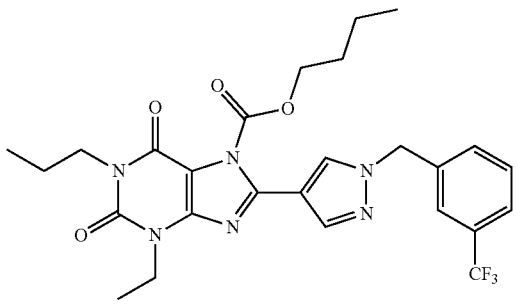

Compound P

To a solution of compound 1 (500 mg, 1.12 mmol, 1.0 eq) in tetrahydrofuran (5 mL) was added 60% sodium hydride (357 mg, 8.93 mmol, 8.0 eq) at 0° C. The mixture was warmed to room temperature and stirred for 1 h. Then the mixture was cooled to 0° C. and butyl carbonochloridate (610 mg, 4.47 mmol, 4.0 eq) was added dropwise. The resulting mixture was stirred from 0° C. to room temperature overnight. The progress of the reaction mixture was monitored by TLC. After completion, the mixture was quenched with ice-cold water and extracted with ethyl acetate. The organic layer was dried over anhydrous sodium sulfate and concentrated under reduced pressure. The residue was purified by chromatography over silica gel (0-25% ethyl acetate in petroleum ether). The desired Compound P was obtained as a white solid, 340 mg, in 55% yield.

LC-MS: 547.30 [M+1]$^+$. $^1$H NMR (400 MHz, CDCl$_3$): δ 8.19 (s, 1H), 8.14 (s, 1H), 7.58 (s, 1H), 7.52 (s, 1H), 7.49 (s, 1H), 7.45 (s, 1H), 5.39 (s, 2H), 4.42 (d, J=6.9 Hz, 2H), 4.18 (d, J=7.0 Hz, 2H), 3.98-3.93 (m, 2H), 1.78-1.71 (m, 5H), 1.70-1.61 (m, 1H), 1.43-1.37 (m, 1H), 1.33 (d, J=7.1 Hz, 1H), 0.93 (dt, J=11.2, 7.4 Hz, 7H).

Example 18—Synthesis of Exemplary Compound Q

Compound Q was synthesized according to the steps below.

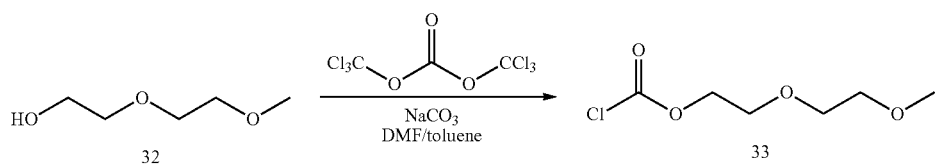

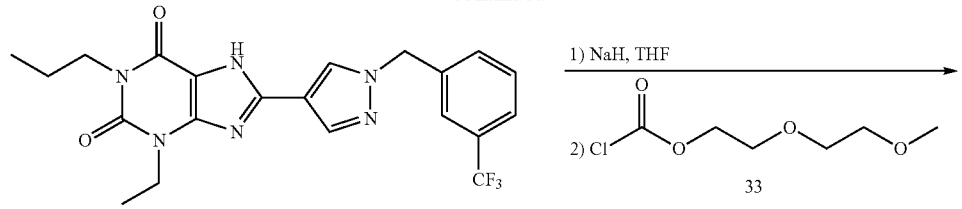

Compound 1

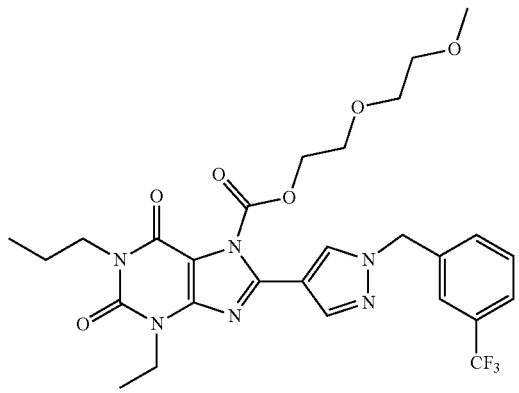

Compound Q

A mixture of bis(trichloromethyl) carbonate (5.0 g, 16.65 mmol, 0.5 eq), sodium carbonate (3.5 g, 33.29 mmol, 1.0 eq) and dimethylformamide (0.1 mL) in toluene (50 mL) was cooled to 0° C. and stirred for 0.5 h under nitrogen atmosphere. Then a solution of compound 32 (4.0 g, 33.29 mmol, 1.0 eq) was added dropwise. The mixture was stirred for an additional 4 hours at 0° C., monitored by $^1$H NMR. After completion, the mixture was filtered, and the filtrate was concentrated under reduced pressure to afford crude compound 33 (4.0 g, 66%).

To a solution of compound 1 (615 mg, 1.37 mmol, 1.0 eq) in tetrahydrofuran (5 mL) was added 60% sodium hydride (440 mg, 10.99 mmol, 8.0 eq) at 0° C. The mixture was warmed to room temperature and stirred for 1 h. Then the mixture was cooled to 0° C. and compound 33 (1.0 g, 5.49 mmol, 4.0 eq) was added dropwise. The resulting mixture was stirred from 0° C. to room temperature overnight. The progress of the reaction mixture was monitored by TLC. After completion, the mixture was quenched with ice-cold water and extracted with ethyl acetate. The organic layer was dried over anhydrous sodium sulfate and concentrated under reduced pressure. The residue was purified by chromatography over silica gel (0-25% ethyl acetate in petroleum ether). The desired Compound Q was obtained as a colorless oil, 45 mg, in 4% yield.

LC-MS: 593.50 [M+1]$^+$. $^1$H NMR (400 MHz, CDCl$_3$): δ 8.21 (s, 1H), 8.16 (s, 1H), 7.50 (ddd, J=25.4, 21.3, 7.6 Hz, 4H), 5.40 (s, 2H), 4.58 (dd, J=5.5, 3.7 Hz, 2H), 4.17 (q, J=7.0 Hz, 2H), 3.97-3.91 (m, 2H), 3.83 (dd, J=5.5, 3.7 Hz, 2H), 3.61 (dd, J=5.6, 3.5 Hz, 2H), 3.49 (dd, J=5.6, 3.5 Hz, 2H), 3.30 (s, 3H), 1.65 (dd, J=15.1, 7.4 Hz, 2H), 1.33 (t, J=7.1 Hz, 3H), 0.93 (t, J=7.4 Hz, 3H).

Example 19—Synthesis of Exemplary Compound R

Compound R was synthesized according to the steps below.

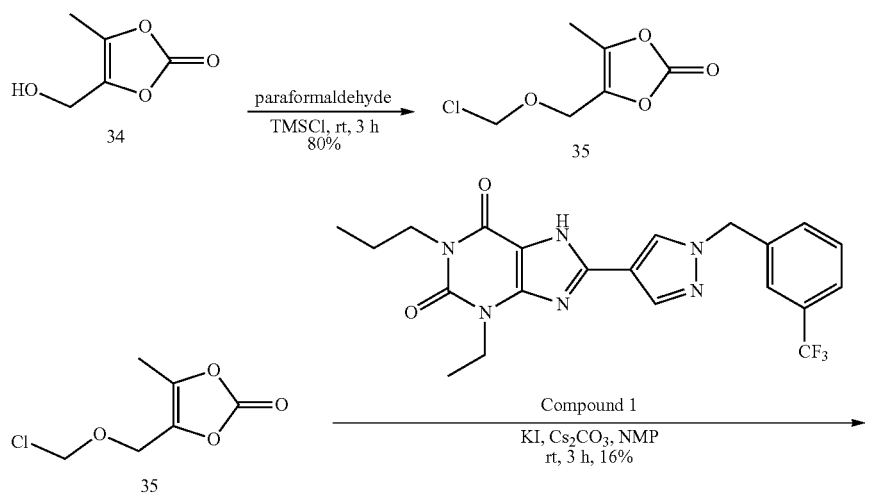

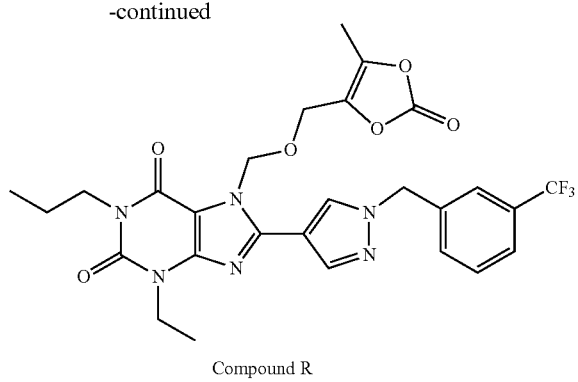

Compound R

A mixture of paraformaldehyde (231 mg, 7.69 mmol, 2.0 eq) and compound 34 (500 mg, 3.85 mmol, 1.0 eq) in chlorotrimethylsilane (5 mL) in a sealed tube was stirred at room temperature for 3 h, monitored by TLC. After completion, the mixture was concentrated under reduced pressure to afford crude compound 35 (550 mg, 80%), which was used for next step directly.

To a solution of compound 1 (554 mg, 1.24 mmol, 1.0 eq) in 1-methyl-2-pyrrolidinone (5 mL) was added potassium iodide (102 mg, 0.62 mmol, 0.5 eq). After being stirred for 15 min, cesium carbonate (1.0 g, 3.09 mmol, 2.5 eq) and compound 35 (550 mg, 3.09 mmol, 2.5 eq) was added. The mixture was stirred at room temperature for 3 h, monitored by TLC. The mixture was diluted with water and extracted with dichloromethane. The organic layer was dried over anhydrous sodium sulfate and concentrated under reduced pressure. The residue was purified by chromatography over silica gel to afford Compound R (120 mg, 16%) as a colorless oil.

LC-MS: 589.35 [M+1]$^+$. $^1$H NMR (400 MHz, CDCl$_3$): δ 8.13 (s, 1H), 8.09 (s, 1H), 7.60 (d, J=7.6 Hz, 1H), 7.52 (d, J=11.7 Hz, 2H), 7.45 (d, J=7.8 Hz, 1H), 5.80 (s, 2H), 5.44 (s, 2H), 4.58 (s, 2H), 4.20 (q, J=7.0 Hz, 3H), 3.99-3.94 (m, 3H), 2.10 (s, 3H), 1.67 (dd, J=15.1, 7.5 Hz, 2H), 1.35 (s, 3H), 0.95 (s, 3H).

Example 20—Synthesis of Exemplary Compound S

Compound S was synthesized according to the steps below.

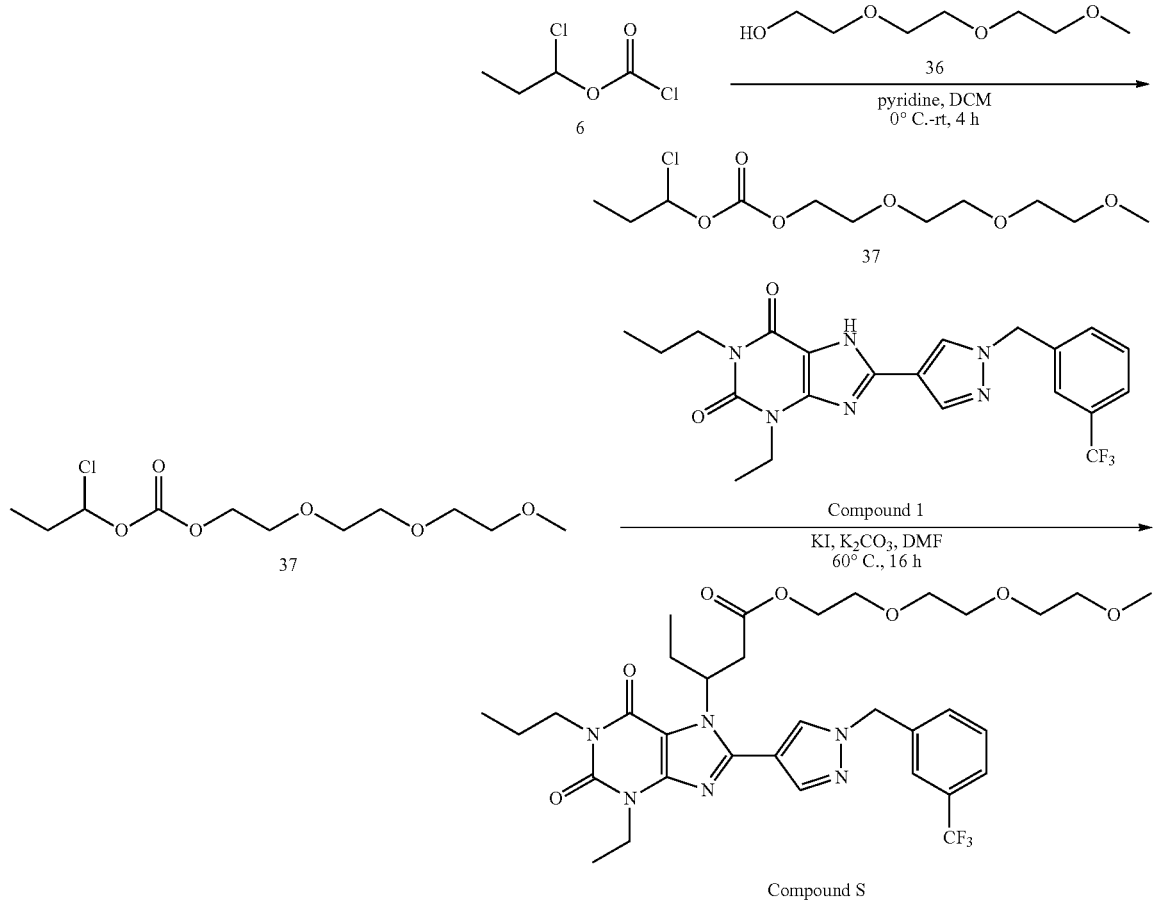

To compound 6 was added pyridine (4.8 g, 61.22 mmol, 2.0 eq) and a solution of compound 36 (5.3 g, 32.14 mmol, 1.05 eq) in dichloromethane (50 mL) at 0° C. The mixture was allowed to warm to room temperature and stirred for 4 h. The progress of the reaction mixture was monitored by $^1$H NMR. The mixture was filtered and the filtrate was concentrated under reduced pressure to afford crude compound 37 (6.0 g, 69%).

To a solution of compound 1 (394 mg, 0.880 mmol, 1.0 eq) in dimethylformamide (5 mL) was added potassium iodide (15 mg, 0.088 mmol, 0.1 eq). After being stirred for 15 min, potassium carbonate (364 mg, 2.64 mmol, 3.0 eq) and compound 37 (1.0 g, 3.52 mmol, 4.0 eq) was added. The mixture was stirred at 60° C. for 16 h and monitored by TLC. The mixture was diluted with water and extracted with dichloromethane. The organic layer was dried over anhydrous sodium sulfate and concentrated under reduced pressure. The residue was purified by silica gel chromatography. The desired Compound S was obtained as a colorless oil, 53 mg, in 8% yield.

LC-MS: 695.55 [M+1]$^+$. $^1$H NMR (400 MHz, CDCl$_3$): δ 8.10 (d, J=8.5 Hz, 2H), 7.61-7.45 (m, 4H), 5.43 (s, 1H), 4.34-4.12 (m, 4H), 4.01-3.93 (m, 2H), 3.67-3.50 (m, 10H), 3.34 (s, 3H), 2.63 (s, 2H), 2.18 (s, 2H), 1.67 (dd, J=15.1, 7.5 Hz, 2H), 1.33 (t, J=7.1 Hz, 3H), 0.94 (t, J=7.4 Hz, 3H), 0.83 (t, J=7.4 Hz, 3H).

Example 21—Synthesis of Exemplary Compound T

Compound T was synthesized according to the steps below.

eq) at room temperature, followed by 3 drops of DMF. The reaction mixture was stirred at room temperature for 5 hrs and concentrated. The crude was dissolved in anhydrous DCM (16 mL), anhydrous ZnCl$_2$ (37 mg, 0.05 eq) was added, cooled to −15° C., and propanal (0.42 mL, 1.2 eq) was added dropwise. The mixture was warmed up to room temperature, stirred overnight, and concentrated. Crude mixture was dissolved in DCM and passed through a small amount of silica gel, eluting with DCM. After concentrating, 1.14 g of compound 40 was obtained as a light yellow oil.

Compound 40 (974 mg, 1.5 eq) was combined with compound 1 (1.08 g, 2.42 mmol), Cs$_2$CO$_3$ (2.36 g, 3 eq), KI (406 mg, 1 eq), and anhydrous DMF (18 mL). The reaction mixture was stirred at room temperature for 16 hrs, filtered through celite, and concentrated. HPLC showed about 3% product. The crude (solid) was treated with DCM several times (about 4 triturations total) until minimum product was observed on the remaining solid. The filtrate was concentrated and purified via FCC (SiO$_2$: 30-50% MeOH/DCM) to provide a mixture containing about 30% product and 70% compound 1. Final purification via Prep-HPLC (H$_2$O/CH$_3$CN containing 0.1% formic acid, 20-100, 30 min, 20 mL/min), followed by concentration, provided 40.3 mg of the desired product Compound T as a yellow oil.

LCMS: [M+H]$^+$=679. $^1$H NMR (300 MHz, CDCl$_3$): δ 8.12 (s, 1H), 8.07 (s, 1H), 7.61 (d, J=7.2 Hz, 1H), 7.49-7.55 (m, 3H), 7.18 (bs, 1H), 5.44 (s, 2H), 4.17 (q, J=6.9 Hz, 2H), 3.98 (m, 2H), 3.71 (t, J=6.6 Hz, 2H), 3.48-3.58 (m, 8H), 3.34

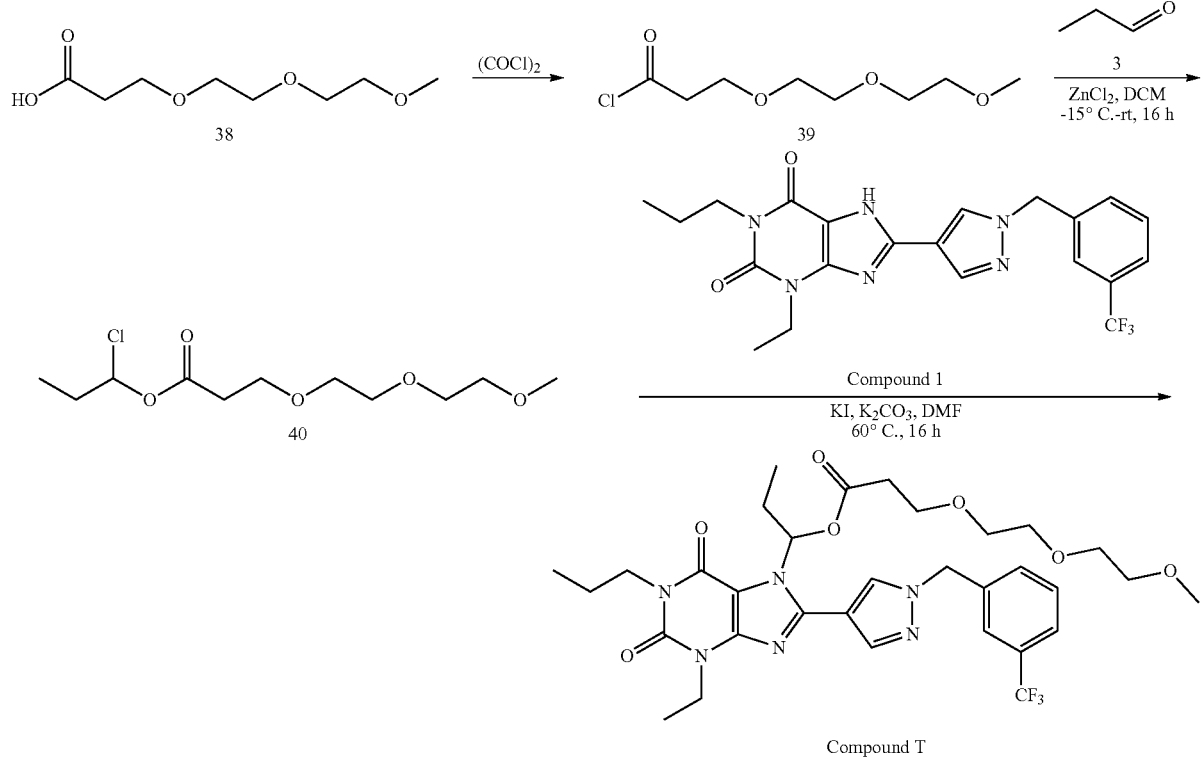

Compound T (s, 3H), 2.56-2.68 (m, 2H), 2.19-2.38 (m, 2H), 1.62-1.75 (m, 2H), 1.34 (t, J=7.2 Hz, 3H), 0.96 (t, J=7.5 Hz, 3H), 0.84 (t, J=7.5 Hz, 3H)

To a solution of 3-[2-(2-Methoxyethoxy)ethoxy]propanoic acid (compound 38) (947 mg, 4.92 mmol) in anhydrous DCM (24 mL) was added oxalyl chloride (0.85 mL, 2

Example 22—Synthesis of Exemplary Compound U

Compound U was synthesized following the steps below:

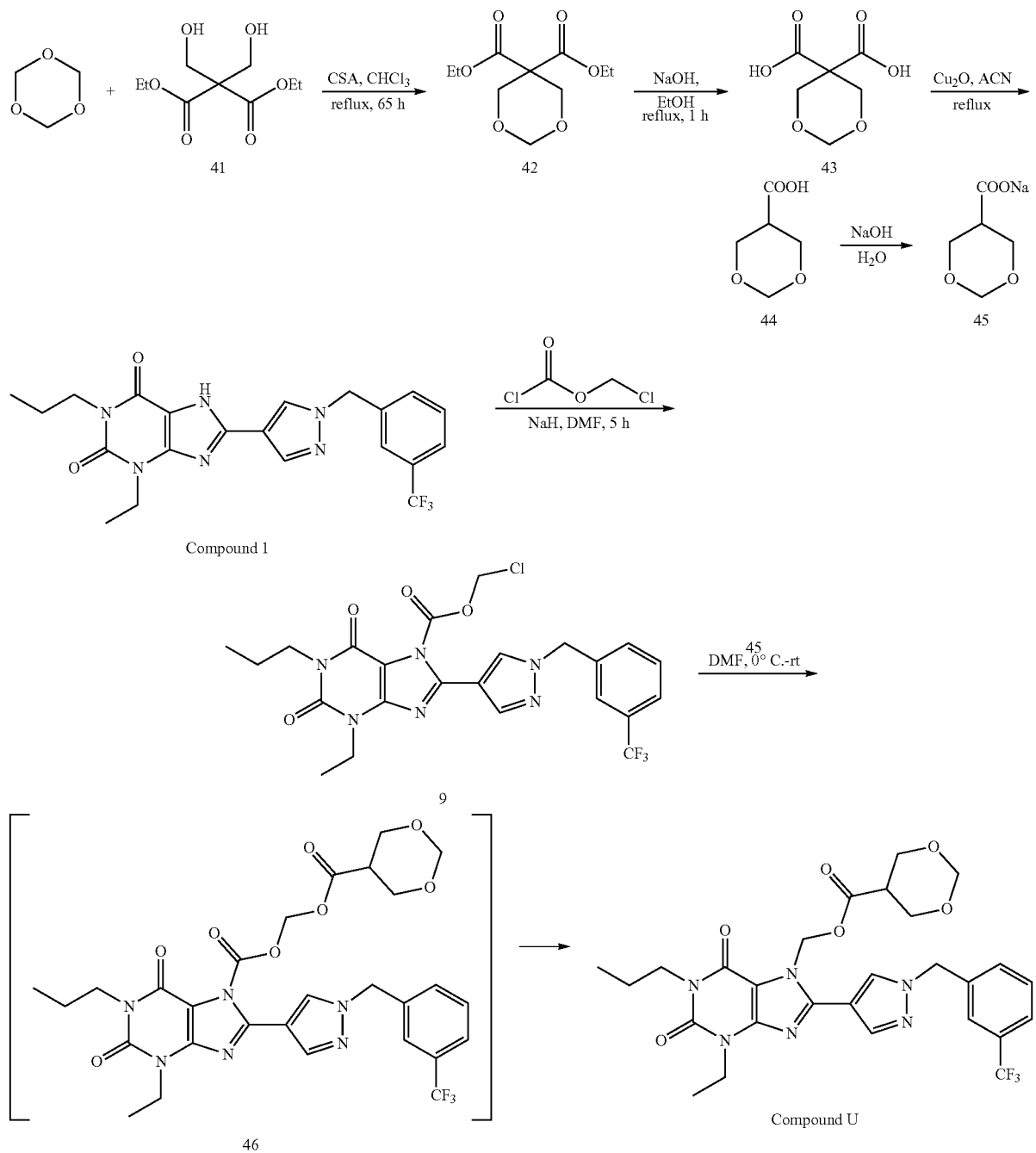

To a mixture of 1,3,5-trioxane (2 g, 22.2 mmol) and compound 41 (44.4 mmol) in CHCl₃ (80 mL), CSA (22.2 mmol) was added and the reaction was refluxed for 65 h. The reaction mixture was filtered and washed with 0.5 N NaOH. The organic layer was dried over sodium sulfate, concentrated and purified by flash chromatography to afford compound 42.

To a mixture of compound 42 (1.3 g, 5.60 mmol) and KOH (0.72 g, 11.2 mmol) in EtOH (50 mL) was added CSA. The reaction was refluxed for 1 h. The solvent was removed. To the residue was added water and the mixture was extracted using ethyl acetate. The aqueous layer was separated, acidified to pH 2 using HCl and extracted using ethyl acetate, dried over MgsO₄ and evaporated to dryness to afford compound 43 (0.9 g). Compound 43 was used without further purification.

To a solution of compound 43 (0.8 g, 4.54 mmol) in ACN (15 mL), Cu₂O (100 mg) was added and the reaction was refluxed for 1 h. The solvent was removed, and the residue was treated with water. The pH of the reaction mixture was adjusted to 2 using concentrated HCl then extracted using diethyl ether. The ether layer was dried over MgSO₄ and evaporated to dryness to afford compound 44.

To a stirred solution of compound 1 (0.3 g, 0.67 mmol) in DMF (15 mL) NaH (0.05 g, 2.01 mmol) was added at room temperature and the reaction was stirred for 30 min After 30 min the reaction mixture was cooled to 0° C. Compound chloromethyl carbonochloridate (0.15 g, 1.34 mmol) was added and the reaction was stirred at room temperature for 2 h. Additional NaH (0.05 g, 2.01 mmol) and chloromethyl carbonochloridate (0.15 g, 1.34 mmol) were added and the reaction was stirred for an additional 1 h. The reaction was quenched using aqueous NH₄Cl and extracted with ethyl acetate, dried over MgSO₄ and evaporated to dryness. The residue was purified using flash chromatography by elution 0 to 60% ethyl acetate in hexane to afford compound 9 (110 g, 30%).

To a stirred solution of compound 9 (0.04 g, 0.09 mmol) in DMF (1 mL) compound 45 (0.024 g, 1.18 mmol) was added at 0° C. and the reaction was stirred for and additional 4 h. The solvent was removed, and the residue was purified using HPLC [0-100% ACN (0.1% TFA) and water (0.1% TFA)] to afford Compound U.

LC-MS: 590.85 (M+1). $^1$H NMR (300 MHz, Chloroform-d) δ 8.06 (s, 1H), 8.00 (s, 1H), 7.65-7.46 (m, 4H), 6.38 (s, 2H), 5.41 (s, 2H), 4.82 (t, J=5.4 Hz, 2H), 4.27-4.16 (m, 4H), 4.04-3.93 (m, 4H), 2.82-2.68 (m, 1H), 1.72-1.69 (m, 2H), 1.36 (t, J=7.1 Hz, 3H), 0.96 (t, J=7.4 Hz, 3H).

Example 23—Synthesis of Exemplary Compound V

Compound V was synthesized following the steps below:

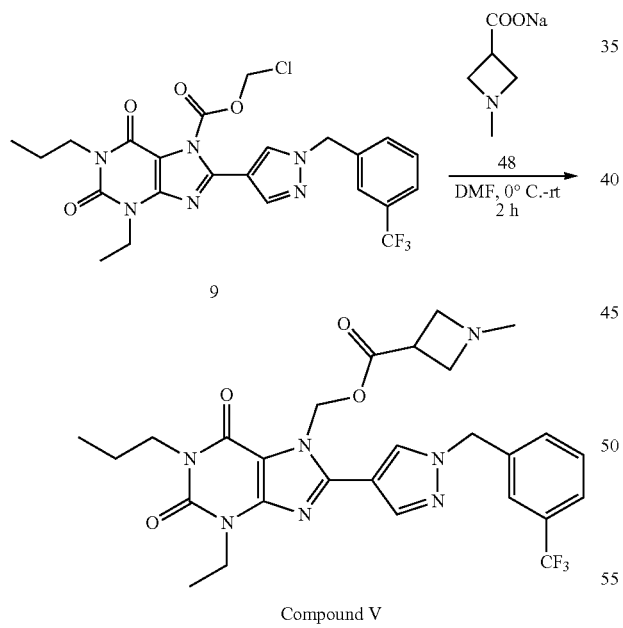

Compound V

To a stirred solution of compound 9 (0.05 g, 0.09 mmol) in DMF (1 mL) compound 48 (0.024, 1.18 mmol) was added and the reaction was stirred for 2 h. LCMS showed the desired mass along with compound 1. The reaction was quenched using aqueous NH₄Cl and extracted using ethyl acetate. The organic layer was dried over sodium sulfate, concentrated and purified using prep HPLC [eluting 0-100% ACN (0.1% TFA) and water (0.1% TFA)] to afford Compound V.

LC-MS: 573.95 (M+1). $^1$H NMR (300 MHz, Chloroform-d) δ 8.02 (s, 1H), 7.96 (s, 1H), 7.67-7.43 (m, 4H), 6.36 (s, 2H), 5.43 (s, 2H), 4.18 (q, J=7.1 Hz, 2H), 4.01-3.91 (m, 2H), 3.52-3.41 (m, 2H), 3.31-3.24 (m, 3H), 2.26 (s, 3H), 1.74-1.63 (m, 2H), 1.35 (t, J=7.2 Hz, 3), 0.95 (m, J=7.1 Hz, 3H).

Example 24—Synthesis of Exemplary Compound AA

Compound AA was synthesized following the steps below:

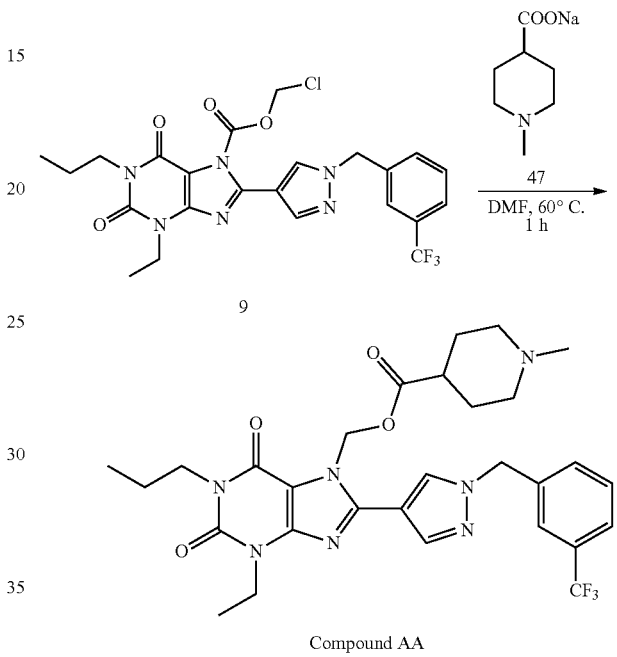

Compound AA

A mixture of compound 9 (0.065 g, 0.12 mmol) and compound 47 (0.054 g, 0.36 mmol) was heated at 60° C. in DMF for 1 h. The solvent was removed, and the compound was purified using prep HPLC by eluting 0-100% ACN (0.1% TFA) and water (0.1% TFA) to afford Compound AA.

LC-MS: 602 (M+1). $^1$H NMR (300 MHz, Chloroform-d) δ 7.96 (s, 1H), 7.95 (s, 1H), 7.69-7.42 (m, 4H), 6.34 (s, 2H), 5.42 (s, 2H), 4.17 (q, J=7.0 Hz, 2H), 4.04-3.91 (m, 2H), 2.81-2.69 (m, 2H), 2.31 (m, 1H), 2.22 (s, 3H), 1.98-1.62 (m, 8H), 1.34 (t, J=7.0 Hz, 3H), 0.94 (t, J=7.4 Hz, 3H).

Example 25—Synthesis of Exemplary Compound BB

Compound BB was synthesized following the steps below:

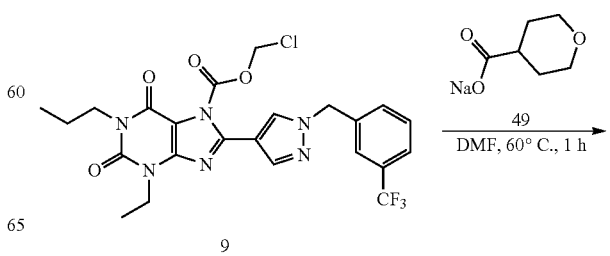

131

-continued

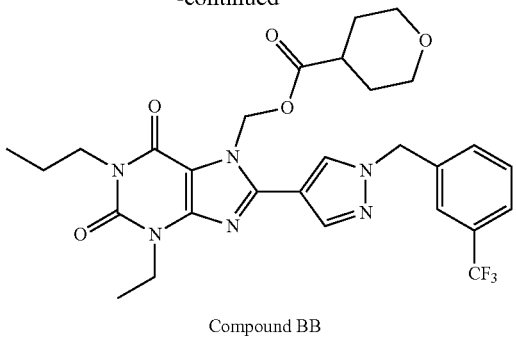

Compound BB

A mixture of compound 9 (0.15 g, 0.27 mmol) and compound 49 (0.25 g, 1.39 mmol) was stirred at room temperature for 45 min and heated at 60° C. in DMF for 30 min LCMS showed complete conversion. The solvent was removed, and the compound was purified using prep HPLC by eluting 0-100% ACN (0.1% TFA) and water (0.1% TFA) to afford Compound BB.

LC-MS: 588.8 (M+1). $^1$H NMR (300 MHz, Chloroform-d) δ 7.96 (dd, J=6.4, 0.7 Hz, 2H), 7.67-7.45 (m, 5H), 6.36 (s, 2H), 5.43 (s, 2H), 4.18 (q, J=7.0 Hz, 2H), 4.02-3.86 (m, 5H), 3.41-3.33 (m, 3H), 2.60-2.55 (m, 1H), 1.82-1.61 (m, 8H), 1.36 (t, J=7.1 Hz, 3H), 0.96 (t, J=7.4 Hz, 3H).

Example 26—Synthesis of Exemplary Compound CC

Compound CC was synthesized following the steps below:

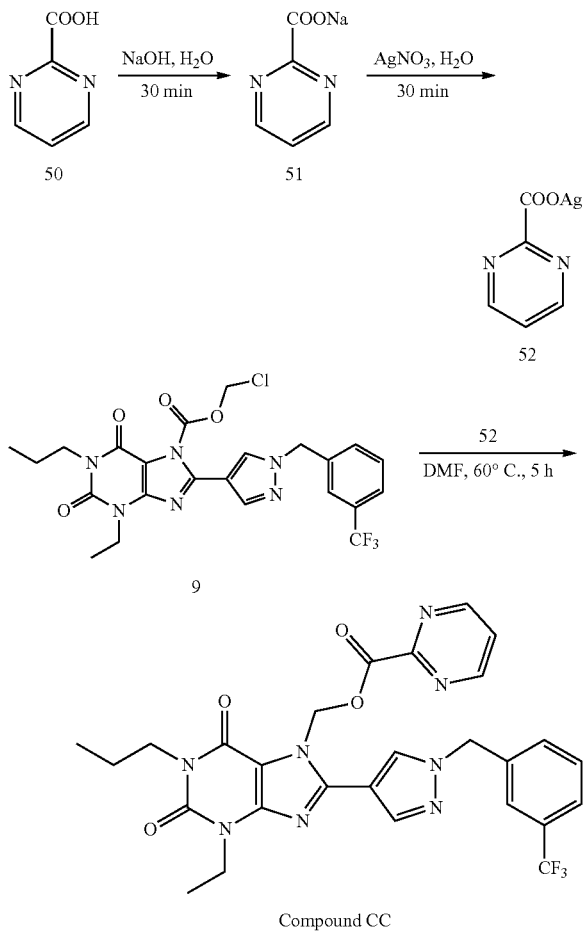

132

An aqueous solution of sodium hydroxide was added to a solution of compound 50 to afford compound 51. To compound 51 (0.2 g, 1.36 mmol) in water was added AgNO$_3$ (0.26 g, 1.52 mmol) dropwise at 0° C. and the reaction mixture was stirred at 0° C. for 1 h. The precipitated solid was filtered, washed with water and dried under vacuum to afford compound 52 (0.3 g).

A mixture of compound 9 (0.05 g, 0.09 mmol) and 52 (0.03 g, 0.18 mmol) was stirred in DMF for 2 h at room temperature. LCMS showed complete conversion. The solvent was removed, and the compound was purified using prep HPLC by eluting 0-100% ACN (0.1% TFA) and water (0.1% TFA) to afford Compound CC.

LC-MS: 582.85 (M+1). $^1$H NMR (300 MHz, Chloroform-d) δ 8.96 (d, J=4.9 Hz, 2H), 8.09 (d, J=3.0 Hz, 2H), 7.65-7.35 (m, 5H), 6.65 (s, 2H), 5.43 (s, 2H), 4.19 (q, J=7.0 Hz, 2H), 3.99-3.93 (m, 2H), 1.74-1.59 (m, 2H), 1.35 (t, J=7.1 Hz, 3H), 0.94 (t, J=7.4 Hz, 3H).

Example 27—Synthesis of Exemplary Compound DD

Compound DD was synthesized following the steps below:

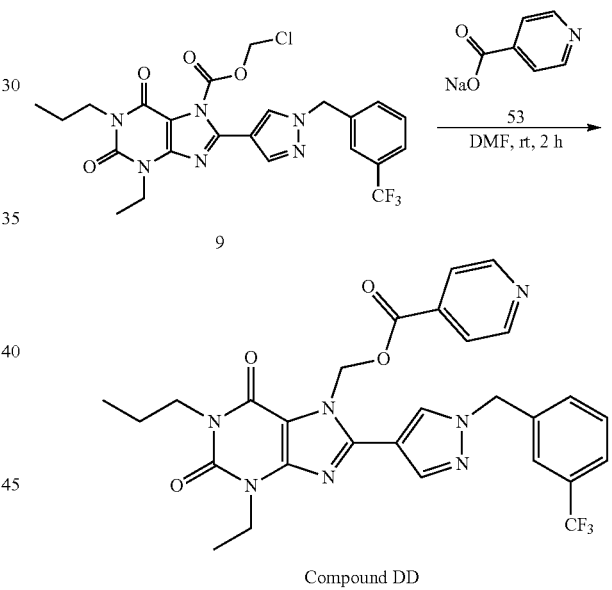

Compound DD

A mixture of compound 9 (0.05 g, 0.09 mmol) and 53 (0.03 g, 0.18 mmol) in DMF was stirred for 2 h at room temperature. LCMS showed complete conversion. The solvent was removed and the compound was purified using prep HPLC by eluting 0-100% ACN (0.1% TFA) and water (0.1% TFA) to afford Compound DD.

LC-MS: 581.9 (M+1). $^1$H NMR (300 MHz, cdcl$_3$) δ 8.78 (s, 2H), 8.01 (d, J=2.0 Hz, 2H), 7.82 (d, J=5.1 Hz, 2H), 7.61-7.47 (m, 4H), 6.62 (s, 2H), 5.43 (s, 2H), 4.19 (q, J=7.0 Hz, 2H), 4.01-3.93 (m, 2H), 1.75-1.62 (m, 2H), 1.36 (t, J=7.0 Hz, 3H), 0.95 (t, J=7.4 Hz, 3H).

Example 28—Synthesis of Exemplary Compound EE

Compound EE was synthesized following the steps below:

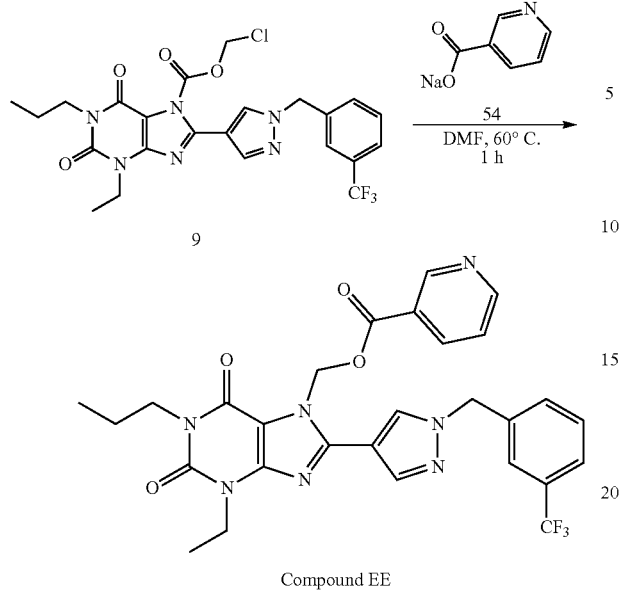

Compound EE

A mixture of compound 9 (0.15 g, 0.28 mmol) and 54 (0.12 g, 0.84 mmol) was heated at 60° C. in DMF for 1 h. LCMS showed complete conversion. The solvent was removed and the compound was purified using prep HPLC by eluting 0-100% ACN (0.1% TFA) and water (0.1% TFA) to afford Compound EE.

LC-MS: 581.8 (M+1). $^1$H NMR (300 MHz, Chloroform-d) δ 9.19 (s, 1H), 8.82 (d, J=4.9 Hz, 1H), 8.33 (dd, J=8.1, 2.1 Hz, 1H), 8.06-7.98 (m, 2H), 7.61-7.44 (m, 5H), 6.62 (s, 2H), 5.43 (s, 2H), 4.20 (q, J=7.0 Hz, 2H), 4.04-3.91 (m, 2H), 1.73-1.62 (m, 2H), 1.36 (t, J=7.0 Hz, 3H), 0.94 (t, J=7.4 Hz, 3H).

Example 29—Synthesis of Exemplary Compound FF

Compound FF was synthesized following the steps below:

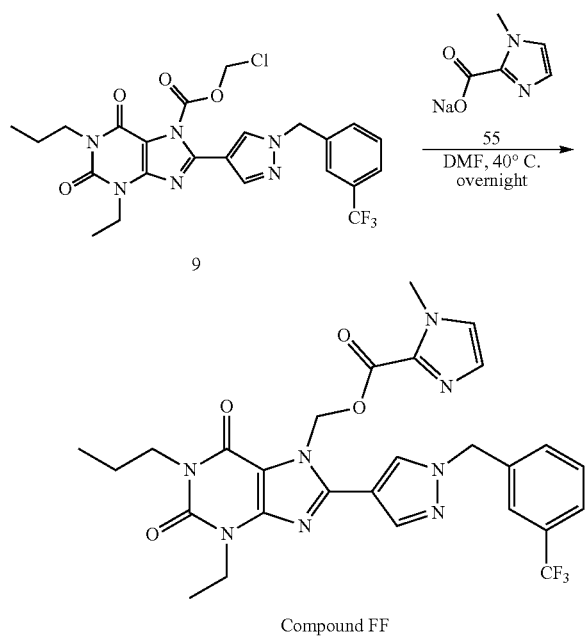

Compound FF

A mixture of compound 9 (0.2 g, 0.37 mmol) and 55 (0.11 g, 0.74 mmol) in DMF was heated at 40° C. for 12 h. LCMS showed the desired mass. The solvent was removed and the compound was purified first using flash column chromatography and then prep HPLC by eluting 0-100% ACN (0.1% TFA) and water (0.1% TFA) to afford Compound FF.

LC-MS: 584.9 (M+1). $^1$H NMR (300 MHz, CDCl$_3$) δ 8.32 (s, 1H), 8.04 (d, J=11.9 Hz, 1H), 7.57-7.47 (m, 4H), 7.15 (s, 1H), 7.09 (d, J=5.0 Hz, 1H), 6.54 (s, 2H), 5.44 (s, 2H), (q, J=7.0 Hz, 2H), 3.99-3.92 (s, 3H), 3.99-3.94 (m, 2H), 1.70-1.61 (m, 2H), 1.34 (t, J=7.1 Hz, 3H), 0.94 (t, J=7.4 Hz, 3H).

Example 30—Synthesis of Exemplary Compound GG

Compound GG was synthesized following the steps below:

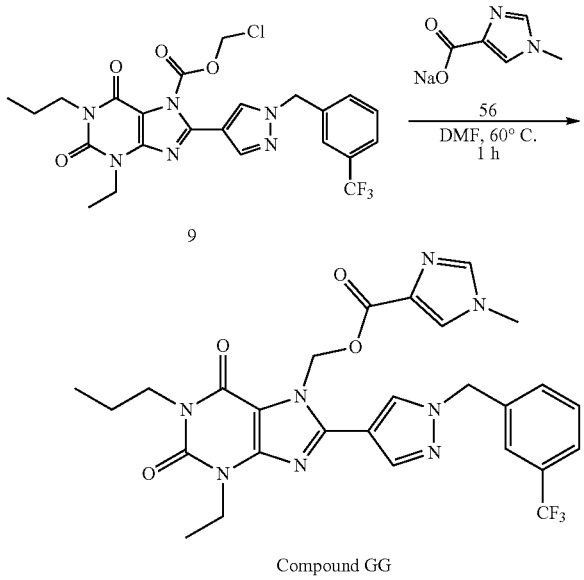

Compound GG

A mixture of compound 9 (0.2 g, 0.37 mmol) and 56 (0.11 g, 0.74 mmol) in DMF was heated at 60° C. for 1 h. LCMS showed complete conversion. The solvent was removed, and compound was purified using prep HPLC by eluting 0-100% ACN (0.1% TFA) and water (0.1% TFA) to afford Compound GG.

LC-MS: 584.9 (M+1). $^1$H NMR (300 MHz, Chloroform-d) δ 8.25 (s, 1H), 8.16 (s, 1H), 8.08 (s, 1H), 7.69 (s, 1H), 7.61-7.45 (m, 4H), 6.55 (s, 2H), 5.45 (s, 2H), 4.19 (q, J=7.0 Hz, 2H), 3.99-3.92 (m, 2H), 3.85 (s, 3H), 1.72-1.60 (m, 2H), 1.35 (t, J=7.0 Hz, 3H), 0.93 (t, J=7.4 Hz, 3H).

Example 31—Pharmacokinetic Properties

Pharmacokinetic studies were carried out in Sprague Dawley rats. Exemplary compounds were administered orally by gavage to groups of three rats using a single oral dose of 5 mg/kg. Each oral dose was prepared as a suspension in 0.5% methylcellulose in water. Blood samples were obtained serially from each rat at 0, 15, 30 min, and then 1, 2, 4, 8, and 24 hrs post dose.

Concentrations of an administered compound and the corresponding metabolite (Compound 1) in rat plasma were determined by a HPLC tandem mass spectrometric (LC/MS/

MS) method. 50 μL Plasma PPT by ISTD in MeOH/Acetonitrile (1:1, v/v). 200 μL of 5 ng/mL Terfenadine and Buspirone was added to in MeOH/Acetonitrile (1:1, v/v) and mixed well. 5 μL of MeOH was added to all samples and vortexed for 1 min and centrifuged at 4000 rpm for 15 mins. The supernatant was diluted 3× with water (with 0.1% FA) and injected for LC/MS/MS analysis.

| | Compound | |
|---|---|---|
| | Compound of Formula (A) or (B) | Compound 1 |
| Matrix | Plasma | Plasma |
| Standard Range | 1-1000 ng/mL | 10-10000 ng/mL |
| Regression | Linear | Linear |
| Weighting | 1/(x * x) | 1/(x * x) |
| LLOQ | 1 ng/mL | 10 ng/mL |
| Internal Standard | 5 ng/mL Terfenadine and Buspirone in MeOH/Acetonitrile (1:1, v/v) | 5 ng/mL Terfenadine and Buspirone in MeOH/Acetonitrile (1:1, v/v) |

Quantification of compounds were achieved by mass spectrometry using Multiple Reaction Monitoring (MRM) mode, monitoring the transitions specific to each exemplary compound and 447.34>405.20 for Compound 1. The quantification limit of the assay was 10 ng/mL for Compound 1.

Pharmacokinetic Analysis

Non-compartmental pharmacokinetic parameters were determined using a commercial program WinNonLin Professional, Version 8.0 (Pharsight, Mountain View, Calif.). Plasma concentration at below level of detection was assumed to be Zero for the calculation of means and pharmacokinetic parameters.

For oral administration, t½ (hr), tmax (hr), Cmax (ng/mL), AUClast (hr*ng/mL), AUCInf (hr*ng/mL), AUC Extr (%), MRTInf (hr), Cmax Ratio (Parent/Pro), AUClast Ratio (Parent/Pro) were determined.

Table 3 describes exemplary $AUC_{last}$ data for representative compounds of Formula (A).

TABLE 3

| Compound | AUC (hr*ng/mL) |
|---|---|
| I | α |
| J | α |
| F | β |
| M | γ |
| G | γ |
| H | β |
| O | β |
| P | β |
| S | β |

α = AUC is greater than or equal to 90,000 hr*ng/mL; β = AUC is less than 90,000 hr*ng/mL and greater than or equal to 30,000 hr*ng/mL; γ = AUC is less than 30,000 hr*ng/mL and greater than 10,000 hr*ng/mL.

Table 4 describes exemplary $AUC_{last}$ data for representative compounds of Formula (B).

TABLE 4

| Compound | AUC (hr*ng/mL) |
|---|---|
| C | α |
| E | α or β |
| L | β |
| N | α |
| J | β |

α = AUC is greater than or equal to 90,000 hr*ng/mL; sβ = AUC is less than 90,000 hr*ng/mL and greater than or equal to 30,000 hr*ng/mL; γ = AUC is less than 30,000 hr*ng/mL and greater than 10,000 hr*ng/mL.

Table 5 describes exemplary $AUC_{last}$ data for Compound 1.

TABLE 5

| Compound | AUC (hr*ng/mL) |
|---|---|
| 1 | γ |

α = AUC is greater than or equal to 90,000 hr*ng/mL; β = AUC is less than 90,000 hr*ng/mL and greater than or equal to 30,000 hr*ng/mL; γ = AUC is less than 30,000 hr*ng/mL.

Example 32: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 0.1-20 mg/mL solution.

Example 33: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 34: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 1-500 mg of a compound described herein, or a pharmaceutically acceptable salt thereof, is placed into Size 4 capsule, or size 1 capsule (hypromellose or hard gelatin) and the capsule is closed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound represented by Formula (III):

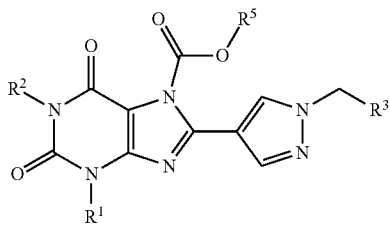

Formula (III)

or a pharmaceutically acceptable salt or solvate thereof; wherein $R^1$ and $R^2$ are each independently selected from hydrogen and substituted or unsubstituted $C_1$-$C_6$alkyl;

$R^3$ is selected from substituted and unsubstituted phenyl, wherein if $R^3$ is substituted then $R^3$ is substituted with one or more groups selected from halogen, —CN, and $C_1$-$C_4$fluoroalkyl;

$R^5$ is hydrogen or $R^7$;

$R^7$ is substituted or unsubstituted $C_1$-$C_6$alkyl, alkyl-(substituted or unsubstituted heterocycloalkyl), —$(CH_2CH_2O)_n$—$R^{11}$, or —$(C(R^{10})_2)_p$—$OR^{11}$;

each $R^9$ is independently selected from hydrogen and $C_1$-$C_6$alkyl;

each $R^{10}$ is independently selected from hydrogen and $C_1$-$C_6$alkyl;

$R^{11}$ is hydrogen, substituted or unsubstituted alkyl, —C(=O)$R^{12}$, or —P(=O)(O$R^9$)$_2$;

$R^{12}$ is hydrogen, substituted or unsubstituted $C_1$-$C_6$alkyl, or substituted or unsubstituted $C_3$-$C_{10}$cycloalkyl;

n is 1, 2, 3, 4, 5, or 6; and p is 1, 2, 3, 4, 5, or 6;

wherein substituted means that the referenced group is substituted with one or more additional groups individually and independently selected from.

2. The compound of claim 1, or a pharmaceutically acceptable salt or solvate thereof, wherein:

$R^1$ and $R^2$ are each independently selected from substituted or unsubstituted $C_1$-$C_6$alkyl;

$R^3$ is selected from substituted or unsubstituted phenyl.

3. The compound of claim 1, or a pharmaceutically acceptable salt or solvate thereof, wherein:

$R^1$ and $R^2$ are each independently selected from methyl, ethyl, n-propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, and neohexyl.

4. The compound of claim 3, wherein the compound has the following structure:

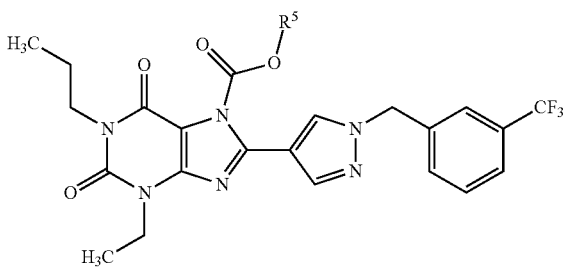

or a pharmaceutically acceptable salt or solvate thereof.

5. The compound of claim 4, or a pharmaceutically acceptable salt or solvate thereof, wherein:

$R^5$ is $R^7$;

$R^7$ is $C_1$-$C_6$alkyl, $(CH_2CH_2O)_n$—$R^{11}$, or —$(c(R^{10})_2)_p$—$OR^{11}$;

each $R^{10}$ is independently selected from hydrogen and methyl;

$R^{11}$ is hydrogen, $C_1$-$C_6$ or —P(=O)(O$R^9$)$_2$;

$R^{12}$ is substituted or unsubstituted $C_1$-$C_6$alkyl, or substituted or unsubstituted $C_3$-$C_{10}$cycloalkyl;

n is 1, 2, 3, 4, 5, or 6; and p is 1, 2, 3, 4, 5, or 6;

wherein substituted means that the referenced group is substituted with one or more additional groups individually and independently selected from $C_1$-$C_6$alkyl.

6. The compound of claim 5, or a pharmaceutically acceptable salt or solvate thereof, wherein:

$R^7$ is $C_1$-$C_6$alkyl.

7. The compound of claim 1, wherein the compound has one of the following structures:

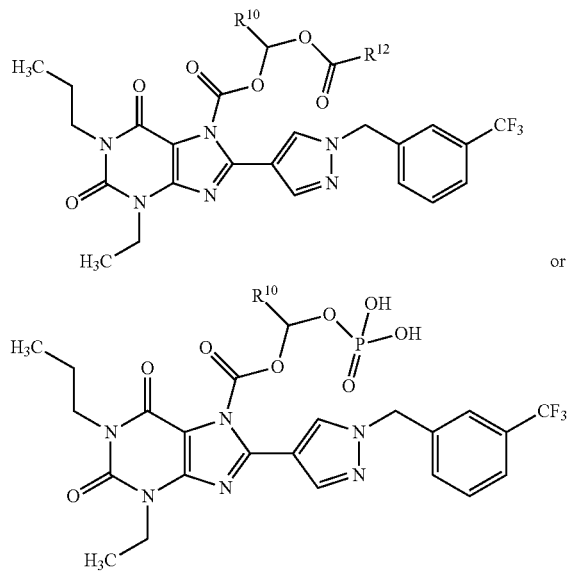

or or a pharmaceutically acceptable salt or solvate thereof.

8. A compound of structure:

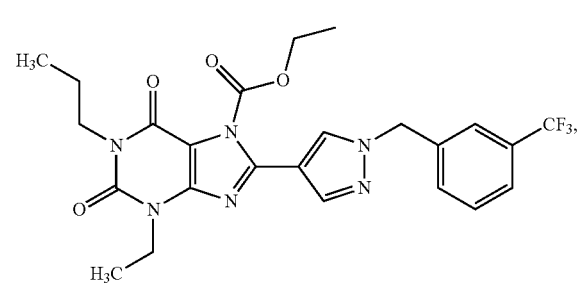

-continued

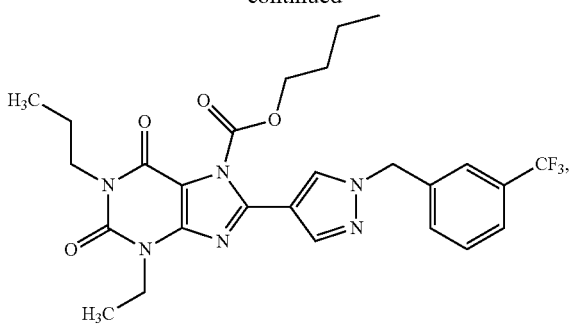

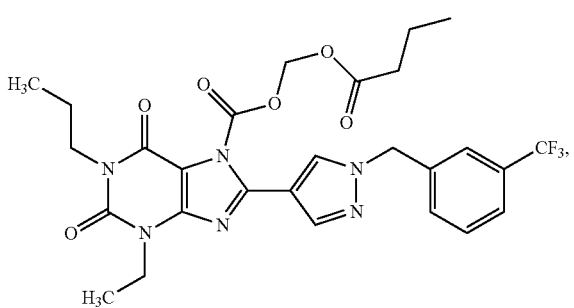

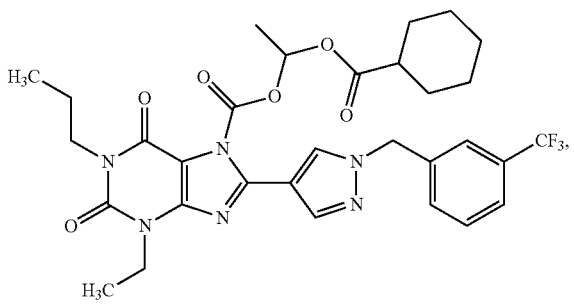

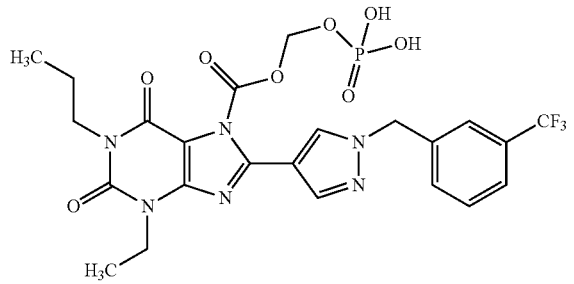

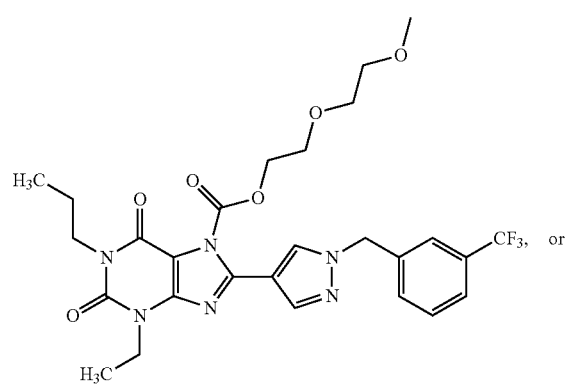

-continued

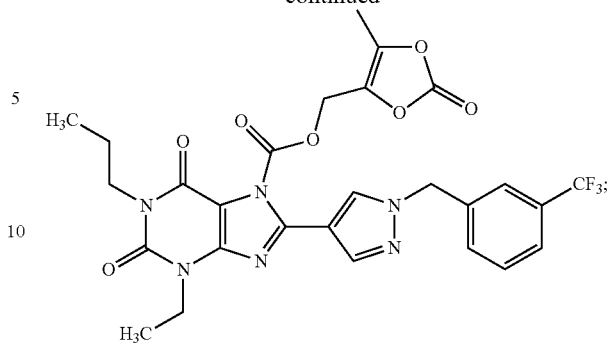

or a pharmaceutically acceptable salt or solvate thereof.

9. A pharmaceutical composition, comprising a compound of claim 1, or any pharmaceutically acceptable salt or solvate thereof; and at least one pharmaceutically acceptable excipient.

10. The pharmaceutical composition of claim 9, wherein the pharmaceutical composition is formulated for administration to a mammal by oral administration, intravenous administration, or subcutaneous administration.

11. The pharmaceutical composition of claim 10, wherein the pharmaceutical composition is in the form of a tablet, a pill, a capsule, a liquid, a suspension, a dispersion, a solution, or an emulsion.

12. The compound of claim 3, wherein the compound has the following structure:

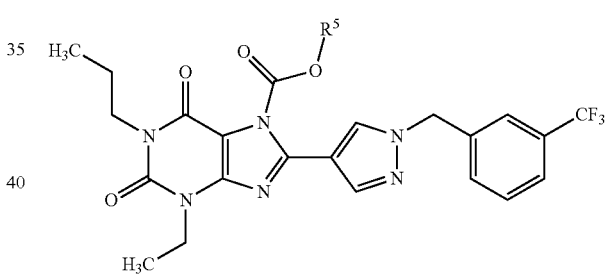

or a pharmaceutically acceptable salt thereof.

13. The compound of claim 12, or a pharmaceutically acceptable salt thereof, wherein:

$R^5$ is $R^7$;

$R^7$ is $C_1$-$C_6$alkyl, -(CH$_2$CH2O)$_{n-R}$$^{11}$, or -(C(R$^{10}$)$_2$)$_p$-OR$^{11}$;

each $R^{10}$ is independently selected from hydrogen and methyl;

R11 is hydrogen, $C_1$-$C_6$alkyl, -C(=O)R$^{12}$, or -P(=O)(OR$^9$)$_2$;

$R^{12}$ is substituted or unsubstituted C1-C6alkyl, or substituted or unsubstituted $C_3$-$C_{10}$cycloalkyl;

n is 1, 2, 3, 4, 5, or 6; and p is 1, 2, 3, 4, 5, or 6;

wherein substituted means that the referenced group is substituted with one or more additional groups individually and independently selected from $C_1$-$C_6$alkyl.

14. The compound of claim 13, or a pharmaceutically acceptable salt thereof, wherein:

$R^7$ is $C_1$-$C_6$alkyl.

15. The compound of claim 1, wherein the compound has one of the following structures:

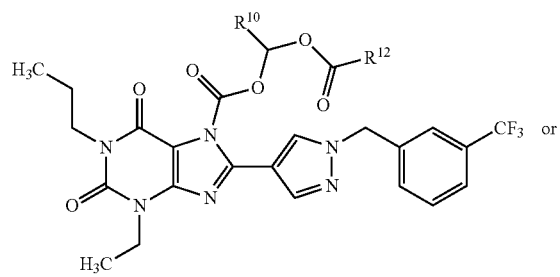

or

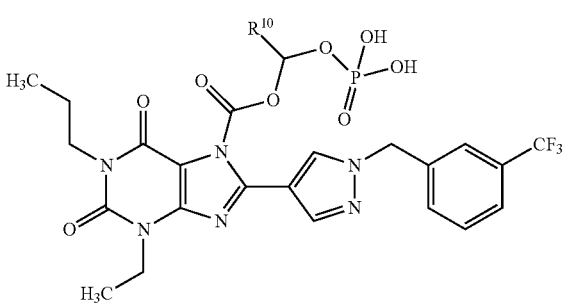

or a pharmaceutically acceptable salt thereof.

16. A compound of structure:

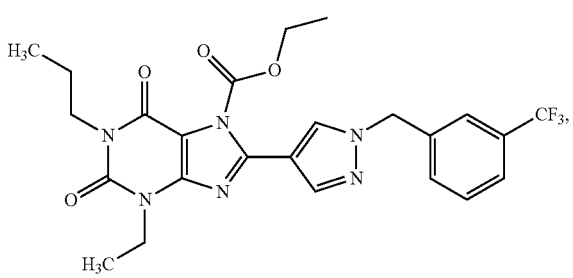 [SMILES: CCCn1c(=O)c2c(nc(-c3cnn(Cc4cccc(C(F)(F)F)c4)c3)n2C(=O)OCC)n(CC)c1=O]

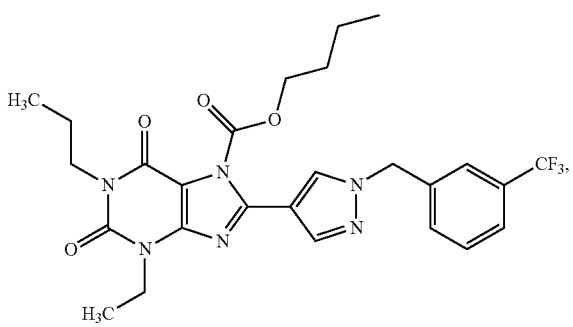

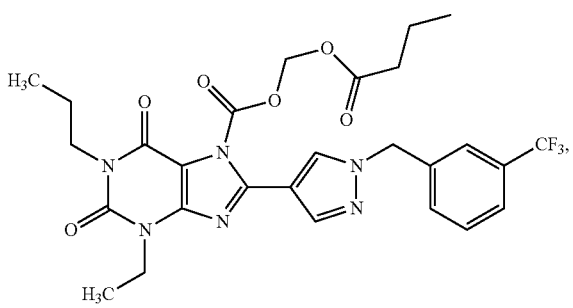

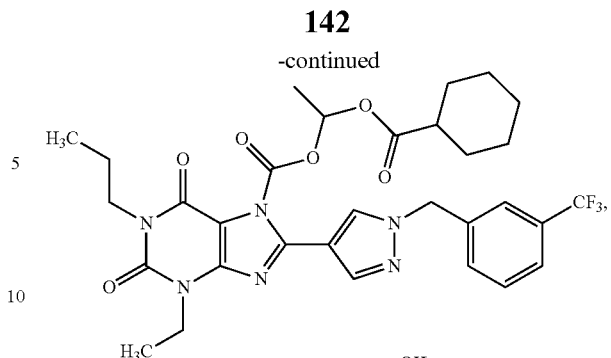

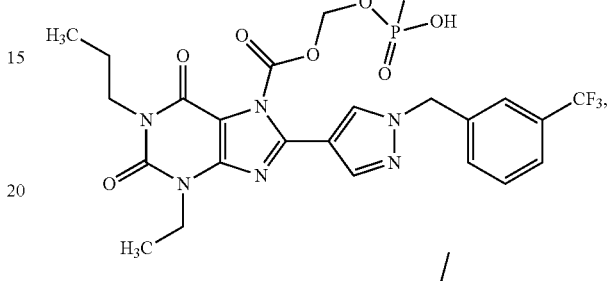

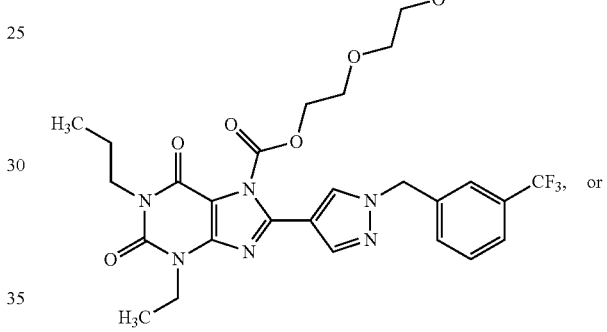, or

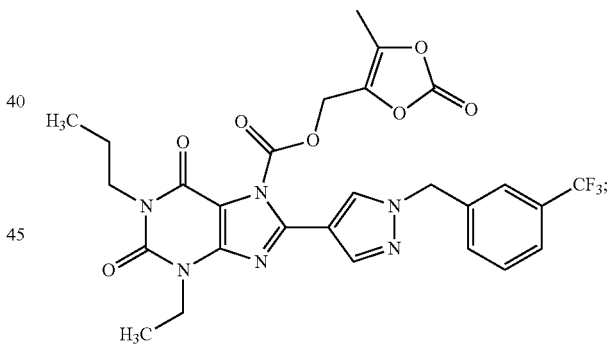;

or a pharmaceutically acceptable salt thereof.

17. A pharmaceutical composition, comprising a compound of claim 1, or any pharmaceutically acceptable salt thereof; and at least one pharmaceutically acceptable excipient.

18. A compound of structure:

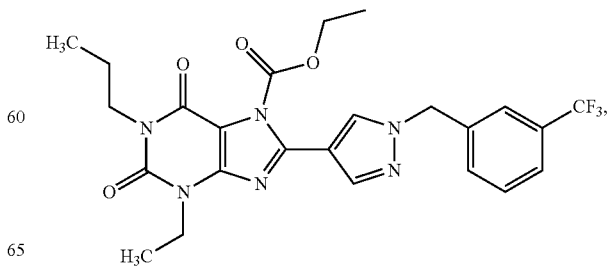

or a pharmaceutically acceptable salt thereof.

19. A compound of structure:
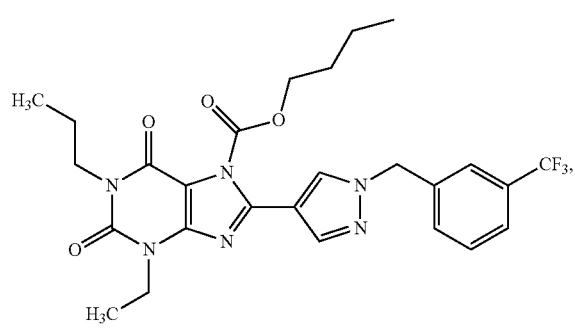 [SMILES: CCCCOC(=O)n1c(-c2cnn(Cc3cccc(C(F)(F)F)c3)c2)nc2c1c(=O)n(CCC)c(=O)n2CC]
or a pharmaceutically acceptable salt thereof.
20. A compound of structure:
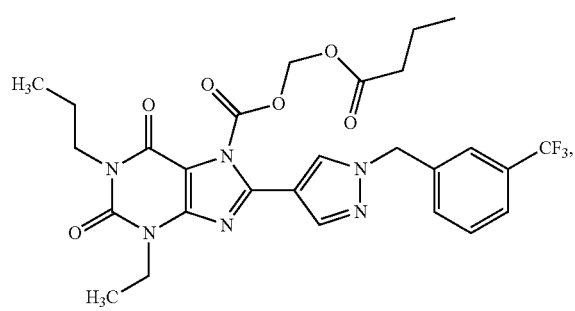 [SMILES: CCCC(=O)OCOC(=O)n1c(-c2cnn(Cc3cccc(C(F)(F)F)c3)c2)nc2c1c(=O)n(CCC)c(=O)n2CC]
or a pharmaceutically acceptable salt thereof.
21. A compound of structure:
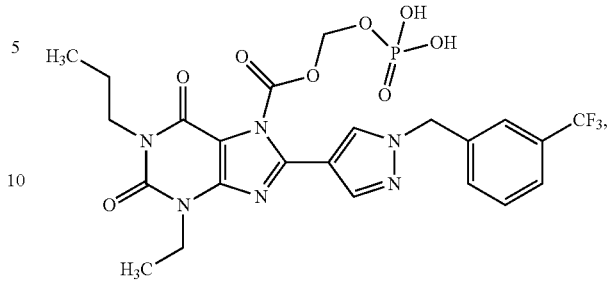
or a pharmaceutically acceptable salt thereof.
22. A compound of structure:
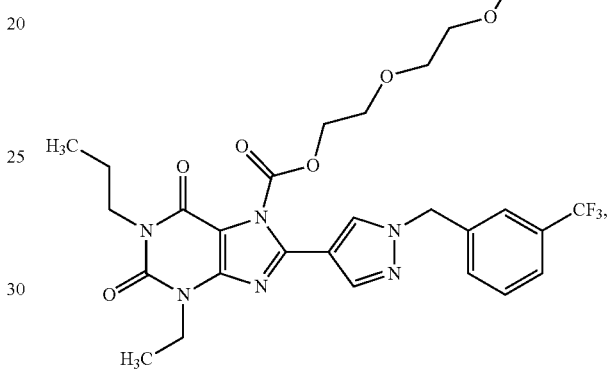
or a pharmaceutically acceptable salt thereof.
* * * * *